US012636376B2

(12) United States Patent
D'Hondt et al.

(10) Patent No.: US 12,636,376 B2
(45) Date of Patent: May 26, 2026

(54) METHODS AND COMPOSITIONS FOR USE OF GROWTH FACTOR ANTIBODIES IN COMBINATION WITH NON-TYROSINE TARGETING KINASE INHIBITORS

(71) Applicant: In3Bio Ltd., Hamilton (BM)

(72) Inventors: Erik D'Hondt, Bazel (BE); Miguel Angel Molina-Vila, Badalona (ES)

( * ) Notice: Subject to any disclaimer, the term of this patent is extended or adjusted under 35 U.S.C. 154(b) by 973 days.

(21) Appl. No.: 17/773,741

(22) PCT Filed: Nov. 6, 2020

(86) PCT No.: PCT/IB2020/000969
§ 371 (c)(1),
(2) Date: May 2, 2022

(87) PCT Pub. No.: WO2021/090069
PCT Pub. Date: May 14, 2021

(65) Prior Publication Data
US 2022/0378891 A1    Dec. 1, 2022

Related U.S. Application Data

(60) Provisional application No. 63/094,018, filed on Oct. 20, 2020, provisional application No. 62/932,131, filed on Nov. 7, 2019.

(51) Int. Cl.
| | |
|---|---|
| *A61K 47/64* | (2017.01) |
| *A61K 31/4184* | (2006.01) |
| *A61K 31/437* | (2006.01) |
| *A61K 31/4439* | (2006.01) |
| *A61K 31/4745* | (2006.01) |
| *A61K 31/506* | (2006.01) |
| *A61K 31/519* | (2006.01) |
| *A61K 31/52* | (2006.01) |
| *A61K 31/5377* | (2006.01) |
| *A61K 31/553* | (2006.01) |
| *A61K 31/685* | (2006.01) |
| *A61K 39/00* | (2006.01) |
| *A61K 39/395* | (2006.01) |
| *A61K 47/65* | (2017.01) |
| *A61P 11/00* | (2006.01) |
| *A61P 35/00* | (2006.01) |

(52) U.S. Cl.
CPC ...... *A61K 47/6425* (2017.08); *A61K 31/4184* (2013.01); *A61K 31/437* (2013.01); *A61K 31/4439* (2013.01); *A61K 31/4745* (2013.01); *A61K 31/506* (2013.01); *A61K 31/519* (2013.01); *A61K 31/52* (2013.01); *A61K 31/5377* (2013.01); *A61K 31/553* (2013.01); *A61K 31/685* (2013.01); *A61K 39/001104* (2018.08); *A61K 39/001131* (2018.08); *A61K*

*39/3955* (2013.01); *A61K 47/642* (2017.08); *A61K 47/65* (2017.08); *A61P 11/00* (2018.01); *A61P 35/00* (2018.01)

(58) Field of Classification Search
CPC .................................................. A61K 47/6425
See application file for complete search history.

(56) References Cited

U.S. PATENT DOCUMENTS

2014/0170063 A1    6/2014   Govindan et al.

FOREIGN PATENT DOCUMENTS

| | | |
|---|---|---|
| CN | 110062633 A | 7/2019 |
| CN | 110381997 A | 10/2019 |
| TW | 201805309 A | 2/2018 |
| WO | 2013/076580 A2 | 5/2013 |
| WO | 2018/175251 A1 | 9/2018 |
| WO | 2019/016597 A2 | 1/2019 |
| WO | 2019/051296 A1 | 3/2019 |

OTHER PUBLICATIONS

Beers and Berkow, (1999), The Merck Manual of Diagnosis and Therapy, 17th edition, pp. 986-995.*
Cutsem et al. 0-027 Beacon CRC study safety lead-in: Assessment of the BRAF inhibitor encorafenib 1 MEK inhibitor binimetinib 1 anti-epidermal growth factor receptor antibody cetuximab for BRAFV600E metastatic colorectal cancer. Jun. 1, 2018.
Anonymous. Encorafenib, Cetuximab, and Nivolumab in Treating Patients with Microsatellite Stable, BRAFV600E Mutated Unresectable or Metastatic Colorectal Cancer. Jul. 12, 2019.
Anonymous. Updated efficacy of the MEK inhibitor trametinib (T), BRAF inhibitor dabrafenib (D), and anti-EGFR antibody panitumumab (P) in patients (pts) with BRAF V600E mutated (BRAFm) metastatic colorectal cancer (mCRC). May 20, 2015.
Codony-Servat, J. et al. Anti-Epidermal Growth Factor Vaccine Antibodies Enhance the Efficacy of Tyrosine Kinase Inhibitors and Delay the Emergence of Resistance in EGFR Mutant Lung Cancer Cells. Sep. 1, 2018.
International Search Report and Written Opinion in corresponding application No. PCT/IB2020/000969 dated Apr. 15, 2021.
Office Action in corresponding Japanese application No. 2022-526005 dated Nov. 5, 2024.
Office Action in corresponding Chinese application No. 202080092428.7 dated Nov. 28, 2024.

* cited by examiner

*Primary Examiner* — Prema M Mertz
(74) *Attorney, Agent, or Firm* — Day Pitney LLP; John C. Serio

(57) ABSTRACT

The disclosure relates to methods for treating cancer. More particularly, the disclosure relates to use of chimeric non-natural synthetic proteins, in combination with non-tyrosine targeting kinase inhibitors (NTKIs), in treating cancer and preventing intrinsic and/or acquired resistance to NTKIs.

5 Claims, 54 Drawing Sheets

Specification includes a Sequence Listing.

| Cell lines | Origin | KRAS mutation |
|---|---|---|
| A549 | Lung, Adenocarcinoma, NSCLC | G12S |
| H23 | Lung, Adenocarcinoma, NSCLC. | G12C |
| DLD1 | Colon, Adenocarcinoma | G13D, also PIK3CA mut and P53 |
| LS174T | Colon, Adenocarcinoma. | G12D, also PIK3CA mut |

DLD1 x C-Ab x Ab - 2 h

EGF effects in trametinib activity in DLD1 cell line

DLD1 x Trametinib - 2 h

LS174T x Trametinib – 2 h

Ab and trametinib combination in LS174T cell line

LS174T x Ab x Trametinib - 2 h

[Trametinib] = 5 nM

Effect of EGF in HT29 cell line

Effects of EGF on the activity of trametinib in the H508 cell line

Anti-EGF VacAbs and trametinib combination in H508 cell line

Effects of EGF on the activity of taselisib in the H508 cell line

Anti-EGF VacAbs and taselisib combination in H508 cell line

Growth curve of taselisib 0,01 µM in combination with anti-EGF VacAbs
in H508 at 14 days Growth curve of taselisib 0,5 µM in combination with anti-EGF VacAbs
in H508 at 14 days Anti-EGF VacAbs activity in HT29 cell line

IF

Anti-EGF VacAbs and trametinib combination in HT29 cell line

Dose-Response of trametinib at 2 hours of incubation in HT29 cell line

Anti-EGF VacAbs with trametinib at 2 hours of incubation in HT29 cell line

BV-NSCLC-002 western blots

| Patient alteration | Cell line used | Cell lines main alteration |
|---|---|---|
| ALK translocated | H2228 | EML4-ALK (v3; E6:A20) |
| KRAS mutant | A549 | KRAS mutant (G12S) |
| ALK and KRAS wild type | SW900 | ALK and KRAS wild type |

SW900 cell line
Dose – Response experiment of a patient with high anti-EGF VacAbs titer Patient ID: 22180004-2a / 22180004-3d

| PatId | Cell line | IHQ ALK | FISH ALK | KRAS TX | EGF 2a | EGF3d | Titer (1/xxx) |
|---|---|---|---|---|---|---|---|
| 22180004 | SW900 (wt) | NEG | | ND | 262,44 | 9,30 | 21000 |

SW900 cell line
Two patients with different anti-EGF VacAbs titer

Patients ID: 27030004 (2a/3d) 29080005 (2a/3d)

| Patid | Cell line | IHQ ALK | FISH ALK | KRAS TX | EGF 2a | EGF3d | Titer (1/xxx) |
|---|---|---|---|---|---|---|---|
| 27030004 | SW900 (wt) | | | | 296,27 | 31,86 | 8300 |
| 29080005 | | NEG | | ND | 185,47 | 17,96 | 2300 |

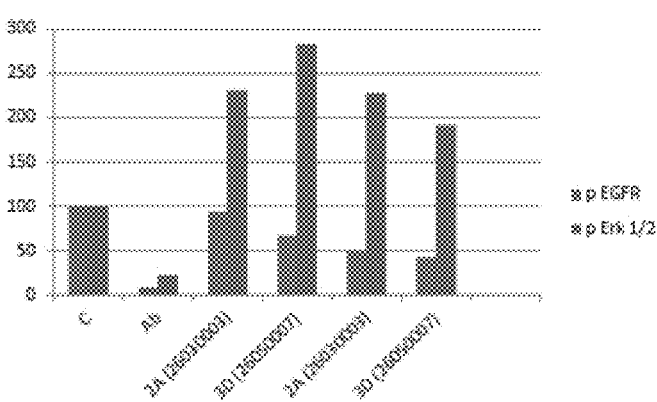
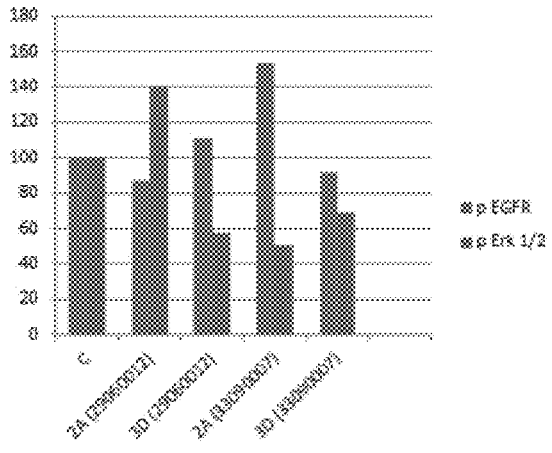
FIG. 42
| CELL LINE | HISTOLOGY | RELEVANT ALTERATION | OTHER ALTERATION |
|---|---|---|---|
| DLD1 | Colorectal ADC | *KRAS* mutant (p.G13D) | *PIK3CA* mutant (p.E545K) |
| LS174T | Colorectal ADC | *KRAS* mutant (p.G12C) | — |
| HT29 | Colorectal ADC | *BRAF* mutant (p.V600E) | — |
| H508 | Colorectal ADC | *PIK3CA* mutant (p.E545K) | *BRAF* mutant (p.G596R) |
FIG. 43

| DRUG | ACTIVITY |
|---|---|
| Trametinib | MEK1/2 inhibitor |
| Taselisib | PI3K inhibitor |
| Alpelisib | PI3K inhibitor |
| Copanlisib | PI3K inhibitor |
| Encorafenib | BRAF inhibitor |

Emergence of resistance to Taselisib (H508)

| CELL LINE | HISTOLOGY | RELEVANT ALTERATION |
|-----------|-----------|---------------------|
| HCC15 | NSCLC (squamous carcinoma) | *NRAS* mutant (p.Q61K) |
| HT29 | Colorectal ADC | *BRAF* mutant (p.V600E) |

| DRUG | ACTIVITY |
|------|----------|
| Trametinib | MEK inhibitor |
| Encorafenib | BRAF inhibitor |

| CELL LINE | HISTOLOGY | RELEVANT ALTERATION | OTHER ALTERATION |
|---|---|---|---|
| H508 | Colorectal ADC | PIK3CA mutant (p.E545K) | BRAF mutant (p.G596R) |

| DRUG | ACTIVITY |
|---|---|
| Alpelisib | PI3KCA inhibitor |
| Copanlisib | PI3KCA inhibitor |

| CELL LINE | HISTOLOGY | RELEVANT ALTERATION |
|-----------|-----------|---------------------|
| LC-2/ad | Lung ADC | RET translocated (CCDC6-RET) |

| DRUG | ACTIVITY |
|------|----------|
| BLU667 | RET inhibitor |

BLU667 with/without EGF in LC-2/ad

| CELL LINE | HISTOLOGY | RELEVANT ALTERATION |
|---|---|---|
| EBC-1 | Squamous Cell Lung Carcinoma | MET amplification |
| Hs746T | Gastric Adenocarcinoma | MET amplification MET exon 14 deletion |

| DRUG | ACTIVITY |
|---|---|
| Capmatinib | MET inhibitor |
| Tepotinib | MET inhibitor |

SEQUENCE LISTING

<160> NUMBER OF SEQ ID NOS: 25

<210> SEQ ID NO 1
<211> LENGTH: 681
<212> TYPE: DNA
<213> ORGANISM: Artificial
<220> FEATURE:
<223> OTHER INFORMATION: Synthetic

<400> SEQUENCE: 1

```
aataccgaaa acgattgccc tctgtctcat gaagcgtatt gtctgcacga cggcgtgtgt      60
atgtacattg aagccctgga caaatatgca tgtaactgtg tcgtgggcta cgtgggggag     120
cgatgtcagt ttcgagacct gcgttggtgg gatgcgcgcg gctcgagcgg taataccgaa     180
aacgattgcc ctctgtctca tgaagcgtat tgtctgcacg acggcgtgtg tatgtacatt     240
gaagccctgg acaaatatgc atgtaactgt gtcgtgggct acgtggggga gcgatgtcag     300
tttcgagacc tgcgttggtg ggatgcgcgc ggcgggtctg gaggtactag tggcggcggt     360
ggagggtcgg gtaccccgca gaacatcacc gacctgtgcg ccgagtacca acacccag      420 atccacaccc tgaacgacaa gatcttctcg tacaccgaga gcctggccga taagcgtgaa     480
atggccatca tcaccttcaa gaacggtgcg accttccagg tggaggtccc gggtagccag     540
cacatcgatt cacagaagaa ggccatcgag cgtatgaagg acaccctgcg tatcgcctac     600
ctgaccgaag ccaaggtgga aaagctgtgc gtctggaaca caagacgcc gcacgccatc      660 gccgccatca gcatggccaa t                                              681
```

<210> SEQ ID NO 2
<211> LENGTH: 227
<212> TYPE: PRT
<213> ORGANISM: Artificial
<220> FEATURE:
<223> OTHER INFORMATION: Synthetic

<400> SEQUENCE: 2

```
Asn Thr Glu Asn Asp Cys Pro Leu Ser His Glu Ala Tyr Cys Leu His
1               5                   10                  15

Asp Gly Val Cys Met Tyr Ile Glu Ala Leu Asp Lys Tyr Ala Cys Asn
                20                  25                  30

Cys Val Val Gly Tyr Val Gly Glu Arg Cys Gln Phe Arg Asp Leu Arg
            35                  40                  45

Trp Trp Asp Ala Arg Gly Ser Ser Gly Asn Thr Glu Asn Asp Cys Pro
    50                  55                  60

Leu Ser His Glu Ala Tyr Cys Leu His Asp Gly Val Cys Met Tyr Ile
65                  70                  75                  80

Glu Ala Leu Asp Lys Tyr Ala Cys Asn Cys Val Val Gly Tyr Val Gly
                85                  90                  95

Glu Arg Cys Gln Phe Arg Asp Leu Arg Trp Trp Asp Ala Arg Gly Gly
                100                 105                 110

Ser Gly Gly Thr Ser Gly Gly Gly Gly Ser Gly Thr Pro Gln Asn
        115                 120                 125

Ile Thr Asp Leu Cys Ala Glu Tyr His Asn Thr Gln Ile His Thr Leu
    130                 135                 140

Asn Asp Lys Ile Phe Ser Tyr Thr Glu Ser Leu Ala Asp Lys Arg Glu
145                 150                 155                 160

Met Ala Ile Ile Thr Phe Lys Asn Gly Ala Thr Phe Gln Val Glu Val
                165                 170                 175
```

-continued

```
Pro Gly Ser Gln His Ile Asp Ser Gln Lys Lys Ala Ile Glu Arg Met
            180                 185                 190

Lys Asp Thr Leu Arg Ile Ala Tyr Leu Thr Glu Ala Lys Val Glu Lys
        195                 200                 205

Leu Cys Val Trp Asn Asn Lys Thr Pro His Ala Ile Ala Ala Ile Ser
    210                 215                 220

Met Ala Asn
225

<210> SEQ ID NO 3
<211> LENGTH: 6369
<212> TYPE: DNA
<213> ORGANISM: Artificial
<220> FEATURE:
<223> OTHER INFORMATION: Synthetic

<400> SEQUENCE: 3
gtccgggcag ccccggcgc agcgcggccg cagcagcctc cgcccccgc acggtgtgag      60 cgcccgacgc ggccgaggcg gccggagtcc cgagctagcc ccggcggccg ccgccgccca     120
gaccggacga caggccacct cgtcggcgtc cgcccgagtc cccgcctcgc cgccaacgcc     180
acaaccaccg cgcacggccc cctgactccg tccagtattg atcgggagag ccggagcgag     240
ctcttcgggg agcagcgatg cgaccctccg ggacggccgg ggcagcgctc ctggcgctgc     300
tggctgcgct ctgcccggcg agtcgggctc tggaggaaaa gaaagtttgc caaggcacga     360
gtaacaagct cacgcagttg ggcactttg aagatcattt tctcagcctc cagaggatgt      420
tcaataactg tgaggtggtc cttgggaatt tggaaattac ctatgtgcag aggaattatg     480
atctttcctt cttaaagacc atccaggagg tggctggtta tgtcctcatt gccctcaaca     540
cagtggagcg aattcctttg gaaaacctgc agatcatcag aggaaatatg tactacgaaa     600
attcctatgc cttagcagtc ttatctaact atgatgcaaa taaaaccgga ctgaaggagc     660
tgcccatgag aaatttacag gaaatcctgc atggcgccgt gcggttcagc aacaaccctg     720
ccctgtgcaa cgtggagagc atccagtggc gggacatagt cagcagtgac tttctcagca     780
acatgtcgat ggacttccag aaccacctgg gcagctgcca aaagtgtgat ccaagctgtc     840
ccaatgggag ctgctggggt gcaggagagg agaactgcca gaaactgacc aaaatcatct     900
gtgcccagca gtgctccggg cgctgccgtg gcaagtcccc cagtgactgc tgccacaacc     960
agtgtgctgc aggctgcaca ggccccgggg agagcgactg cctggtctgc cgcaaattcc    1020
gagacgaagc cacgtgcaag gacacctgcc ccccactcat gctctacaac cccaccacgt    1080
accagatgga tgtgaacccc gagggcaaat acagctttgg tgccacctgc gtgaagaagt    1140
gtccccgtaa ttatgtggtg acagatcacg gctcgtgcgt ccgagcctgt ggggccgaca    1200
gctatgagat ggaggaagac ggcgtccgca agtgtaagaa gtgcgaaggg ccttgccgca    1260
aagtgtgtaa cggaataggt attggtgaat ttaaagactc actctccata aatgctacga    1320
atattaaaca cttcaaaaac tgcacctcca tcagtggcga tctccacatc ctgccggtgg    1380
catttagggg tgactccttc acacatactc ctcctctgga tccacaggaa ctggatattc    1440
tgaaaaccgt aaaggaaatc acagggtttt tgctgattca ggcttggcct gaaaacagga    1500
cggacctcca tgcctttgag aacctagaaa tcatacgcgg caggaccaag caacatggtc    1560
agttttctct tgcagtcgtc agcctgaaca taacatcctt gggattacgc tccctcaagg    1620
agataagtga tggagatgtg ataatttcag gaaacaaaaa tttgtgctat gcaaatacaa    1680
taaactggaa aaaactgttt gggacctccg gtcagaaaac caaaattata agcaacagag    1740
```

-continued

```
gtgaaaacag ctgcaaggcc acaggccagg tctgccatgc cttgtgctcc cccgagggct      1800
gctggggccc ggagcccagg gactgcgtct cttgccggaa tgtcagccga ggcagggaat      1860
gcgtggacaa gtgcaaccTt ctggagggtg agccaaggga gtttgtggag aactcTgagT      1920
gcatacagtg ccacccagag tgcctgcctc aggccatgaa catcacctgc acaggacggg      1980
gaccagacaa ctgtatccag tgtgcccact acattgacgg cccccactgc gtcaagacct      2040
gcccggcagg agtcatggga gaaaacaaca ccctggtctg gaagtacgca gacgccggcc      2100
atgtgtgcca cctgtgccat ccaaactgca cctacggatg cactgggcca ggtcttgaag      2160
gctgtccaac gaatgggcct aagatcccgt ccatcgccac tgggatggtg ggggccctcc      2220
tcttgctgct ggtggtggcc ctggggatcg gcctcttcat gcgaaggcgc cacatcgttc      2280
ggaagcgcac gctgcggagg ctgctgcagg agagggagc tgtggagcct cttacaccca      2340
gtggagaagc tcccaaccaa gctctcttga ggatcttgaa ggaaactgaa ttcaaaaaga      2400
tcaaagtgct gggctccggt gcgttcggca cggtgtataa gggactctgg atcccagaag      2460
gtgagaaagt taaaattccc gtcgctatca aggaattaag agaagcaaca tctccgaaag      2520
ccaacaagga aatcctcgat gaagcctacg tgatggccag cgtggacaac ccccacgtgt      2580
gccgcctgct gggcatctgc ctcacctcca ccgtgcagct catcacgcag ctcatgccct      2640
tcggctgcct cctggactat gtccgggaac acaaagacaa tattggctcc cagtacctgc      2700
tcaactggtg tgtgcagatc gcaaagggca tgaactactt ggaggaccgt cgcttggtgc      2760
accgcgacct ggcagccagg aacgtactgg tgaaaacacc gcagcatgtc aagatcacag      2820
attttgggct ggccaaactg ctgggtgcgg aagagaaaga ataccatgca gaaggaggca      2880
aagtgcctat caagtggatg gcattggaat caattttaca cagaatctat acccaccaga      2940
gtgatgtctg gagctacggg gtgactgttt gggagttgat gacctttgga tccaagccat      3000
atgacggaat ccctgccagc gagatctcct ccatcctgga gaaaggagaa cgcctccctc      3060
agccacccat atgtaccatc gatgtctaca tgatcatggt caagtgctgg atgatagacg      3120
cagatagtcg cccaaagttc cgtgagttga tcatcgaatt ctccaaaatg gcccgagacc      3180
cccagcgcta ccttgtcatt caggggatg aaagaatgca tttgccaagt cctacagact      3240
ccaacttcta ccgtgccctg atggatgaag aagacatgga cgacgtggtg gatgccgacg      3300
agtacctcat cccacagcag ggcttcttca gcagcccctc cacgtcacgg actcccctcc      3360
tgagctctct gagtgcaacc agcaacaatt ccaccgtggc ttgcattgat agaaatgggc      3420
tgcaaagctg tcccatcaag gaagacagct tcttgcagcg atacagctca gaccccacag      3480 gcgcccttgac tgaggacagc atagacgaca ccttcctccc agtgcctgaa tacataaacc      3540
agtccgttcc caaaaggccc gctggctctg tgcagaatcc tgtctatcac aatcagcctc      3600
tgaaccccgc gcccagcaga gacccacact accaggaccc ccacagcact gcagtgggca      3660
accccgagta tctcaacact gtccagccca cctgtgtcaa cagcacattc gacagccctg      3720
cccactgggc ccagaaaggc agccaccaaa ttagcctgga caaccctgac taccagcagg      3780
acttctttcc caaggaagcc aagccaaatg gcatctttaa gggctccaca gctgaaaatg      3840
cagaatacct aagggtcgcg ccacaaagca gtgaatttat tggagcatga ccacggagga      3900
tagtatgagc cctaaaaatc cagactcttt cgatacccag gaccaagcca cagcaggtcc      3960
tccatcccaa cagccatgcc cgcattagct cttagaccca cagactggtt ttgcaacgtt      4020
tacaccgact agccaggaag tacttccacc tcgggcacat tttgggaagt tgcattcctt      4080
```

-continued

```
tgtcttcaaa ctgtgaagca tttacagaaa cgcatccagc aagaatattg tccctttgag    4140
cagaaattta tctttcaaag aggtatattt gaaaaaaaaa aaaagtatat gtgaggattt    4200
ttattgattg gggatcttgg agtttttcat tgtcgctatt gatttttact tcaatgggct    4260
cttccaacaa ggaagaagct tgctggtagc acttgctacc ctgagttcat ccaggcccaa    4320
ctgtgagcaa ggagcacaag ccacaagtct tccagaggat gcttgattcc agtggttctg    4380
cttcaaggct tccactgcaa aacactaaag atccaagaag gccttcatgg ccccagcagg    4440
ccggatcggt actgtatcaa gtcatggcag gtacagtagg ataagccact ctgtcccttc    4500
ctgggcaaag aagaaacgga ggggatggaa ttcttcctta gacttacttt tgtaaaaatg    4560
tccccacggt acttactccc cactgatgga ccagtggttt ccagtcatga gcgttagact    4620
gacttgtttg tcttccattc cattgttttg aaactcagta tgctgcccct gtcttgctgt    4680
catgaaatca gcaagagagg atgacacatc aaataataac tcggattcca gcccacattg    4740
gattcatcag catttggacc aatagcccac agctgagaat gtggaatacc taaggatagc    4800
accgcttttg ttctcgcaaa aacgtatctc ctaatttgag gctcagatga aatgcatcag    4860
gtcctttggg gcatagatca gaagactaca aaaatgaagc tgctctgaaa tctcctttag    4920
ccatcacccc aaccccccaa aattagtttg tgttacttat ggaagatagt tttctccttt    4980
tacttcactt caaaagcttt ttactcaaag agtatatgtt ccctccaggt cagctgcccc    5040
caaaccccct ccttacgctt tgtcacacaa aaagtgtctc tgccttgagt catctattca    5100
agcacttaca gctctggcca caacagggca ttttacaggt gcgaatgaca gtagcattat    5160
gagtagtgtg gaattcaggt agtaaatatg aaactagggt ttgaaattga taatgctttc    5220
acaacatttg cagatgtttt agaaggaaaa aagttccttc ctaaaataat ttctctacaa    5280
ttggaagatt ggaagattca gctagttagg agcccacctt ttttcctaat ctgtgtgtgc    5340
cctgtaacct gactggttaa cagcagtcct ttgtaaacag tgttttaaac tctcctagtc    5400
aatatccacc ccatccaatt tatcaaggaa gaaatggttc agaaaatatt ttcagcctac    5460
agttatgttc agtcacacac acatacaaaa tgttcctttt gcttttaaag taattttttga    5520 ctcccagatc agtcagagcc cctacagcat tgttaagaaa gtatttgatt tttgtctcaa    5580
tgaaaataaa actatattca tttccactct attatgctct caaatacccc taagcatcta    5640
tactagcctg gtatgggtat gaaagataca aagataaata aaacatagtc cctgattcta    5700
agaaattcac aatttagcaa aggaaatgga ctcatagatg ctaaccttaa aacaacgtga    5760
caaatgccag acaggaccca tcagccaggc actgtgagag cacagagcag ggaggttggg    5820
tcctgcctga ggagacctgg aagggaggcc tcacaggagg atgaccaggt ctcagtcagc    5880
ggggaggtgg aaagtgcagg tgcatcaggg gcaccctgac cgaggaaaca gctgccagag    5940
gcctccactg ctaaagtcca cataaggctg aggtcagtca ccctaaacaa cctgctccct    6000
ctaagccagg ggatgagctt ggagcatccc acaagttccc taaaagttgc agcccccagg    6060
gggattttga gctatcatct ctgcacatgc ttagtgagaa gactacacaa catttctaag    6120
aatctgagat tttatattgt cagttaacca ctttcattat tcattcacct caggacatgc    6180
agaaatattt cagtcagaac tgggaaacag aaggacctac attctgctgt cacttatgtg    6240
tcaagaagca gatgatcgat gaggcaggtc agttgtaagt gagtcacatt gtagcattaa    6300
attctagtat ttttgtagtt tgaaacagta acttaataaa agagcaaaag ctaaaaaaaa    6360
aaaaaaaaa                                                            6369
```

```
<210> SEQ ID NO 4
<211> LENGTH: 1210
<212> TYPE: PRT
<213> ORGANISM: Artificial
<220> FEATURE:
<223> OTHER INFORMATION: Synthetic

<400> SEQUENCE: 4

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
```

-continued

```
           370                 375                 380
Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
                435                 440                 445

Gly Leu Arg Ser Leu Lys Glu Ile Ser Asp Gly Asp Val Ile Ile Ser
            450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
        610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
        770                 775                 780

Thr Val Gln Leu Ile Thr Gln Leu Met Pro Phe Gly Cys Leu Leu Asp
785                 790                 795                 800
```

-continued

```
Tyr Val Arg Glu His Lys Asp Asn Ile Gly Ser Gln Tyr Leu Leu Asn
            805             810             815

Trp Cys Val Gln Ile Ala Lys Gly Met Asn Tyr Leu Glu Asp Arg Arg
            820             825             830

Leu Val His Arg Asp Leu Ala Ala Arg Asn Val Leu Val Lys Thr Pro
            835             840             845

Gln His Val Lys Ile Thr Asp Phe Gly Leu Ala Lys Leu Leu Gly Ala
        850             855             860

Glu Glu Lys Glu Tyr His Ala Glu Gly Gly Lys Val Pro Ile Lys Trp
865             870             875             880

Met Ala Leu Glu Ser Ile Leu His Arg Ile Tyr Thr His Gln Ser Asp
            885             890             895

Val Trp Ser Tyr Gly Val Thr Val Trp Glu Leu Met Thr Phe Gly Ser
            900             905             910

Lys Pro Tyr Asp Gly Ile Pro Ala Ser Glu Ile Ser Ser Ile Leu Glu
            915             920             925

Lys Gly Glu Arg Leu Pro Gln Pro Pro Ile Cys Thr Ile Asp Val Tyr
        930             935             940

Met Ile Met Val Lys Cys Trp Met Ile Asp Ala Asp Ser Arg Pro Lys
945             950             955             960

Phe Arg Glu Leu Ile Ile Glu Phe Ser Lys Met Ala Arg Asp Pro Gln
            965             970             975

Arg Tyr Leu Val Ile Gln Gly Asp Glu Arg Met His Leu Pro Ser Pro
            980             985             990

Thr Asp Ser Asn Phe Tyr Arg Ala  Leu Met Asp Glu Glu  Asp Met Asp
        995             1000            1005

Asp Val  Val Asp Ala Asp Glu  Tyr Leu Ile Pro Gln  Gln Gly Phe
1010            1015            1020

Phe Ser  Ser Pro Ser Thr Ser  Arg Thr Pro Leu Leu  Ser Ser Leu
1025            1030            1035

Ser Ala  Thr Ser Asn Asn Ser  Thr Val Ala Cys Ile  Asp Arg Asn
1040            1045            1050

Gly Leu  Gln Ser Cys Pro Ile  Lys Glu Asp Ser Phe  Leu Gln Arg
1055            1060            1065

Tyr Ser  Ser Asp Pro Thr Gly  Ala Leu Thr Glu Asp  Ser Ile Asp
1070            1075            1080

Asp Thr  Phe Leu Pro Val Pro  Glu Tyr Ile Asn Gln  Ser Val Pro
1085            1090            1095

Lys Arg  Pro Ala Gly Ser Val  Gln Asn Pro Val Tyr  His Asn Gln
1100            1105            1110

Pro Leu  Asn Pro Ala Pro Ser  Arg Asp Pro His Tyr  Gln Asp Pro
1115            1120            1125

His Ser  Thr Ala Val Gly Asn  Pro Glu Tyr Leu Asn  Thr Val Gln
1130            1135            1140

Pro Thr  Cys Val Asn Ser Thr  Phe Asp Ser Pro Ala  His Trp Ala
1145            1150            1155

Gln Lys  Gly Ser His Gln Ile  Ser Leu Asp Asn Pro  Asp Tyr Gln
1160            1165            1170

Gln Asp  Phe Phe Pro Lys Glu  Ala Lys Pro Asn Gly  Ile Phe Lys
1175            1180            1185

Gly Ser  Thr Ala Glu Asn Ala  Glu Tyr Leu Arg Val  Ala Pro Gln
1190            1195            1200
```

```
Ser Ser  Glu Phe Ile Gly Ala
    1205                1210

<210> SEQ ID NO 5
<211> LENGTH: 5700
<212> TYPE: DNA
<213> ORGANISM: Artificial
<220> FEATURE:
<223> OTHER INFORMATION: Synthetic

<400> SEQUENCE: 5
aaaaagagaa actgttggga gaggaatcgt atctccatat ttcttctttc agccccaatc        60
caagggttgt agctggaact ttccatcagt tcttcctttc tttttcctct ctaagccttt       120
gccttgctct gtcacagtga agtcagccag agcagggctg ttaaactctg tgaaatttgt       180 cataaagggtg tcaggtattt cttactggct tccaaagaaa catagataaa gaaatctttc      240
ctgtggcttc ccttggcagg ctgcattcag aaggtctctc agttgaagaa agagcttgga       300
ggacaacagc acaacaggag agtaaaagat gccccagggc tgaggcctcc gctcaggcag       360
ccgcatctgg ggtcaatcat actcaccttg cccgggccat gctccagcaa aatcaagctg       420
ttttcttttg aaagttcaaa ctcatcaaga ttatgctgct cactcttatc attctgttgc       480
cagtagtttc aaaatttagt tttgttagtc tctcagcacc gcagcactgg agctgtcctg       540
aaggtactct cgcaggaaat gggaattcta cttgtgtggg tcctgcaccc ttcttaattt       600
tctcccatgg aaatagtatc tttaggattg acacagaagg aaccaattat gagcaattgg       660
tggtggatgc tggtgtctca gtgatcatgg attttcatta taatgagaaa agaatctatt       720
gggtggattt agaaagacaa cttttgcaaa gagtttttct gaatgggtca aggcaagaga       780
gagtatgtaa tatagagaaa aatgtttctg gaatggcaat aaattggata aatgaagaag       840
ttatttggtc aaatcaacag gaaggaatca ttacagtaac agatatgaaa ggaaataatt       900
cccacattct tttaagtgct ttaaaatatc ctgcaaatgt agcagttgat ccagtagaaa       960
ggtttatatt ttggtcttca gaggtggctg gaagccttta tagagcagat ctcgatggtg      1020
tgggagtgaa ggctctgttg gagacatcag agaaaataac agctgtgtca ttggatgtgc      1080
ttgataagcg gctgttttgg attcagtaca acagagaagg aagcaattct cttatttgct      1140
cctgtgatta tgatggaggt tctgtccaca ttagtaaaca tccaacacag cataatttgt      1200
ttgcaatgtc cctttttggt gaccgtatct tctattcaac atggaaaatg aagacaattt      1260
ggatagccaa caaacacact ggaaaggaca tggttagaat taacctccat tcatcatttg      1320
taccacttgg tgaactgaaa gtagtgcatc cacttgcaca acccaaggca gaagatgaca      1380
cttgggagcc tgagcagaaa ctttgcaaat tgaggaaagg aaactgcagc agcactgtgt      1440
gtgggcaaga cctccagtca cacttgtgca tgtgtgcaga gggatacgcc ctaagtcgag      1500
accggaagta ctgtgaagat gttaatgaat gtgctttttg gaatcatggc tgtactcttg      1560
ggtgtaaaaa caccctgga tcctattact gcacgtgccc tgtaggattt gttctgcttc       1620
ctgatgggaa acgatgtcat caacttgttt cctgtccacg caatgtgtct gaatgcagcc      1680
atgactgtgt tctgacatca gaaggtccct tatgtttctg tcctgaaggc tcagtgcttg      1740
agagagatgg gaaaacatgt agcggttgtt cctcacccga taatggtgga gtagccagc      1800 tctgcgttcc tcttagccca gtatcctggg aatgtgattg ctttcctggg tatgacctac      1860
aactggatga aaaaagctgt gcagcttcag gaccacaacc attttttgctg tttgccaatt      1920 ctcaagatat tcgacacatg catttttgatg gaacagacta tggaactctg ctcagccagc      1980
```

-continued

```
agatgggaat ggtttatgcc ctagatcatg accctgtgga aaataagata tactttgccc    2040
atacagccct gaagtggata gagagagcta atatggatgg ttcccagcga gaaaggctta    2100
ttgaggaagg agtagatgtg ccagaaggtc ttgctgtgga ctggattggc cgtagattct    2160
attggacaga cagagggaaa tctctgattg gaaggagtga tttaaatggg aaacgttcca    2220
aaataatcac taaggagaac atctctcaac cacgaggaat tgctgttcat ccaatggcca    2280
agagattatt ctggactgat acagggatta atccacgaat tgaaagttct tccctccaag    2340
gccttggccg tctggttata gccagctctg atctaatctg gcccagtgga ataacgattg    2400
acttcttaac tgacaagttg tactggtgcg atgccaagca gtctgtgatt gaaatggcca    2460
atctggatgg ttcaaaacgc cgaagactta cccagaatga tgtaggtcac ccatttgctg    2520
tagcagtgtt tgaggattat gtgtggttct cagattgggc tatgccatca gtaatgagag    2580
taaacaagag gactggcaaa gatagagtac gtctccaagg cagcatgctg aagccctcat    2640
cactggttgt ggttcatcca ttggcaaaac caggagcaga tccctgctta tatcaaaacg    2700
gaggctgtga acatatttgc aaaaagaggc ttggaactgc ttggtgttcg tgtcgtgaag    2760
gttttatgaa agcctcagat gggaaaacgt gtctggctct ggatggtcat cagctgttgg    2820
caggtggtga agttgatcta aagaaccaag taacaccatt ggacatcttg tccaagacta    2880
gagtgtcaga agataacatt acagaatctc aacacatgct agtggctgaa atcatggtgt    2940
cagatcaaga tgactgtgct cctgtgggat gcagcatgta tgctcggtgt atttcagagg    3000
gagaggatgc cacatgtcag tgtttgaaag gatttgctgg ggatggaaaa ctatgttctg    3060
atatagatga atgtgagatg ggtgtcccag tgtgcccccc tgcctcctcc aagtgcatca    3120
acaccgaagg tggttatgtc tgccggtgct cagaaggcta ccaaggagat gggattcact    3180
gtcttgatat tgatgagtgc caactggggg agcacagctg tggagagaat gccagctgca    3240
caaatacaga gggaggctat acctgcatgt gtgctggacg cctgtctgaa ccaggactga    3300
tttgccctga ctctactcca cccccctcacc tcagggaaga tgaccaccac tattccgtaa    3360
gaaatagtga ctctgaatgt cccctgtccc acgatgggta ctgcctccat gatggtgtgt    3420
gcatgtatat tgaagcattg gacaagtatg catgcaactg tgttgttggc tacatcgggg    3480
agcgatgtca gtaccgagac ctgaagtggt gggaactgcg ccacgctggc cacgggcagc    3540
agcagaaggt catcgtggtg gctgtctgcg tggtggtgct tgtcatgctg ctcctcctga    3600
gcctgtgggg ggcccactac tacaggactc agaagctgct atcgaaaaac ccaaagaatc    3660
cttatgagga gtcgagcaga gatgtgagga gtcgcaggcc tgctgacact gaggatggga    3720
tgtcctcttg ccctcaacct tggtttgtgg ttataaaaga acaccaagac ctcaagaatg    3780
ggggtcaacc agtggctggt gaggatggcc aggcagcaga tgggtcaatg caaccaactt    3840
catggaggca ggagccccag ttatgtggaa tgggcacaga gcaaggctgc tggattccag    3900
tatccagtga taagggctcc tgtccccagg taatggagcg aagctttcat atgccctcct    3960
atgggacaca gacccttgaa gggggtgtcg agaagcccca ttctctccta tcagctaacc    4020
cattatggca acaaagggcc ctggacccac cacaccaaat ggagctgact cagtgaaaac    4080
tggaattaaa aggaaagtca agaagaatga actatgtcga tgcacagtat cttttctttc    4140
aaaagtagag caaaactata ggttttggtt ccacaatctc tacgactaat cacctactca    4200
atgcctggag acagatacgt agttgtgctt ttgtttgctc ttttaagcag tctcactgca    4260
gtcttatttc caagtaagag tactgggaga atcactaggt aacttattag aaacccaaat    4320
tgggacaaca gtgctttgta aattgtgttg tcttcagcag tcaatacaaa tagatttttg    4380
```

-continued

```
tttttgttgt tcctgcagcc ccagaagaaa ttaggggtta aagcagacag tcacactggt   4440
ttggtcagtt acaaagtaat ttctttgatc tggacagaac atttatatca gtttcatgaa   4500
atgattggaa tattacaata ccgttaagat acagtgtagg catttaactc ctcattggcg   4560
tggtccatgc tgatgatttt gcaaaatgag ttgtgatgaa tcaatgaaaa atgtaattta   4620
gaaactgatt tcttcagaat tagatggctt attttttaaa atatttgaat gaaaacattt   4680 tattttttaaa atattacaca ggaggcttcg gagtttctta gtcattactg tccttttccc   4740
ctacagaatt ttccctcttg gtgtgattgc acagaatttg tatgtatttt cagttacaag   4800
attgtaagta aattgcctga tttgtttttca ttatagacaa cgatgaattt cttctaatta   4860
tttaaataaa atcaccaaaa acataaacat tttattgtat gcctgattaa gtagttaatt   4920
atagtctaag gcagtactag agttgaacca aaatgatttg tcaagcttgc tgatgtttct   4980 gttttttcgtt tttttttttt ttccggagag aggataggat ctcactctgt tatccaggct   5040
ggagtgtgca atggcacaat catagctcag tgcagcctca aactcctggg ctcaagcaat   5100
cctcctgcct cagcctcccg agtaactagg accacaggca caggccacca tgcctggcta   5160
aggtttttat ttttattttt tgtagacatg gggatcacac aatgttgccc aggctggtct   5220
tgaactcctg gcctcaagca aggtcgtgct ggtaatttg caaaatgaat tgtgattgac   5280
tttcagcctc ccaacgtatt agattatagg cattagccat ggtgcccagc cttgtaactt   5340 ttaaaaaaaat ttttttaatct acaactctgt agattaaaat ttcacatggt gttctaatta   5400
aatatttttc ttgcagccaa gatattgtta ctacagataa cacaacctga tatggtaact   5460
ttaaattttg ggggctttga atcattcagt ttatgcatta actagtccct ttgtttatct   5520
ttcatttctc aacccccttgt actttggtga taccagacat cagaataaaa agaaattgaa   5580
gtacctgttt tcaaatggat actttatagg aattttggta aagatttggt gatgggagga   5640
tgacttgagg tttgtggata ttagttaatt attcagtatg atacctcacc cagctaattt   5700
```

<210> SEQ ID NO 6
<211> LENGTH: 1207
<212> TYPE: PRT
<213> ORGANISM: Artificial
<220> FEATURE:
<223> OTHER INFORMATION: Synthetic

<400> SEQUENCE: 6

```
Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125
```

-continued

```
Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
                180                 185                 190

Lys Ala Leu Leu Glu Thr Ser Glu Lys Ile Thr Ala Val Ser Leu Asp
            195                 200                 205

Val Leu Asp Lys Arg Leu Phe Trp Ile Gln Tyr Asn Arg Glu Gly Ser
    210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
                260                 265                 270

Asn Lys His Thr Gly Lys Asp Met Val Arg Ile Asn Leu His Ser Ser
            275                 280                 285

Phe Val Pro Leu Gly Glu Leu Lys Val Val His Pro Leu Ala Gln Pro
    290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
                340                 345                 350

Tyr Cys Glu Asp Val Asn Glu Cys Ala Phe Trp Asn His Gly Cys Thr
            355                 360                 365

Leu Gly Cys Lys Asn Thr Pro Gly Ser Tyr Tyr Cys Thr Cys Pro Val
    370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
            435                 440                 445

Gln Leu Cys Val Pro Leu Ser Pro Val Ser Trp Glu Cys Asp Cys Phe
    450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
                500                 505                 510

Met Val Tyr Ala Leu Asp His Asp Pro Val Glu Asn Lys Ile Tyr Phe
            515                 520                 525

Ala His Thr Ala Leu Lys Trp Ile Glu Arg Ala Asn Met Asp Gly Ser
    530                 535                 540

Gln Arg Glu Arg Leu Ile Glu Glu Gly Val Asp Val Pro Glu Gly Leu
```

```
545                   550                   555                   560

Ala Val Asp Trp Ile Gly Arg Arg Phe Tyr Trp Thr Asp Arg Gly Lys
                565                   570                   575

Ser Leu Ile Gly Arg Ser Asp Leu Asn Gly Lys Arg Ser Lys Ile Ile
                580                   585                   590

Thr Lys Glu Asn Ile Ser Gln Pro Arg Gly Ile Ala Val His Pro Met
                595                   600                   605

Ala Lys Arg Leu Phe Trp Thr Asp Thr Gly Ile Asn Pro Arg Ile Glu
        610                   615                   620

Ser Ser Ser Leu Gln Gly Leu Gly Arg Leu Val Ile Ala Ser Ser Asp
625                   630                   635                   640

Leu Ile Trp Pro Ser Gly Ile Thr Ile Asp Phe Leu Thr Asp Lys Leu
                645                   650                   655

Tyr Trp Cys Asp Ala Lys Gln Ser Val Ile Glu Met Ala Asn Leu Asp
                660                   665                   670

Gly Ser Lys Arg Arg Arg Leu Thr Gln Asn Asp Val Gly His Pro Phe
                675                   680                   685

Ala Val Ala Val Phe Glu Asp Tyr Val Trp Phe Ser Asp Trp Ala Met
        690                   695                   700

Pro Ser Val Met Arg Val Asn Lys Arg Thr Gly Lys Asp Arg Val Arg
705                   710                   715                   720

Leu Gln Gly Ser Met Leu Lys Pro Ser Ser Leu Val Val Val His Pro
                725                   730                   735

Leu Ala Lys Pro Gly Ala Asp Pro Cys Leu Tyr Gln Asn Gly Gly Cys
                740                   745                   750

Glu His Ile Cys Lys Lys Arg Leu Gly Thr Ala Trp Cys Ser Cys Arg
                755                   760                   765

Glu Gly Phe Met Lys Ala Ser Asp Gly Lys Thr Cys Leu Ala Leu Asp
        770                   775                   780

Gly His Gln Leu Leu Ala Gly Gly Glu Val Asp Leu Lys Asn Gln Val
785                   790                   795                   800

Thr Pro Leu Asp Ile Leu Ser Lys Thr Arg Val Ser Glu Asp Asn Ile
                805                   810                   815

Thr Glu Ser Gln His Met Leu Val Ala Glu Ile Met Val Ser Asp Gln
                820                   825                   830

Asp Asp Cys Ala Pro Val Gly Cys Ser Met Tyr Ala Arg Cys Ile Ser
                835                   840                   845

Glu Gly Glu Asp Ala Thr Cys Gln Cys Leu Lys Gly Phe Ala Gly Asp
        850                   855                   860

Gly Lys Leu Cys Ser Asp Ile Asp Glu Cys Glu Met Gly Val Pro Val
865                   870                   875                   880

Cys Pro Pro Ala Ser Ser Lys Cys Ile Asn Thr Glu Gly Gly Tyr Val
                885                   890                   895

Cys Arg Cys Ser Glu Gly Tyr Gln Gly Asp Gly Ile His Cys Leu Asp
                900                   905                   910

Ile Asp Glu Cys Gln Leu Gly Glu His Ser Cys Gly Glu Asn Ala Ser
                915                   920                   925

Cys Thr Asn Thr Glu Gly Gly Tyr Thr Cys Met Cys Ala Gly Arg Leu
        930                   935                   940

Ser Glu Pro Gly Leu Ile Cys Pro Asp Ser Thr Pro Pro His Leu
945                   950                   955                   960

Arg Glu Asp Asp His His Tyr Ser Val Arg Asn Ser Asp Ser Glu Cys
                965                   970                   975
```

-continued

```
Pro Leu Ser His Asp Gly Tyr Cys Leu His Asp Gly Val Cys Met Tyr
            980                 985                 990

Ile Glu Ala Leu Asp Lys Tyr Ala  Cys Asn Cys Val Val  Gly Tyr Ile
            995                1000                1005

Gly Glu Arg Cys Gln Tyr Arg  Asp Leu Lys Trp Trp  Glu Leu Arg
    1010        Cys         1015            1020

His Ala  Gly His Gly Gln Gln  Gln Lys Val Ile Val  Val Ala Val
    1025                1030                1035

Cys Val  Val Val Leu Val Met  Leu Leu Leu Leu Ser  Leu Trp Gly
    1040                1045                1050

Ala His  Tyr Tyr Arg Thr Gln  Lys Leu Leu Ser Lys  Asn Pro Lys
    1055                1060                1065

Asn Pro  Tyr Glu Glu Ser Ser  Arg Asp Val Arg Ser  Arg Arg Pro
    1070                1075                1080

Ala Asp  Thr Glu Asp Gly Met  Ser Ser Cys Pro Gln  Pro Trp Phe
    1085                1090                1095

Val Val  Ile Lys Glu His Gln  Asp Leu Lys Asn Gly  Gly Gln Pro
    1100                1105                1110

Val Ala  Gly Glu Asp Gly Gln  Ala Ala Asp Gly Ser  Met Gln Pro
    1115                1120                1125

Thr Ser  Trp Arg Gln Glu Pro  Gln Leu Cys Gly Met  Gly Thr Glu
    1130                1135                1140

Gln Gly  Cys Trp Ile Pro Val  Ser Ser Asp Lys Gly  Ser Cys Pro
    1145                1150                1155

Gln Val  Met Glu Arg Ser Phe  His Met Pro Ser Tyr  Gly Thr Gln
    1160                1165                1170

Thr Leu  Glu Gly Gly Val Glu  Lys Pro His Ser Leu  Leu Ser Ala
    1175                1180                1185

Asn Pro  Leu Trp Gln Gln Arg  Ala Leu Asp Pro Pro  His Gln Met
    1190                1195                1200

Glu Leu  Thr Gln
    1205
```

```
<210> SEQ ID NO 7
<211> LENGTH: 53
<212> TYPE: PRT
<213> ORGANISM: Artificial
<220> FEATURE:
<223> OTHER INFORMATION: Synthetic

<400> SEQUENCE: 7

Asn Thr Glu Asn Asp Cys Pro Leu Ser His Glu Ala Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Val Gly Glu Arg Cys Gln Phe Arg Asp Leu Arg
        35                  40                  45

Trp Trp Asp Ala Arg
    50
```

```
<210> SEQ ID NO 8
<211> LENGTH: 53
<212> TYPE: PRT
<213> ORGANISM: Artificial
<220> FEATURE:
<223> OTHER INFORMATION: Synthetic
```

-continued

```
<400> SEQUENCE: 8

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 9
<211> LENGTH: 4
<212> TYPE: PRT
<213> ORGANISM: Artificial
<220> FEATURE:
<223> OTHER INFORMATION: Synthetic

<400> SEQUENCE: 9

Gly Ser Ser Gly
1

<210> SEQ ID NO 10
<211> LENGTH: 5
<212> TYPE: PRT
<213> ORGANISM: Artificial
<220> FEATURE:
<223> OTHER INFORMATION: Synthetic

<400> SEQUENCE: 10

Ser Ser Gly Gly Gly
1               5

<210> SEQ ID NO 11
<211> LENGTH: 5
<212> TYPE: PRT
<213> ORGANISM: Artificial
<220> FEATURE:
<223> OTHER INFORMATION: Synthetic

<400> SEQUENCE: 11

Gly Gly Ser Gly Gly
1               5

<210> SEQ ID NO 12
<211> LENGTH: 5
<212> TYPE: PRT
<213> ORGANISM: Artificial
<220> FEATURE:
<223> OTHER INFORMATION: Synthetic

<400> SEQUENCE: 12

Gly Gly Gly Gly Ser
1               5

<210> SEQ ID NO 13
<211> LENGTH: 8
<212> TYPE: PRT
<213> ORGANISM: Artificial
<220> FEATURE:
<223> OTHER INFORMATION: Synthetic

<400> SEQUENCE: 13

Ser Ser Gly Gly Gly Ser Gly Gly
1               5
```

-continued

```
<210> SEQ ID NO 14
<211> LENGTH: 10
<212> TYPE: PRT
<213> ORGANISM: Artificial
<220> FEATURE:
<223> OTHER INFORMATION: Synthetic

<400> SEQUENCE: 14

Ser Ser Gly Gly Gly Gly Ser Gly Gly Gly
1               5                   10

<210> SEQ ID NO 15
<211> LENGTH: 7
<212> TYPE: PRT
<213> ORGANISM: Artificial
<220> FEATURE:
<223> OTHER INFORMATION: Synthetic

<400> SEQUENCE: 15

Thr Ser Gly Gly Gly Ser Gly
1               5

<210> SEQ ID NO 16
<211> LENGTH: 9
<212> TYPE: PRT
<213> ORGANISM: Artificial
<220> FEATURE:
<223> OTHER INFORMATION: Synthetic

<400> SEQUENCE: 16

Thr Ser Gly Gly Gly Gly Ser Gly Gly
1               5

<210> SEQ ID NO 17
<211> LENGTH: 10
<212> TYPE: PRT
<213> ORGANISM: Artificial
<220> FEATURE:
<223> OTHER INFORMATION: Synthetic

<400> SEQUENCE: 17

Ser Ser Gly Gly Ser Gly Gly Gly Ser Gly
1               5                   10

<210> SEQ ID NO 18
<211> LENGTH: 11
<212> TYPE: PRT
<213> ORGANISM: Artificial
<220> FEATURE:
<223> OTHER INFORMATION: Synthetic

<400> SEQUENCE: 18

Ser Ser Gly Gly Gly Ser Gly Gly Ser Ser Gly
1               5                   10

<210> SEQ ID NO 19
<211> LENGTH: 12
<212> TYPE: PRT
<213> ORGANISM: Artificial
<220> FEATURE:
<223> OTHER INFORMATION: Synthetic

<400> SEQUENCE: 19

Gly Gly Ser Gly Gly Thr Ser Gly Gly Gly Ser Gly
1               5                   10
```

-continued

```
<210> SEQ ID NO 20
<211> LENGTH: 12
<212> TYPE: PRT
<213> ORGANISM: Artificial
<220> FEATURE:
<223> OTHER INFORMATION: Synthetic

<400> SEQUENCE: 20

Ser Gly Gly Thr Ser Gly Gly Gly Ser Gly Gly
1               5                   10

<210> SEQ ID NO 21
<211> LENGTH: 14
<212> TYPE: PRT
<213> ORGANISM: Artificial
<220> FEATURE:
<223> OTHER INFORMATION: Synthetic

<400> SEQUENCE: 21

Gly Gly Ser Gly Gly Thr Ser Gly Gly Gly Gly Ser Gly Gly
1               5                   10

<210> SEQ ID NO 22
<211> LENGTH: 13
<212> TYPE: PRT
<213> ORGANISM: Artificial
<220> FEATURE:
<223> OTHER INFORMATION: Synthetic

<400> SEQUENCE: 22

Ser Ser Gly Gly Gly Gly Ser Gly Gly Gly Ser Ser Gly
1               5                   10

<210> SEQ ID NO 23
<211> LENGTH: 13
<212> TYPE: PRT
<213> ORGANISM: Artificial
<220> FEATURE:
<223> OTHER INFORMATION: Synthetic

<400> SEQUENCE: 23

Ser Ser Gly Gly Gly Ser Gly Gly Ser Ser Gly Gly Gly
1               5                   10

<210> SEQ ID NO 24
<211> LENGTH: 15
<212> TYPE: PRT
<213> ORGANISM: Artificial
<220> FEATURE:
<223> OTHER INFORMATION: Synthetic

<400> SEQUENCE: 24

Ser Ser Gly Gly Gly Gly Ser Gly Gly Gly Ser Ser Gly Gly Gly
1               5                   10                  15

<210> SEQ ID NO 25
<211> LENGTH: 103
<212> TYPE: PRT
<213> ORGANISM: Artificial
<220> FEATURE:
<223> OTHER INFORMATION: Synthetic

<400> SEQUENCE: 25

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
                20                  25                  30
```

-continued

```
Asp Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100
```

METHODS AND COMPOSITIONS FOR USE OF GROWTH FACTOR ANTIBODIES IN COMBINATION WITH NON-TYROSINE TARGETING KINASE INHIBITORS

CROSS REFERENCE TO RELATED APPLICATIONS

This application is a national stage filed under 35 U.S.C. § 371, of international application No. PCT/IB2020/000969, filed Nov. 6, 2020, which claims priority to U.S. Provisional Application Ser. No. 62/932,131, filed Nov. 7, 2019, entitled "COMPOSITIONS AND METHODS FOR USE OF ANTI-EGF ANTIBODIES WITH MEK INHIBITORS," and U.S. Provisional Application Ser. No. 63/094,018 filed Oct. 20, 2020, entitled "ANTI-EPIDERMAL GROWTH FACTOR VACCINE ANTIBODIES INCREASE THE ANTITUMOR ACTIVITY OF KINASE INHIBITORS IN NON SMALL CELL LUNG CANCER CELL LINES," which are incorporated by reference herein in their entirety for all purposes.

FIELD OF THE DISCLOSURE

The disclosure relates to methods for treating cancer. More particularly, the disclosure relates to use of chimeric non-natural synthetic proteins, in combination with non-tyrosine targeting kinase inhibitors (NTKIs), in treating cancer and preventing intrinsic and/or acquired resistance to NTKIs.

BACKGROUND OF THE DISCLOSURE

According to the World Health Organization, neoplasia (e.g., cancer) is one of the leading causes of death worldwide and was responsible for 8.8 million deaths in 2015. The frequency of cancer in the global human population is significant: accounting for nearly 1 in 6 deaths. In 2015, the most common cancer deaths occurred from the following types of cancer: lung cancer (about 1.7 million deaths), liver cancer (about 800,000 deaths), colorectal cancer (about 800,000 deaths), stomach cancer (about 800,000 deaths), and breast cancer (about 600,000 deaths).

Most chemotherapeutic agents act on a specific molecular target thought to be involved in the development of the malignant phenotype. However, a complex network of signaling pathways regulates cell proliferation and the majority of malignant cancers are facilitated by multiple genetic abnormalities in these pathways. Although treatment of cancers with standard cytotoxic chemotherapies has been optimized for efficacy, more recent approaches are based on classification into molecular subsets based on their distinct oncogene driver. These molecular drivers of cancer can be attacked therapeutically with targeted agents directed against the specific oncogenes.

A promising set of targets for therapeutic intervention in the treatment of cancer includes the members of the HER-kinase axis and their downstream effectors. They frequently exhibit mutations in solid epithelial tumors of, by way of example, the prostate, lung, and breast, and are also up-regulated in glioblastoma tumors. Patients with wild type EGFR effector proteins—for example, RAS, BRAF, and PIK3CA—can be treated with tyrosine kinase inhibitors (TKIs) targeting EGFR such as Cetuximab and Erlotinib. However, there is a large cohort of cancer patients harboring mutations in EGFR effector proteins. Extant treatments are not effective for these patients because the mutations provide resistance to the TKIs targeting EGFR and enable the development of resistance to the non-tyrosine targeting kinase inhibitors (NTKIs) targeting EGFR effectors. Similarly, treatment with TKIs targeting EGFR in patients with wild type EGFR effector proteins often results in the development of resistance due to the selection for oncogenic mutations. Thus, although the extant treatments with TKIs and NTKIs exhibit strong anti-tumor properties targeting the EGFR pathway in some patients, they become less potent or entirely ineffective in patients who develop resistance. EGFR effector kinases may be referred to as 'bypass pathways', in that they have been identified as mechanisms of both intrinsic and acquired resistance to TKIs and NTKIs. Without being bound by theory, it is thought that parallel or other kinases in the EGFR signaling cascade compensate for mutated kinases, thereby inducing stronger EGFR signaling effects. Therefore, there is a need for additional therapies to overcome EGFR pathway resistance to non-tyrosine targeting kinase inhibitors in order to effectively treat EGFR or similar growth factor mediated diseases and cancers.

SUMMARY OF THE DISCLOSURE

The present disclosure is directed towards the use of chimeric non-natural synthetic proteins in combination with EGFR effector non-tyrosine targeting kinase inhibitors to prevent or minimize resistance to non-tyrosine targeting kinase inhibitors (NTKIs), thereby inhibiting cell growth. These therapies can be used to treat cancer, such as, for example, lung cancer, breast cancer, bladder cancer, prostate cancer, ovarian cancer, vulva cancer, colonic cancer, colorectal cancer, intestinal cancer, pulmonary cancer, brain cancer, esophageal cancer, and other cancers.

In an illustrative embodiment, the present disclosure provides a method of treating cancer in a subject, comprising administering to the subject an active regimen of a non-tyrosine targeting kinase inhibitor (NTKI) and a non-natural synthetic polypeptide (NNSP), comprising a full length, or fragment thereof, of a growth factor or growth factor receptor, an immunogenic polypeptide, and a linker, wherein the polypeptide is separated from the immunogenic polypeptide by the linker.

In some embodiments, the method of treating cancer in a subject comprises administering to the subject an active regimen of a non-tyrosine targeting kinase inhibitor (NTKI) and an antibody directed to a growth factor or growth factor receptor.

In other embodiments, a method of treating non-small cell lung carcinoma (NSCLC) or colorectal cancer (CRC) in a subject is disclosed, comprising administering to the subject a non-tyrosine targeting kinase inhibitor (NTKI) and a non-natural synthetic polypeptide (NNSP), comprising a full length, or fragment thereof, of a growth factor or growth factor receptor, an immunogenic polypeptide, and a linker, wherein the polypeptide is separated from the immunogenic polypeptide by the linker.

In some embodiments, a method of treating non-small cell lung carcinoma (NSCLC) or colorectal cancer (CRC) in a subject is disclosed, comprising administering to the subject a non-tyrosine targeting kinase inhibitor (NTKI) and an antibody directed to a growth factor or growth factor receptor.

In some embodiments, the growth factor is EGF.

In some embodiments, the growth factor receptor is EGFR.

In further embodiments, the immunogenic polypeptide comprises a full length, or portion thereof, of a cholera toxin B (CT-B) protein.

In some embodiments, the NNSP comprises SEQ ID NO: 7 or SEQ ID NO: 8, or wherein the NNSP is derived from a cell that expresses SEQ ID NO: 7 or SEQ ID NO: 8.

In some embodiments, the NNSP comprises SEQ ID NO: 2 or SEQ ID NO: 6, or wherein the NNSP is derived from a cell expressing SEQ ID NO: 2 or SEQ ID NO: 6.

In some embodiments, the antibody is derived from a hybridoma cell.

In some embodiments, the NTKI is Trametinib, Taselisib, Alpelisib, Copanlisib, Idealisib, Duvelisib, Buparlisib, Umbralisib, PX-866, Dactolisib, CUDC-907, Voxtalisib (SAR245409, XL765) ME-401, IPI-549, SF1126, INK1117 Pictilisib, XL147 (SAR245408), GSK1059615, ZSTK474, PWT33597, IC87114, TG100-115, CAL 263, RP6503, GNE-477 AEZS-136, Encorafenib, Vemurafenib, Dabrafenib, GDC-0879, PLX-4720, Cobimetinib, Binimetinib, Selumetinib, PD-325901, PD035901, CI-1040, TAK-733, Perifosine, Palomid 529 or pharmaceutically acceptable salts thereof.

In some embodiments, the EGF is human EGF or murine EGF.

In some embodiments, the linker is selected from the group consisting of SSG, GSSG (SEQ ID NO: 9), SSGGG (SEQ ID NO: 10), SGG, GGSGG (SEQ ID NO: 11), GGGGS (SEQ ID NO: 12), SSGGGSGG (SEQ ID NO: 13), SSGGGGSGGG (SEQ ID NO: 14), TSGGGSG (SEQ ID NO: 15), TSGGGGSGG (SEQ ID NO: 16), SSGGGSGGGSG (SEQ ID NO: 17), SSGGGSGGSSG (SEQ ID NO: 18), GGSGGTSGGGSG (SEQ ID NO: 19), SGGTSGGGGSGG (SEQ ID NO: 20), GGSGGTSGGGGSGG (SEQ ID NO: 21), SSGGGGSGGGSSG (SEQ ID NO: 22), SSGGGSGGSSGGG (SEQ ID NO: 23), and SSGGGGSGGGSSGGG (SEQ ID NO: 24).

In some embodiments, the linker is GSSG (SEQ ID NO: 9) or GGSGGTSGGGGSGG (SEQ ID NO: 21).

In some embodiments, the NNSP includes a full length, or fragment thereof, of at least two different growth factors or two different growth factor receptors.

In some embodiments, the active regimen is administered to the subject according to a therapeutically effective amount repeated thrice, twice or once a week, once in two weeks, once in three weeks or at least once monthly, in combination with the administration of a NTKI in a continuous regimen based on an average daily dose in the range of 10 to 400 mg, wherein the method prevents acquiring resistance to the NTKI treatment.

In some embodiments, the average daily dose is selected from the group consisting of 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, and 400 mg.

In some embodiments, the active regimen is administered to the subject according to a therapeutically effective amount repeated thrice, twice or once a week, once in two weeks, once in three weeks or at least once monthly, prior to administration of a NTKI in a continuous regimen based on an average daily dose in the range of 10 to 400 mg, wherein the method prevents acquiring resistance to the NTKI treatment.

In some embodiments, the active regimen is administered to the subject according to a therapeutically effective amount repeated thrice, twice or once a week, once in two weeks, once in three weeks or at least once monthly, after administration of a NTKI in a continuous regimen based on an average daily dose in the range of 10 to 400 mg, wherein the method prevents acquiring resistance to the NTKI treatment.

In some embodiments, the NNSP produces pathway immunization that results in inhibition of an EGF/EGFR pathway.

In some embodiments, the antibody produces pathway immunization that results in inhibition of an EGF/EGFR pathway.

In some embodiments, the subject expresses mutated forms of HRAS, NRAS, KRAS, PIK3CA, BRAF, and/or MEK proteins.

In some embodiments, the NTKI targets HRAS, NRAS, KRAS, PIK3CA, BRAF, and/or MEK proteins.

In some embodiments, the subject has acquired resistance to NTKI treatment and the method overcomes resistance to NTKI treatment.

In some embodiments, the cancer is associated with a mutant form of HRAS, NRAS, KRAS, PIK3CA, BRAF, and/or MEK proteins.

In some embodiments, the method of treating cancer in a subject further comprises obtaining a tissue sample from the subject; identifying one or more mutations in the tissue sample from the subject; and conducting the administering steps if the one or more mutations are identified as being in one or more growth factor receptor effector proteins.

In some embodiments the one or more effector proteins is HRAS, NRAS, KRAS, PIK3CA, BRAF, and/or MEK proteins.

In some embodiments the one or more mutations is selected from the following: KRAS G12S, KRAS G12C, KRAS G13D, KRAS G12D, EML4-ALK (V3; E6:A20), BRAF V600E, BRAF G596R, PIK3CA E545K, and NRAS Q61K.

In some embodiments the EGF is human EGF or murine EGF.

In some embodiments the antibody is administered at about 0.01-0.1 µg/kg to about 95 mg/kg body weight; or from about 0.1-1.0 µg/kg to about 90 mg/kg body weight; or from about 0.5-5.0 µg/kg to about 80 mg/kg body weight; or from about 1.0-10.0 µg/kg to about 60 mg/kg body weight; or from about 5.0-20.0 µg/kg to about 50 mg/kg body weight; or from about 20-50 µg/kg to about 25 mg/kg body weight; or from about 50-100 µg/kg to about 20 mg/kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 µg/kg body weight.

Definitions

By "ameliorate" is meant decrease, suppress, attenuate, diminish, arrest, or stabilize the development or progression of a disease.

By "disease" is meant any condition or disorder that damages or interferes with the normal function of a cell, tissue, or organ.

By "BVN22E nucleic acid molecule," also known as "IN01," is meant a polynucleotide encoding a BVN22E polypeptide. An exemplary BVN22E nucleic acid molecule is reproduced below (SEQ ID NO: 1):

```
>BVN22E
aataccgaaaacgattgccctctgtctcatgaagc gtattgtctgcacgacggcgtgtgtatgtacattg aagccctggacaaatatgcatgtaactgtgtcgtg ggctacgtgggggagcgatgtcagtttcgagacct gcgttggtgggatgcgcgcggctcgagcggtaata ccgaaaacgattgccctctgtctcatgaagcgtat tgtctgcacgacggcgtgtgtatgtacattgaagc cctggacaaatatgcatgtaactgtgtcgtgggct acgtgggggagcgatgtcagtttcgagacctgcgt tggtgggatgcgcgcggcgggtctggaggtactag tggcggcggtggagggtcgggtaccccgcagaaca tcaccgacctgtgcgccgagtaccacaacacccag atccacaccctgaacgacaagatcttctcgtacac cgagagcctggccgataagcgtgaaatggccatca tcaccttcaagaacggtgcgaccttccaggtggag gtcccgggtagccagcacatcgattcacagaagaa ggccatcgagcgtatgaaggacaccctgcgtatcg cctacctgaccgaagccaaggtggaaaagctgtgc gtctggaacaacaagacgccgcacgccatcgccgc catcagcatggccaat
```

By "BVN22E polypeptide," also known as "IN01," is meant a polypeptide or fragment thereof having at least about 85%, 90%, 91%, 92%, 93%, 94%, 95%, 96%, 97%, 98%, or 99% amino acid identity (excluding the following amino acid changes: T2S, E3D, N4S, D5E, E11D, A12G, V38I, F44Y, R48K, D51E, and A52L) to the amino acid sequence below (SEQ ID NO: 2):

```
>BVN22E
NTENDCPLSHEAYCLHDGVCMYIEALDKYACNCVVG

YVGERCQFRDLRWWDARGSSGNTENDCPLSHEAYC

LHDGVCMYIEALDKYACNCVVGYVGERCQFRDLRW

WDARGGSGGTSGGGGGSGTPQNITDLCAEYHNTQI

HTLNDKIFSYTESLADKREMAIITFKNGATFQVEV

PGSQHIDSQKKAIERMKDTLRIAYLTEAKVEKLCV

WNNKTPHAIAAISMAN
```

By "Epidermal Growth Factor Receptor (EGFR) nucleic acid molecule" is meant a polynucleotide encoding an EGFR polypeptide. An exemplary EGFR nucleic acid molecule is provided at NCBI Accession No. NM_005228.4, and reproduced below (SEQ ID NO: 3):

```
>NM_005228.4
gtccgggcagcccccggcgcagcgcggccgcagca gcctccgccccccgcacggtgtgagcgcccgacgc
```

```
-continued
ggccgaggcggccggagtcccgagctagccccggc ggccgccgccgcccagaccggacgacaggccacct cgtcggcgtccgcccgagtccccgcctcgccgcca acgccacaaccaccgcgcacggccccctgactccg tccagtattgatcgggagagccggagcgagctctt cggggagcagcgacgcgaccctccgggacggccgg ggcagcgctcctggcgctgctggctgcgctctgcc cggcgagtcgggctctggaggaaaagaaagtttgc caaggcacgagtaacaagctcacgcagttgggcac ttttgaagatcattttctcagcctccagaggatgt tcaataactgtgaggtggtccttgggaatttggaa attacctatgtgcagaggaattatgatctttcctt cttaaagaccatccaggaggtggctggttatgtcc tcattgccctcaacacagtggagcgaattcctttg gaaaacctgcagatcatcagaggaaatatgtacta cgaaaattcctatgccttagcagtcttatctaact atgatgcaaataaaaccggactgaaggagctgccc atgagaaatttacaggaaatcctgcatggcgccgt gcggttcagcaacaaccctgccctgtgcaacgtgg agagcatccagtggcgggacatagtcagcagtgac tttctcagcaacatgtcgatggacttccagaacca cctgggcagctgccaaaagtgtgatccaagctgtc ccaatgggagctgctggggtgcaggagaggagaac tgccagaaactgaccaaaatcatctgtgcccagca gtgctccgggcgctgccgtggcaagtcccccagtg actgctgccacaaccagtgtgctgcaggctgcaca ggccccgggagagcgactgcctggtctgccgcaa attccgagacgaagccacgtgcaaggacacctgcc ccccactcatgctctacaaccccaccacgtaccag atggatgtgaaccccgagggcaaatacagctttgg tgccacctgcgtgaagaagtgtccccgtaattatg tggtgacagatcacggctcgtgcgtccgagcctgt ggggccgacagctatgagatggaggaagacggcgt ccgcaagtgtaagaagtgcgaagggccttgccgca aagtgtgtaacggaataggtattggtgaatttaaa gactcactctccataaatgctacgaatattaaaca cttcaaaaactgcacctccatcagtggcgatctcc acatcctgccggtggcatttagggggtgactccttc acacatactcctcctctggatccacaggaactgga tattctgaaaaccgtaaaggaaatcacagggtttt tgctgattcaggcttggcctgaaaacaggacggac
```

-continued ctccatgcctttgagaacctagaaatcatacgcgg caggaccaagcaacatggtcagttttctcttgcaa tcgtcagcctgaacataacatccttgggattacgc tccctcaaggagataagtgatggagatgtgataat ttcaggaaacaaaaatttgtgctatgcaaatacaa taaactggaaaaaactgtttgggacctccggtcag aaaaccaaaattataagcaacagaggtgaaaacag ctgcaaggccacaggccaggtctgccatgccttgt gctcccccgagggctgctggggcccggagcccagg gactgcgtctcttgccggaatgtcagccgaggcag ggaatgcgtggacaagtgcaaccttctggagggtg agccaagggagtttgtggagaactctgagtgcata cagtgccacccagagtgcctgcctcaggccatgaa catcacctgcacaggacggggaccagacaactgta tccagtgtgcccactacattgacggcccccactgc gtcaagacctgcccggcaggagtcatgggagaaaa caacaccctggtctggaagtacgcagacgccggcc atgtgtgccacctgtgccatccaaactgcacctac ggatgcactgggccaggtcttgaaggctgtccaac gaatgggcctaagatcccgtccatcgccactggga tggtggggggccctcctcttgctgctggtggtggcc ctggggatcggcctcttcatgcgaaggcgccacat cgttcggaagcgcacgctgcggaggctgctgcagg agagggagcttgtggagcctcttacacccagtgga gaagctcccaaccaagctctcttgaggatcttgaa ggaaactgaattcaaaaagatcaaagtgctgggct ccggtgcgttcggcacggtgtataagggactctgg atcccagaaggtgagaaagttaaaattcccgtcgc tatcaaggaattaagagaagcaacatctccgaaag ccaacaaggaaatcctcgatgaagcctacgtgatg gccagcgtggacaaccccacgtgtgccgcctgct gggcatctgcctcacctccaccgtgcagctcatca cgcagctcatgcccttcggctgcctcctggactat gtccgggaacacaaagacaatattggctcccagta cctgctcaactggtgtgtgcagatcgcaaagggca tgaactacttggaggaccgtcgcttggtgcaccgc gacctggcaaccaggaacgtactggtgaaaacacc gcagcatgtcaagatcacagattttgggctggcca aactgctgggtgcggaagagaaagaataccatgca gaaggaggcaaagtgcctatcaagtggatggcatt -continued ggaatcaattttacacagaatctatacccaccaga gtgatgtctggagctacggggtgactgtttgggag ttgatgscctttggatccaagccatatgacggaat ccctgccagcgagatctcctccatcctggagaaag gagaacgcctccctcagccacccatatgtaccatc gatgtctacatgatcatggtcaagtgctggatgat agacgcagatagtcgcccaaagttccgtgagttga tcarcgaattctccaaaatggcccgagaccccag cgctaccttgtcattcaggggatgaaagaatgca tttgccaagtcctacagactccaacttctaccgtg ccctgatggatgaagaagacatggacgacgtggtg gatgccgacgagtacctcatcccacaacagggctt cttcagcagccctccacgtcacggactcccctcc tgagctctctgagtgcaaccagcaacaattccacc gtggcttgcattgatagaaatgggctgcaaagctg tcccatcaaggaagacagcttcttgcagcgataca gctcagacccacaggcgccttgactgaggacaac atagacgacaccttcctcccagtgcctgaatacat aaaccagtccgttcccaaaaggcccgctggctctg tgcagaatcctgtctatcacaatcagcctctgaac cccgcgcccagcagagacccacactaccaggaccc ccacagcactgcagtgggcaaccccgagtatctca acactgtccagcccacctgtgtcaacagcacattc gacagccctgcccactgggcccagaaaggcagcca ccaaattagcctggacaaccctgactaccagcagg acttctttcccaaggaagccaagccaaatggcatc tttaagggctccacagctgaaaatgcagaatacct aagggtcgcgccacaaagcagtgaatttattggag catgaccacggaggatagtatgagccctaaaaatc cagactctttcgatacccaggaccaagccacagca ggtcctccatcccaacagccatgcccgcattagct cttagacccacagactggttttgcaacgtttacac cgactagccaggaagtacttccacctcgggcacat tttgggaagttgcattcctttgtcttcaaactgtg aagcatttacagaaacgcatccagcaagaatattg tcccttcgagcagaaatttatctttcaaagaggta tatttgaaaaaaaaaaaaagtatatgtgaggattt ttattgattggggatcttggagttttttcattgtcg ctattgatttttacttcaatgggctcttccaacaa ggaagaagcttgctggtagcacttgctaccctgag ttcatccaggcccaactgtgagcaaggagcacaag -continued ccacaagtcttccagaggatgcttgattccagtgg ttctgcttcaaggcttccactgcaaaacactaaag atccaagaaggccttcatggccccagcaggccgga tcggtactgtatcaagtcatggcaggtacagtagg ataagccactctgtcccttcctgggcaaagaagaa acggaggggatggaattcttccttagacttacttt tgtaaaaatgtccccacggtacttactccccactg atggaccagtggtttccagtcatgagcgttagact gacttgtttgtcttccattccattgttttgaaact cagtatgctgccctgtcttgctgtcatgaaatca gcaagagaggatgacacatcaaataataactcgga ttccagcccacattggattcatcagcatttggacc aatagcccacagctgagaatgtggaatacctaagg atagcaccgcttttgttctcgcaaaaacgtatctc ctaatttgaggctcagatgaaatgcatcaggtcct ttgggcatagatcagaagactacaaaaatgaagc tgctctgaaatctcctttagccatcaccccaaccc cccaaaattagtttgtgttacttatggaagatagt tttctccttttacttcacttcaaaagcttttact caaagagtatatgttccctccaggtcagctgcccc caaaccccctccttacgctttgtcacacaaaagt gtctctgccttgagtcatctattcaagcacttaca gctctggccacaacagggcattttacaggtgcgaa tgacagtagcattatgagtagtgtggaattcaggt agtaaatatgaaactagggtttgaaattgataatg ctttcacaacatttgcagatgtrttagaaggaaaa aagttccttcctaaaataatttctctacaattgga agattggaagattcagctagttaggagcccacctt ttttcctaatctgtgtgtgccctgtaacctgactg attaacagcagtcctttgtaaacagtgttttaaac tctcctagtcaatatccaccccatccaatttatca aggaagaaatggttcagaaaatattttcagcctac agttatgttcagtcacacacacatacaaaatgttc ctttttgcttttaaagtaattttttgactcccagatc agtcagagcccctacagcattgttaagaaagtatt tgattttgtctcaatgaaaataaaactatattca tttccactctattatgctctcaaatacccctaagc atctatactagcctggtatgggtatgaaagataca aagataaataaaacatagtccctgattctaagaaa ttcacaatttagcaaaggaaatggactcatagatg -continued ctaaccttaaaacaacgtgacaaatgccagacagg acccatcagccaggcactgtgagagcacagagcag ggaggttgggtcctgcctgaggagacctggaaggg aggcctcacaggaggatgaccaggtctcagtcagc ggggaggtggaaagtgcaggtgcatcaggggcacc ctgaccgaggaaacagctgccagaggcctccactg ctaaagtccacataaggctgaggtcagtcaccta aacaacctgctccctctaagccagggtgatgagctt ggagcatcccacaagttccctaaaagttgcagccc ccaggggggattttgagctateatctctgcacatge ttagtgagaagactacacaacatttctaagaatct gagattttatattgtcagttaaccactttcattat tcattcacctcaggacatgcagaaatatttcagtc agaactgggaaacagaaggacctacattctgctgt cacttatgtgtcaagaagcagatgategatgagge aggtcagttgtaagtgagtcacattgtagcattaa attctagtattttgtagtttgaaacagtaactta ataaaagagcaaaagctaaaaaaaaaaaaaaaaaa By "Epidermal Growth Factor Receptor (EGFR) poly-peptide" is meant a polypeptide or fragment thereof having at least about 85% amino acid identity to NCBI Accession No. NP_005219.2 and having Epidermal Growth Factor (EGF) binding activity, as reproduced below (SEQ ID NO: 4):

>NP_005219. 2
MRPSGTAGAALLALLAALCPASRALEEKKVCQGTSN

KLTQLGTFEDHFLSLQRMFNNCEVVLGNLEITYVQ

RNYDLSFLKTIQEVAGYVLIALNTVERIPLENLQI

IRGNMYYENSYALAVLSNYDANKTGLKELPMRNLQ

EILHGAVRFSNNPALCNVESIQWRDIVSSDFLSNM

SMDFQNHLGSCQKCDPSCPNGSCWGAGEENCQKLT

KIICAQQCSGRCRGKSPSDCCHNQCAAGCTGPRES

DCLVCRKFRDEATCKDTCPPLMLYNPTTYQMDVNP

EGKYSFGATCVKKCPRNYVVTDHGSCVRACGADSY

EMEEDGVRKCKKCEGPCRKVCNGIGIGEFKDSLSI

NATNIKHFKNCTSISGDLHILPVAFRGDSFTHTPP

LDPQELDILKTVKEITGFLLIQAWPENRTDLHAEE

NLEIIRGRTKQHGQFSLAVVSLNITSLGLRSLKEI

SDGDVIISGNKNLCYANTINWKKLFGTSGQKTKII

SNRGENSCKATGQVCHALCSPEGCWGPEPRDCVSC

RNVSRGRECVDKCNLLEGEPREFVENSECIQCHPE

CLPQAMNITCTGRGPDNCIQCAHYIDGPHCVKTCP

-continued

AGVMGENNTLVWKYADAGHVCHLCHPNCTYGCTGP

GLEGCPTNGPKIPSIATGMVGALLLLLVVALGIGL

FMRRRHIVRKRTLRRLLQERELVEPLTPSGEAPNQ

ALLRILKETEFKKIKVLGSGAFGTVYKGLWIPEGE

KVKIPVAIKELREATSPKANKEILDEAYVMASVDN

PHVCRLLGICLTSTVQLITQLMPFGCLLDYVREHK

DNIGSQYLLNWCVQIAKGMNYLEDRRLVHRDLAAR

NVLVKTPQHVKITDFGLAKLLGAEEKEYHAEGGKV

PIKWMALESILHRIYTHQSDVWSYGVTVWELMTFG

SKPYDGIPASEISSILEKGERLPQPPICTIDVYMI

MVKCWMIDADSRPKFRELIIEFSKMARDPQRYLVI

QGDERMHLPSPTDSNFYRALMDEEDMDDVVDADEY

LIPQQGFFSSPSTSRTPLLSSLSATSNNSTVACID

RNGLQSCPIKEDSFLQRYSSDPTGALTEDSIDDTF

LPVPEYINQSVPKRPAGSVQNPVYHNQPLNPAPSR

DPHYQDPHSTAVGNPEYLNTVQPTCVNSTFDSPAH

WAQKGSHQISLDNPDYQQDFFPKEAKPNGIFKGST

AENAEYLRVAPQSSEFIGA

By "Epidermal Growth Factor (EGF) nucleic acid molecule" is meant a polynucleotide encoding an EGF polypeptide. An exemplary EGF nucleic acid molecule is provided at NCBI Accession No. NM_001963.5, and reproduced below (SEQ ID NO: 5):

>NM_001963.5
aaaaagagaaactgttgggagaggaatcgtatctc catatttcttctttcagccccaatccaagggttgt agctggaactttccatcagttcttcctttctttt cctctctaagcctttgccttgctctgtcacagtga agtcagccagagcagggctgttaaactctgtgaaa tttgtcataagggtgtcaggtatttcttactggct tccaaagaaacatagataaagaaatctttcctgtg gcttcccttggcaggctgcattcagaaggtctctc agttgaagaaagagcttggaggacaacagcacaac aggagagtaaaagatgccccagggctgaggcctcc gctcaggcagccgcatctggggtcaatcatactca ccttgcccgggccatgctccagcaaaatcaagctg ttttcttttgaaagttcaaactcatcaagattatg ctgctcactcttatcattctgttgccagtagtttc aaaatttagttttgttagtctctcagcaccgcagc actggagctgtcctgaaggtactctcgcaggaaat gggaattctacttgtgtgggtcctgcacccttctt aattttctcccatggaaatagtatctttaggattg -continued acacagaaggaaccaattatgagcaattggtggtg gatgctggtgtctcagtgatcatggattttcatta taatgagaaaagaatctattgggtggatttagaaa gacaacttttgcaaagagttttctgaatgggtca aggcaagagagagtatgtaatatagagaaaaatgt ttctggaatggcaataaattggataaatgaagaag ttatttggtcaaatcaacaggaaggaatcattaca gtaacagatatgaaaggaaataattcccacattct tttaagtgctttaaaatatcctgcaaatgtagcag ttgatccagtagaaaggtttatattttggtcttca gaggtggctggaagcctttatagagcagatctcga tggtgtgggagtgaaggctctgttggagacatcag agaaaataacagctgtgtcattggatgtgcttgat aagcggctgttttggattcagtacaacagagaagg aagcaattctcttatttgctcctgtgattatgatg gaggttctgtccacattagtaaacatccaacacag cataatttgtttgcaatgtcccttttttggtgaccg tatcttctattcaacatggaaaatgaagacaatt ggatagccaacaaacacactggaaaggacatggtt agaattaacctccattcatcatttgtaccacttgg tgaactgaaagtagtgcatccacttgcacaaccca aggcagaagatgacacttgggagcctgagcagaaa ctttgcaaattgaggaaaggaaactgcagcagcac tgtgtgtgggcaagacctccagtcacacttgtgca tgtgtgcagagggatacgccctaagtcgagaccgg aagtactgtgaagatgttaatgaatgtgctttttg gaatcatggctgtactcttgggtgtaaaaacaccc ctggatcctattactgcacgtgccctgtaggattt gttctgcttcctgatgggaaacgatgtcatcaact tgtttcctgtccacgcaatgtgtctgaatgcagcc atgactgtgttctgacatcagaaggtcccttatgt ttctgtcctgaaggctcagtgcttgagagagatgg gaaaacatgtagcggttgttcctcacccgataatg gtggatgtagccagctctgcgttcctcttagccca gtatcctgggaatgtgattgctttcctgggtatga cctacaactggatgaaaaaagctgtgcagcttcag gaccacaaccattttgctgtttgccaattctcaa gatattcgacacatgcattttgatggaacagacta tggaactctgctcagccagcagatgggaatggttt atgccctagatcatgaccctgtggaaaataagata -continued

```
tactttgcccatacagccctgaagtggatagagag agctaatatggatggttcccagcgagaaaggctta ttgaggaaggagtagatatgccagaaggtcttgct gtggactggattggccgtagattctattggacaga cagagggaaatctctgattggaaggagtgatttaa atgggaaacgttccaaaataatcactaaggagaac atctctcaaccacgaggaattgctgttcatccaat ggccaagagattattctggactaatacagggatta atccacgaattgaaagttcttccctccaaggcctt ggccgtctggttatagccagctctgatctaatctg gcccagtggaataacgattgacttcttaactgaca agttgtactggtgcgatgccaagcagtctgtgatt gaaatggccaatctggatggttcaaaacgccgaag acttacccagaatgatgtaggtcacccatttgctg tagcagtgtttgaggattatgtgtggttctcagat tgggctatgccatcagtaatgagagtaaacaagag gactggcaaagatagagtacgtctccaaggcagca tgctgaagccctcatcactggttgtggttcatcca ttggcaaaaccaggagcagatccctgcttatatca aaacggaggctgtgaacatatttgcaaaaagaggc ttggaactgcttggtgttcgtgtcgtgaaggtttt atgaaagcctcagatgggaaaacgtgtctggctct ggatggtcatcagctgttggcaggtggtgaagttg atctaaagaaccaagtaacaccattggacatcttg tccaaaactagagtgtcagaagataacattacaga atctcaacacatgctagtggctgaaatcatggtgt cagatcaagatgactgtgctcctgtgggatgcagc atgtatgctcggtgtatttcagagggagaggatgc cacatgtcagtgtttgaaaggatttgctggggatg gaaaactatgttctgatatagatgaatgtgagatg ggtgtcccagtgtgcccccctgcctcctccaagtg catcaacaccgaaggtggttatgtctgccggtgct cagaaggctaccaaggagatgggattcactgtctt gatattgatgagtgccaactgggggagcacagctg tggagagaatgccagctgcacaaatacagagggag gctatacctgcatgtgtgctggacgcctgtctgaa ccaggactgatttgccctgactctactccacccccc tcacctcagggaagatgaccaccactattccataa gaaatagtgactctgaatgtcccctgtcccacgat gggtactgcctccatgatggtgtgtgcatgtatat tgaagcattggacaagtatgcatgcaactgtgttg
```

-continued

```
ttggcfcacatcggggagcgatgtcagtaccgaga cctgaagtggtgggaactgcgccacgctggccacg ggcagcagcagaaggtcatcgtggtggctgtctgc gtggtggtgcttgtcatgctgctcctcctgagcct gtggggggcccactactacaggactcagaagcfcg ctatcgaaaaacccaaagaatccttatgaggagtc gagcagagatgtgaggagtcgcaggcctgctgaca ctgaggatgggatgtcctcttgccctcaaccttgg tttgtggttataaaagaacaccaagacctcaagaa tgggggtcaaccagtggctggtgaggatggccagg cagcagatgggtcaatgcaaccaacttcatggagg caggagccccagttatgtggaatgggcacagagca aggctgctggattccagtatccagtgataagggct cctgtccccaggtaatggagcgaagctttcatatg ccctcctatgggacacagacccttgaaggggggtgt cgagaagccccattctctcctatcagctaacccat tatggcaacaaagggccctggacccaccacaccaa atggagctgactcagtgaaaactggaattaaaagg aaagtcaagaagaatgaactatgtcgatgcacagt atcttttctttcaaaagtagagcaaaactataggt tttggttccacaatctctacgactaatcacctact caatgcctggagacagatacgtagttgtgcttttg tttgctcttttaagcagtctcactgcagtcttatt tccaagtaagagtactgggagaatcactaggtaac ttattagaaacccaaattgggacaacagtgctttg taaattgtgttgtcttcagcagtcaatacaaatag atttttgtttttgttgttcctgcagccccagaaga aattaggggttaaagcagacagtcacactggtttg gtcagttacaaagtaatttctttgatctggacaga acatttatatcagtttcatgaaatgattggaatat tacaataccgttaagatacagtgtaggcatttaac tcctcattggcgtggtccatgctgataattttgca aaatgagttgtgatgaatcaatgaaaaatgtaatt tagaaactgatttcttcagaattagatggcttatt ttttaaaatatttgaatgaaaacattttatttttta aaatattacacaggaggcttcggagtttcttagtc attactgtcctttttcccctacagaattttccctct tggtgtgattgcacagaatttgtatgtattttcag ttacaagattgtaagtaaattgcctgatttgtttt cattatagacaacgatgaatttcttctaattattt
```

-continued
```
aaataaaatcaccaaaaacataaacattttattgt atgcctgattaagtagttaattatagtctaaggca gtactagagttgaaccaaaatgatttgtcaagctt gctgatgtttctgtttttcgtttttttttttttttc cggagagaggataggatctcactctgttatccagg ctggagtgtgcaatggcacaatcatagctcagtgc agcctcaaactcctgggctcaagcaatcctcctgc ctcagcctcccgagtaactaggaccacaggcacag gccaccatgcctggctaaggttttttattttttattt tttgtagacatggggatcacacaatgttgcccagg ctggtcttgaactcctggcctcaagcaaggtcgtg ctggtaattttgcaaaatgaattgtgattgactt cagcctcccaacgtattagattataggcattagcc atggtgcccagccttgtaactttaaaaaaattt ttaatctacaactctgtagattaaaatttcacatg gtgttctaattaaatatttttcttgcagccaagat attgttactacagataacacaacctgatatggtaa ctttaaattttgggggctttgaatcattcagttta tgcattaactagtcccttttgtttatctttcatttc tcaaccccttgtactttggtgataccagacatcag aataaaagaaattgaagtacctgttttcaaatgg atactttataggaattttggtaaagatttggtgat gggaggatgacttgaggtttgtggatattagttaa ttattcagtatgatacctcacccagctaattt
```

By "Epidermal Growth Factor (EGF) polypeptide" is meant a polypeptide or fragment thereof having at least about 85% amino acid identity to NCBI Accession No. NP_001954.2 and corresponding to a pre-pro-protein form of EGF that is processed to produce a 53 amino acid EGF molecule (shown in bold) and having EGFR binding activity (an hEGF Targeted Signaling Pathway (TSP) domain), as reproduced below (SEQ ID NO: 6):

```
>NP 001954.2
MLLTLIILLPVVSKFSFVSLSAPQHWSCPEGTLAGN

GNSTCVGPAPFLIFSHGNSIFRIDTEGTNYEQLVV

DAGVSVIMDFHYNEKRIYWVDLERQLLQRVFLNGS

RQERVCNIEKNVSGMAINWINEEVIWSNQQEGIIT

VTDMKGNNSHILLSALKYPANVAVDPVERFIFWSS

EVAGSLYRADLDGVGVKALLETSEKITAVSLDVLD

KRLFWIQYNREGSNSLICSCDYDGGSVHISKHPTQ

HNLFAMSLFGDRIFYSTWKMKTIWIANKHTGKDMV

RINLHSSFVPLGELKVVHPLAQPKAEDDTWEPEQK

LCKLRKGNCSSTVCGQDLQSHLCMCAEGYALSRDR
```

-continued
```
KYCEDVNECAFWNHGCTLGCKNTPGSYYCTCPVGF

VLLPDGKRCHQLVSCPRNVSECSHDCVLTSEGPLC

FCPEGSVLERDGKTCSGCSSPDNGGCSQLCVPLSP

VSWECDCFPGYDLQLDEKSCAASGPQPFLLFANSQ

DIRHMHFDGTDYGTLLSQQMGMVYALDHDPVENKI

YFAHTALKWIERANMDGSQRERLIEEGVDVPEGLA

VDWIGRRFYWTDRGKSLIGRSDLNGKRSKIITKEN

ISQPRGIAVHPMAKRLEWTDTGINPRIESSSLQGL

GRLVIASSDLIWPSGITIDFLTDKLYWCDAKQSVI

EMANLDGSKRRRLTQNDVGHPFAVAVFEDYVWFSD

WAMPSVMRVNKRTGKDRVRLQGSMLKPSSLVVVHP

LAKPGADPCLYQNGGCEHICKKRLGTAWCSCREGF

MKASDGKTCLALDGHQLLAGGEVDLKNQVTPLDIL

SKTRVSEDNITESQHMLVAEIMVSDQDDCAPVGCS

MYARCISEGEDATCQCLKGFAGDGKLCSDIDECEM

GVPVCPPASSKCINTEGGYVCRCSEGYQGDGIHCL

DIDECQLGEHSCGENASCTNTEGGYTCMCAGRLSE

PGLICPDSTPPPHLREDDHHYSVRNSDSECPLSHD

GYCLHDGVCMYIEALDKYACNCVVGYIGERCQYRD

LKWWELRHAGHGQQQKVIVVAVCVVVLVMLLLLSL

WGAHYYRTQKLLSKNPKNPYEESSRDVRSRRPADT

EDGMSSCPQPWFVVIKEHQDLKNGGQPVAGEDGQA

ADGSMQPTSWRQEPQLCGMGTEQGCWIPVSSDKGS

CPQVMERSFHMPSYGTQTLEGGVEKPHSLLSANPL

WQQRALDPPHQMELTQ
```

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

By "subject" is meant a mammal, including, but not limited to, a human or non-human mammal, such as a bovine, equine, canine, ovine, or feline.

By "EGFR effector" is meant any protein including kinases, downstream of EGFR, as disclosed herein and as is commonly known in the art.

By "NTKI" or "non-tyrosine targeting kinase inhibitor" is meant any compound that specifically targets kinases without affecting tyrosine phosphorylation. In contrast to Tyrosine Kinase Inhibitors (TKIs), "NTKIs" refers to kinase inhibitors of kinases that are not Receptor Tyrosine Kinases (e.g EGFR). Rather NTKIs target kinases downstream of receptors. In some embodiments these kinases are downstream of EGFR.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reference" is meant a standard or control condition. In one embodiment, the effect of an agent on a cell is compared to the effect of the agent on a control cell.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

By "synthetic TSP domain" is meant or fragment thereof having at least about 85%, 90%, 91%, 92%, 93%, 94%, 95%, 96%, 97%, 98%, or 99% amino acid identity to the amino acid sequence below (SEQ ID NO: 7):

```
synthetic TSP domain
NTENDCPLSHEAYCLHDGVCMYIEALDK

YACNCVVGYVGERCQFRDLRWWDAR
```

By "hEGF TSP domain" is meant or fragment thereof having at least about 85%, 90%, 91%, 92%, 93%, 94%, 95%, 96%, 97%, 98%, or 99% amino acid identity to the amino acid sequence below, as shown in bold above in SEQ ID NO: 6, (SEQ ID NO: 8):

```
>hEGE TSP domain
NSDSECPLSHDGYCLHDGVCMYIEALDKY

ACNCVVGYIGERCQYRDLKWWELR
```

By "CTB polypeptide" is meant or fragment thereof having at least about 85%, 90%, 91%, 92%, 93%, 94%, 95%, 96%, 97%, 98%, or 99% amino acid identity to the amino acid sequence below (SEQ ID NO: 25):

>CTB polypeptide
TPQNITDLCABYHNTQIHTLNDKIFSYTESLADKREMA

IITFKNGATEQVEVPGSQHIDSQKKAIERMKDTLRIAY

LTEAKVEKLCVWNNKTPHAIAAISMAN

Where applicable or not specifically disclaimed, any one of the embodiments described herein are contemplated to be able to combine with any other one or more embodiments, even though the embodiments are described under different aspects of the disclosure.

These and other embodiments are disclosed and/or encompassed by, the following Detailed Description.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 5A shows the effect of 3 day incubation with the anti-IN01 therapeutic antibody, or a control antibody, C-Ab, used in combination with different concentrations of Trametinib on DLD1 cell viability. FIG. 5B shows the longer term effects on DLD1 cell viability of the anti-IN01 therapeutic antibody, or a control antibody, C-Ab, used in combination with Trametinib.

FIG. 13A shows the effect of a 3 day incubation with the anti-IN01 therapeutic antibody, or a control antibody, C-Ab, used in combination with different concentrations of Trametinib on HT29 cell viability. FIG. 13B shows the effects on pEGFR and pErk ½ signaling, assessed by western blot, of a 2 hour incubation with EGF, 0.01 mM Trametinib, and the anti-IN01 antibody, referred to as "Ab8," alone or in combination, in LS174T cells. The anti-IN01 Ab was diluted 1:10 for these experiments. FIG. 13C shows the longer term effects on HT29 cell viability of the anti-IN01 therapeutic antibody used in combination with EGF and Trametinib. EGF was added at a concentration of 10 ng/mL to the cell culture media.

FIG. 21, left, shows the effect of a 3 day incubation with the anti-IN01 therapeutic antibody, "Ab," or a control antibody, "C Ab," used in combination with different concentrations of Alpelisib on H508 cell viability in the presence of EGF. FIG. 21, right, shows the effect of a 3 day incubation with the anti-IN01 therapeutic antibody, "Ab," or a control antibody, "C Ab," used in combination with different concentrations of Copanlisib on H508 cell viability in the presence of EGF.

FIG. 28, bottom, shows the effects on PC9 cell viability of the anti-IN01 antibody, referred to as "Ab," and the control antibody, referred to as "C-Ab," in combination with 0.5 mM Dacomitinib.

FIG. 42 shows the western blot quantification of the pEGFR and pErk½ signaling response in H288 cells to patient-derived anti-EGF antibody titers, and to the anti-IN01 antibody, referred to as "Ab."

FIG. 43 shows exemplary alterations present in colorectal cancer cell lines.

FIG. 51, bottom, shows the effects of a 3 day incubation with different concentrations of Encorafenib, with and without EGF, on HT29 cell viability.

FIG. 52, bottom, shows the effects of a 3 day incubation with different concentrations of Encorafenib, either alone or in combination with the anti-IN01 antibody "Ab," or the control antibody "C-Ab," on HT29 cell viability.

Top, right, shows the long term effects of EGF, the anti-IN01 antibody, "Ab," alone or in combination with 0.1 mM Trametinib, on HT29 cell viability. Bottom, left, shows the long term effects of EGF, the anti-IN01 antibody, "Ab," alone or in combination with 0.01 mM Encorafenib, on HT29 cell viability. Bottom, right, shows the long term effects of EGF, the anti-IN01 antibody, "Ab," alone or in combination with 0.1 mM Encorafenib, on HT29 cell viability.

Figure 70:
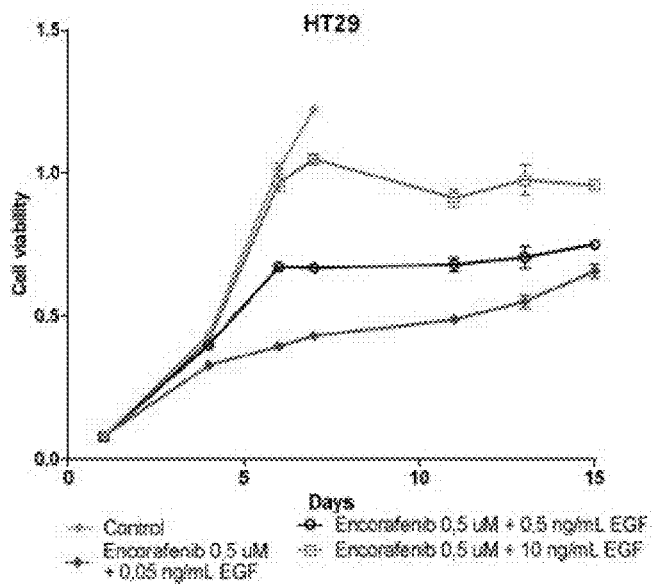

FIG. 70 shows the long term effects of different concentrations of EGF in combination with 0.5 mM Encorafenib on HT29 cell viability.

Figure 71:
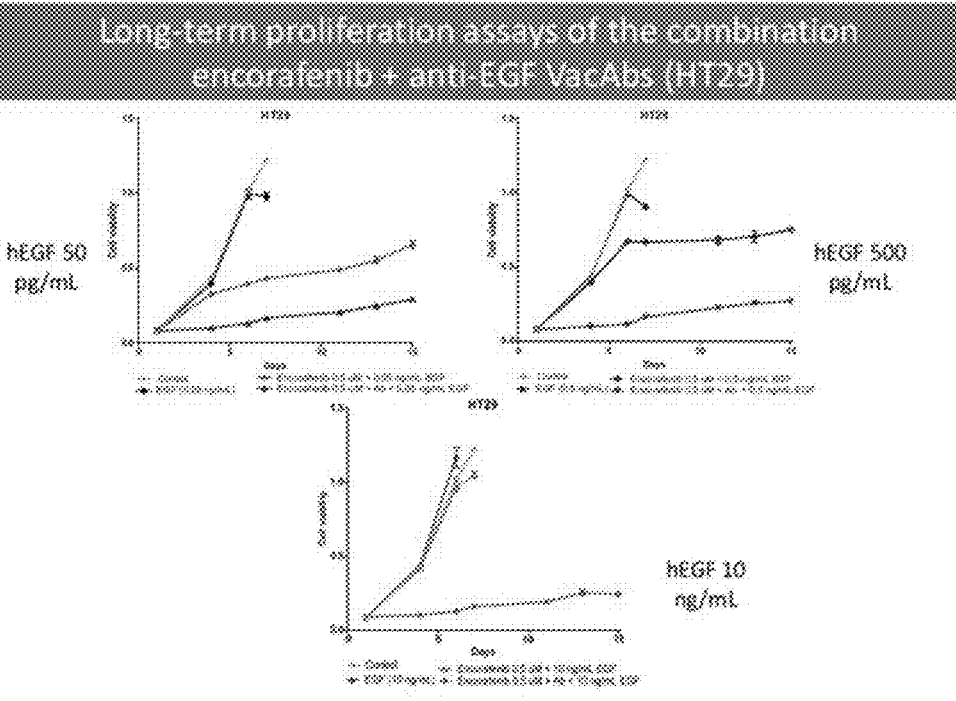

FIG. 71 shows the long term effects of different concentrations of EGF in combination with 0.5 mM Encorafenib, and the anti-IN01 antibody, on HT29 cell viability. Top, left, shows the long term effects of 0.05 ng/mL EGF in combination with 0.5 mM Encorafenib, and the anti-IN01 antibody on HT29 cell viability. Top, right, shows the long term effects of 0.5 ng/mL EGF in combination with 0.5 mM Encorafenib, and the anti-IN01 antibody on HT29 cell viability. Bottom, shows the long term effects of 10 ng/mL EGF in combination with 0.5 mM Encorafenib, and the anti-IN01 antibody on HT29 cell viability.

Figure 72:
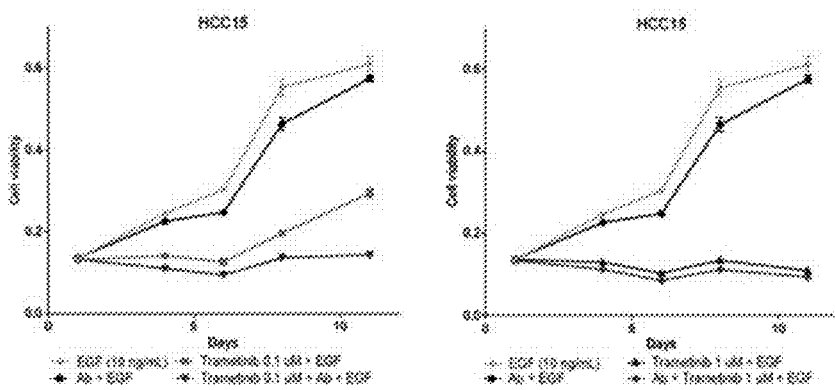

FIG. 72 shows the long term effects of Trametinib and the anti-IN01 antibody on HCC15 cell viability. Left, shows the long term effects of 0.1 mM Trametinib alone, and in combination with the anti-IN01 antibody on HCC15 cell viability in the presence of EGF. Right, shows the long term effects of 1.0 mM Trametinib alone, and in combination with the anti-IN01 antibody on HCC15 cell viability in the presence of EGF.

Figure 73:
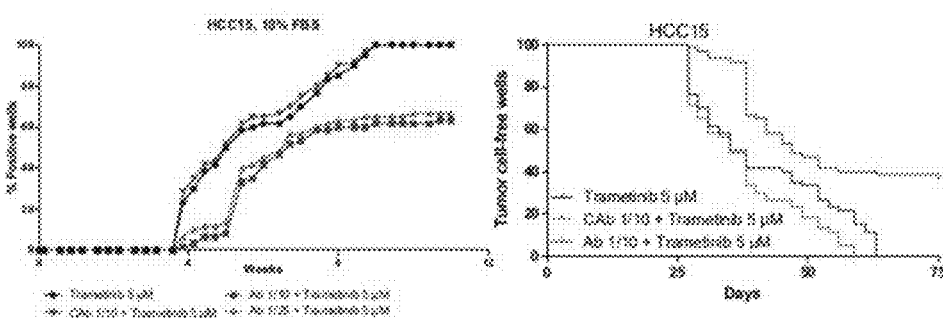

FIG. 73 shows the emergence of resistance to Trametinib in HCC15 cells. Left, shows the long term effects of Trametinib in combination with either 1/10 or 1/25 dilutions of the anti-IN01 antibody, "Ab," or a control antibody, "C-Ab," on HCC15 cell viability. Right, shows the long term effects of Trametinib in combination with either the anti-IN01 antibody, "Ab," or a control antibody, "C-Ab," on HCC15 cell viability.

Figures 74, 75:
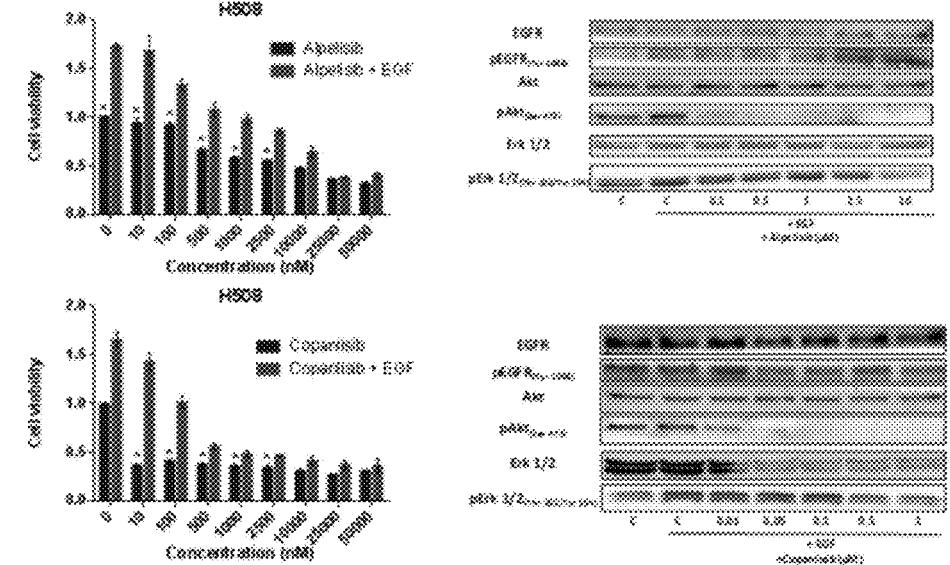

FIG. 74 shows the H508 cell line alterations and PIK3CA kinase inhibitors used in the instant application.

FIG. 75 shows the effects of kinase inhibitors Alpelisib and Copanlisib with and without EGF in H508 cells. Top, left, shows the effects of 3 day incubation with different concentrations of Alpelisib with and without EGF on H508 cell viability. Top, right, shows the effects on pEGFR, pAkt, and pErk½ on 2 hour incubation of EGF and different concentrations of Alpelisib. Bottom, left, shows the effects of 3 day incubation with different concentrations of Copanlisib with and without EGF on H508 cell viability. Bottom, right, shows the effects on pEGFR, pAkt, and pErk½ on 2 hour incubation of EGF and different concentrations of Copanlisib.

Figure 76:
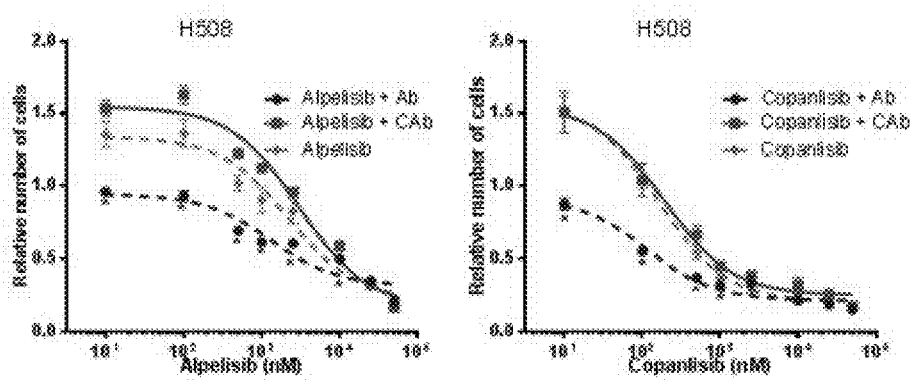

FIG. 76 shows the effects of kinase inhibitors in combination with the anti-IN01 antibody, "Ab," or a control antibody, "C-Ab," on H508 cell viability, in the presence of EGF. Left, shows the effects of a 3 day incubation of different concentrations of Alpelisib in combination with the anti-IN01 antibody, "Ab," or a control antibody, "C-Ab," on H508 cell viability. Right, shows the effects of a 3 day incubation of different concentrations of Copanlisib in combination with the anti-IN01 antibody, "Ab," or a control antibody, "C-Ab," on H508 cell viability.

Figure 77:
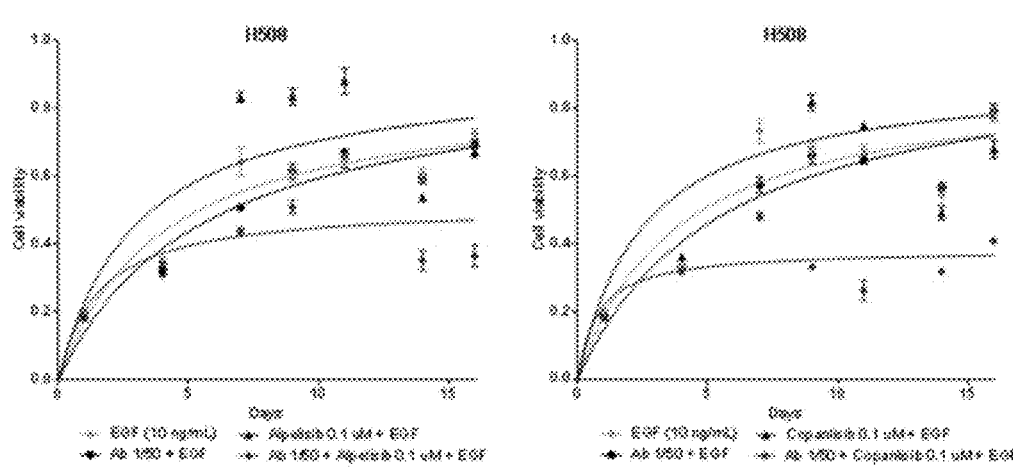

FIG. 77 shows the long term effects of kinase inhibitors in combination with the anti-IN01 antibody on H508 cell viability, in the presence of EGF. Left, shows the long term effects of EGF, Alpelisib, and a 1/50 dilution of the anti- IN01 antibody on H508 cell viability. Right, shows the long term effects of EGF, Copanlisib, and a 1/50 dilution of the anti-IN01 antibody on H508 cell viability.

Figures 78, 79:
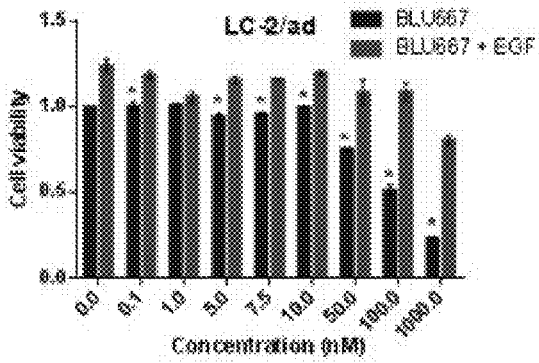

FIG. 78 shows the cell line, histology, kinase inhibitor, and relevant alteration of the RET translocated cell line used in the instant application.

FIG. 79 shows the effects of a 3 day incubation of different concentrations of the BLU667 kinase inhibitor on LC-2/ad cell viability, with and without EGF.

Figure 80:
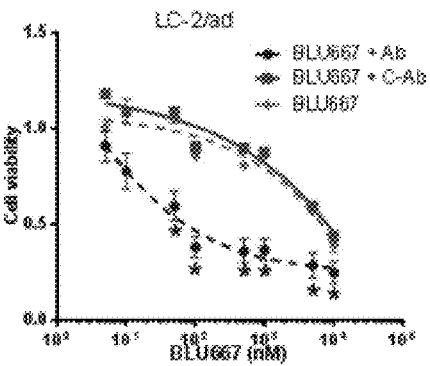

FIG. 80 shows the effects of a 3 day incubation of different concentrations of EGF, and the the BLU667 kinase inhibitor, in combination with the anti-IN01 antibody, "Ab," or a control antibody, "C-Ab," on LC-2/ad cell viability.

Figure 81:
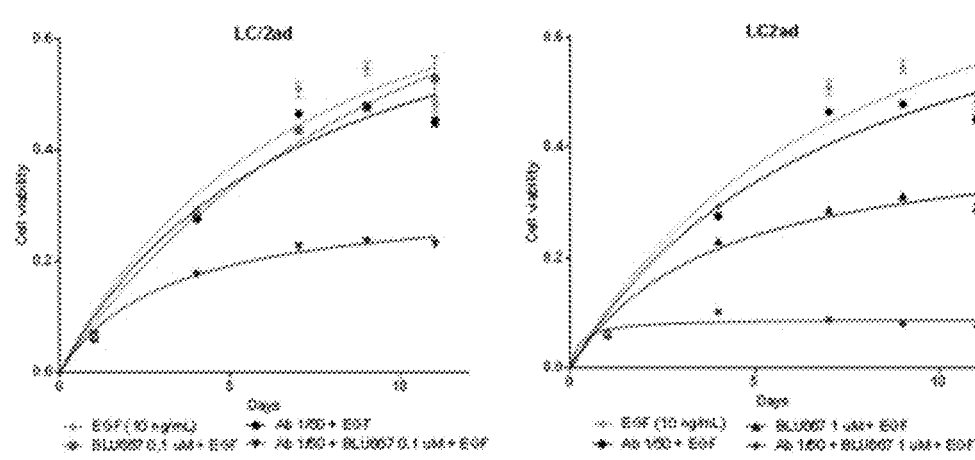

FIG. 81 shows the long term effects of the BLU667 kinase inhibitor, in combination with the anti-IN01 antibody, on LC/2ad cell viability in the presence of EGF. Left, shows the long term effects of EGF and a 1/50 dilution of the anti-IN01 antibody alone or in combination with 0.1 mM BLU667, on LC/2ad cell viability. Left, shows the long term effects of EGF and a 1/50 dilution of the anti-IN01 antibody alone or in combination with 1.0 mM BLU667, on LC/2ad cell viability.

Figures 82, 83:
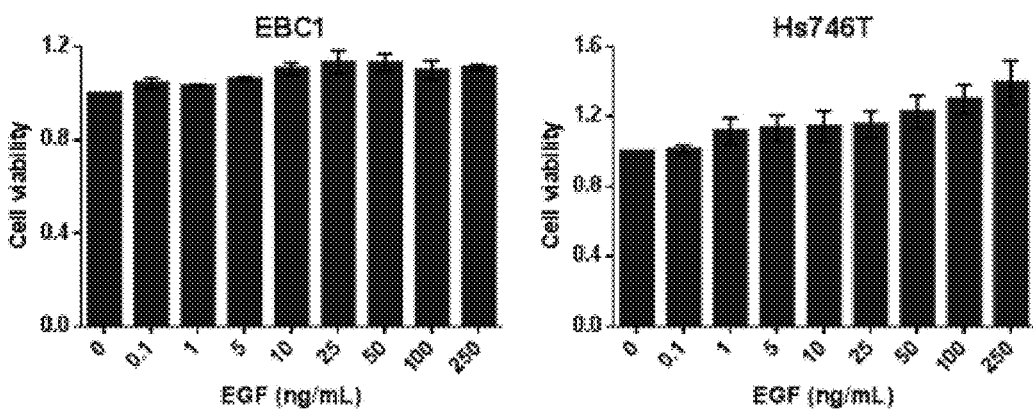

FIG. 82 shows the cell lines used, the tissues from which they were derived, and the relevant MET alterations.

FIG. 83 shows the effects of 3 day incubation with EGF on left, EBC1 and right, Hs746T cell viability.

Figure 84:
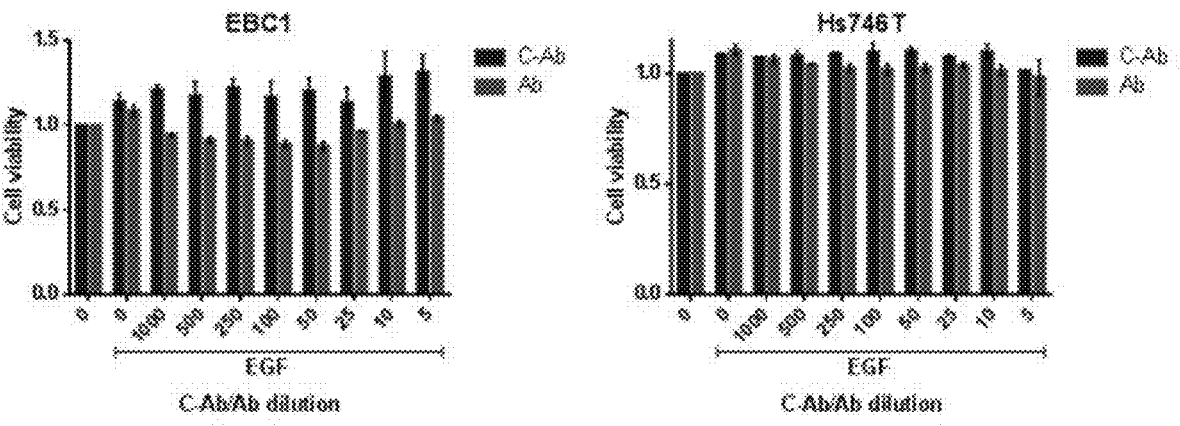

FIG. 84 shows the effects of 3 day incubation of the anti-IN01 antibody, "Ab," or control antibody, "C-Ab," on left, EBC1 and right, Hs746T cell viability with different dilutions of EGF.

Figure 85:
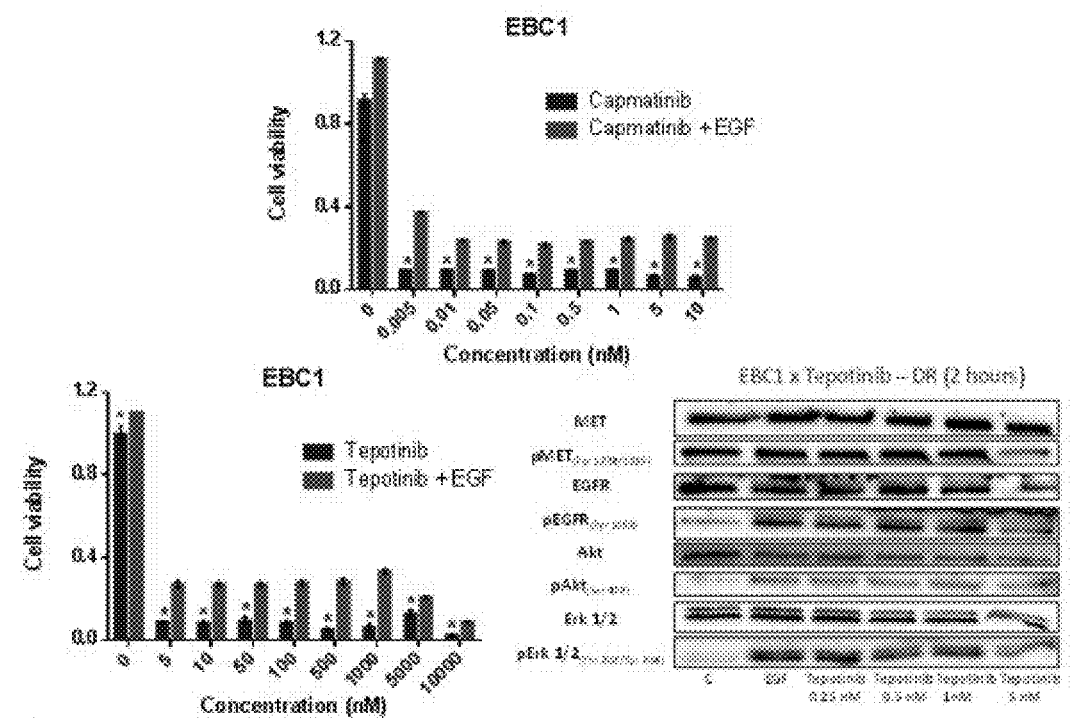

FIG. 85 shows the effects of 3 day incubation of top, Capmatinib and bottom left, Tepotinib on EBC1 cell viability, with and without EGF. Bottom right, is shown the effects of 2 hour incubation of different concentations of Tepotinib on pMET, pEGFR, pAkt, and pErk½ activation in EBC1 cells.

Figure 86:
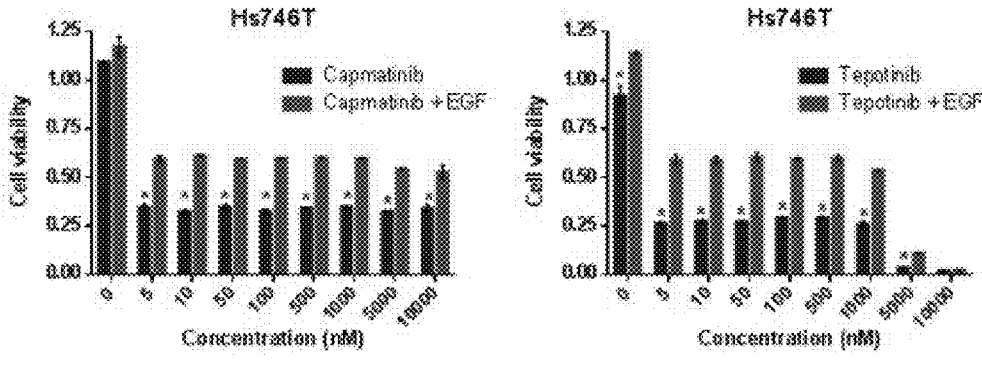

FIG. 86 shows the effects of a 3 day incubation with different concentrations of left, Capmatinib and right, Tepotinib, with and without EGF, on Hs746T cell viability.

Figure 87:
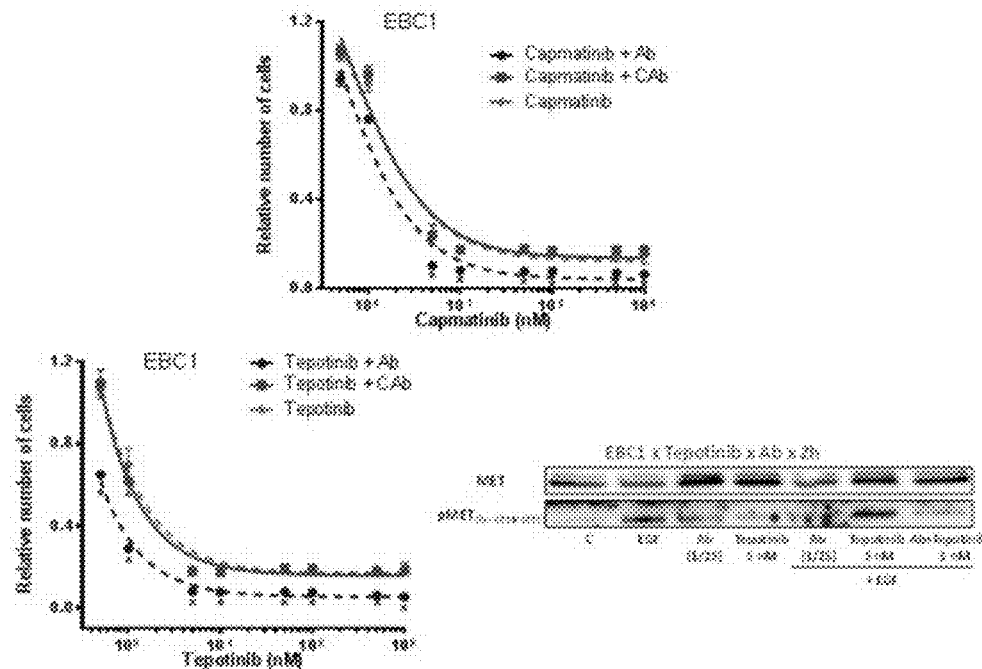

FIG. 87 shows the effects of 3 day incubation of different concentrations of top, Capmatinib and bottom left, Tepotinib, in combination with the anti-IN01 antibody, "Ab," or control antibody, "C-Ab," on EBC1 cell viability, and bottom right, the effects of 2 hour incubation with Tepotinib on pMET signaling in EBC1 cells.

Figure 88:
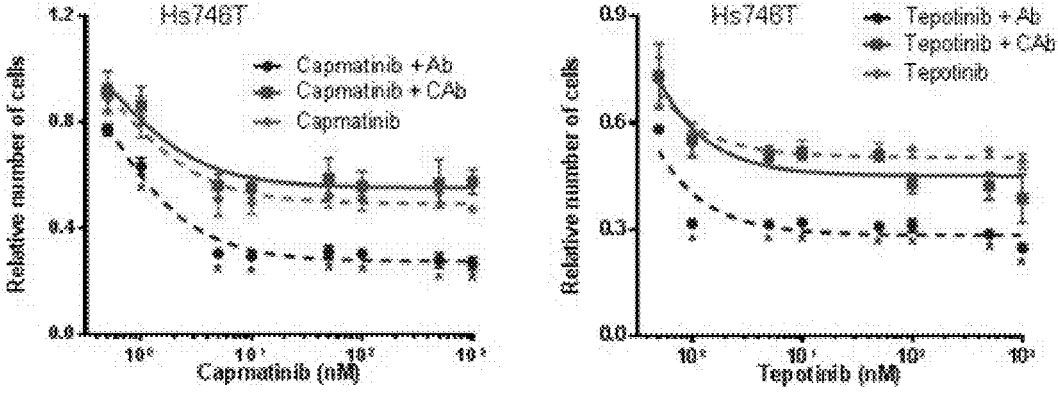

FIG. 88 shows the effects of 3 day incubation of different concentrations of left, Capmatinib and right, Tepotinib, in combination with the anti-IN01 antibody, "Ab," or control antibody, "C-Ab," on Hs746T cell viability.

Figure 89:
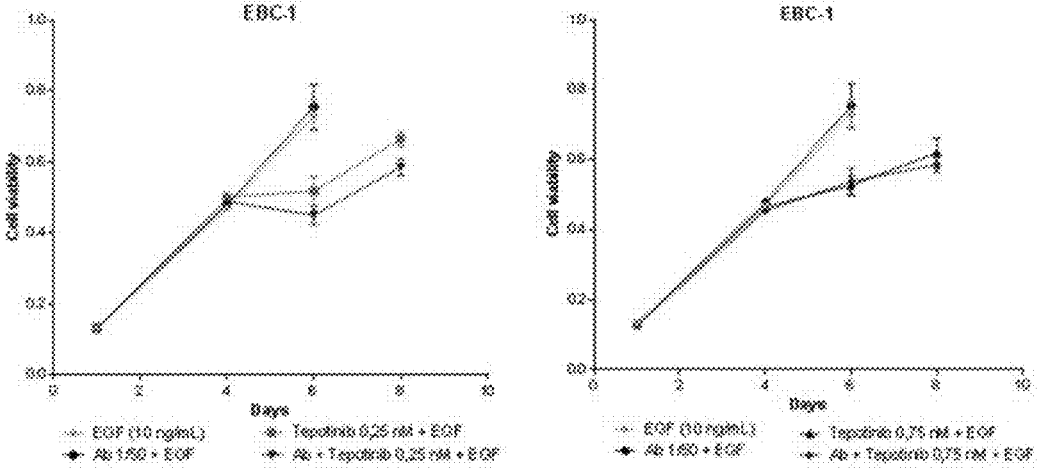

FIG. 89 shows the long-term effects on EBC1 cell viability of incubation with left, 0.25 nM Tepotinib and EGF, alone and in combination with the anti-IN01 antibody, and right, 0.75 nM Tepotinib and EGF, alone and in combination with the anti-IN01 antibody.

Figure 90:
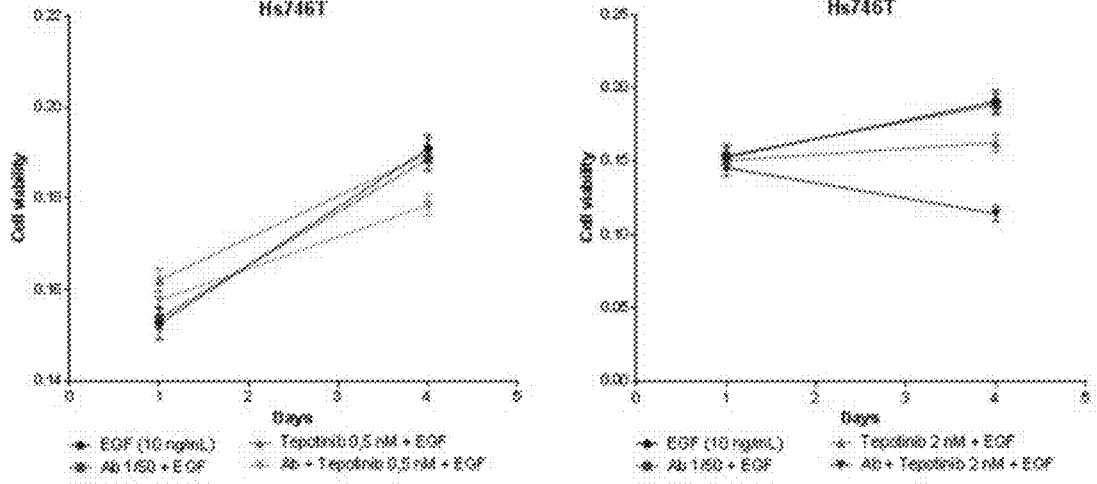

FIG. 90 shows the long-term effects on Hs746T cell viability of incubation with left, 0.5 nM Tepotinib and EGF, alone and in combination with the anti-IN01 antibody, and right, 2.0 nM Tepotinib and EGF, alone and in combination with the anti-IN01 antibody

DETAILED DESCRIPTION OF THE DISCLOSURE

The disclosure provides compositions and methods for treating neoplasia. In particular, the disclosure provides compositions and methods for enhancing the efficacy of non-tyrosine targeting kinase inhibitors (NTKIs) for treating neoplasia (e.g. colon adenocarcinoma and non-small cell lung carcinoma). In particular, the disclosure provides combination therapies including non-natural synthetic polypeptides (e.g., recombinant proteins) and/or antibodies for inducing immunization to EGF, EGFR, or other growth factors, in combination with NTKIs targeting EGFR effectors, to prevent or minimize resistance to NTKIs and thereby inhibit a neoplasia (e.g. non-small cell lung carcinoma and adenocarcinoma). In particular, the disclosure provides compositions and methods for administering an anti-IN01 antibody in combination with one or more NKTIs, e.g. Trametinib, Taselisib, Alpelisib, Copanlisib, and/or Encorafenib, for treatment of cancer in patients with mutations in KRAS/NRAS, PIK3CA, or BRAF genes in order to delay or prevent resistance to the NKTI.

The present disclosure is based, at least in part, on the discovery that anti-IN01 antibodies at physiological concentrations, in combination with NTKIs, significantly delayed the onset of resistance to the NTKIs, decreased cancer cell viability relative to the NTKIs alone, and inhibited the activation of pEGFR and pErk½ to a greater extent than NTKIs alone. These data demonstrate that EGF non-natural synthetic polypeptides (NNSPs) and/or antibodies thereof significantly enhanced the effect of EGFR effector NTKIs in inhibiting EGFR effector kinases and EGFR pathway signaling. Treatment of patients exhibiting KRAS/NRAS, PIK3CA, or BRAF mutations with an EGF non-natural synthetic polypeptide an/or antibody in combination with one or more NKTIs provides an important mechanism for delaying or inhibiting the resistance to these compounds, thereby facilitating the treatment of resistant cancers.

Patients with wild type EGFR effector proteins—for example, RAS, BRAF, MEK, and PIK3CA—can be treated with tyrosine kinase inhibitors (TKIs) targeting EGFR such as Cetuximab and Erlotinib. However, there is a large cohort of cancer patients harboring mutations in EGFR effector proteins. Extant treatments are not effective for these patients because the mutations often provide resistance to the TKIs targeting EGFR and the other non-tyrosine targeting kinase inhibitors targeting downstream proteins. Similarly, treatment with TKIs targeting EGFR in patients with wild type EGFR effector proteins often results in the development of resistance due to the selection for oncogenic mutations. Thus, although the extant treatments with TKIs and other non-tyrosine targeting kinase inhibitors exhibit strong anti-tumor properties targeting the EGFR pathway in some patients, they become less potent or entirely ineffective in patients who exhibit resistance. EGFR effector kinases may be referred to as 'bypass pathways', in that they have been identified as mechanisms of both intrinsic and acquired resistance to TKIs and non-tyrosine targeting kinase inhibitors. Without being bound by theory, it is thought that parallel or other kinases in the EGFR signaling cascade compensate for mutated kinases, thereby inducing stronger EGFR signaling effects. Therefore, there is a need for additional therapies to overcome resistance to EGFR pathway non-tyrosine targeting kinase inhibitors (NTKIs) in order to effectively treat EGFR or similar growth factor mediated diseases and cancers.

One such therapy is an initiation of an immune response. Antibodies to EGF, for example, control the division and proliferation of malignant cells by blocking EGFR signaling. The instant disclosure describes combination therapies of non-natural synthetic polypeptides (NNSPs) and/or antibodies thereof, in the immunization to EGF, EGFR, or other growth factors, and in combination with NTKIs targeting EGFR effectors, to prevent or minimize resistance to NTKIs and thereby inhibit tumor cell growth.

In some embodiments, such antibodies or antigen-binding fragments thereof can be used in the methods of treating cancer or other disorders of growth factor regulation. It is contemplated within the scope of the disclosure that anti-EGF antibodies can be actively produced in vivo by the administration of a vaccine (i.e. the IN01 peptide) producing an immune response to EGF. It is also contemplated within the scope of the disclosure that passive monoclonal anti-EFG antibodies can be administered (e.g. anti-IN01). It is contemplated that in some embodiments, mutations in other growth factor signaling pathways may play a similar compensatory role in providing resistance to NTKIs.

Overview

Cancer immunology is the study of interactions between an immune system and cancer cells such as, for example, tumors or malignancies. The initiation of an immune response, such as recognition of cancer-specific antigens that are expressed by human tumors and not expressed in normal tissues, is of particular interest. Generally, methods to control the division and proliferation of the malignant cells have focused on isolating these antigens and presenting them so that they are recognized by the immune system as foreign antigens to induce a specific immune response.

There are a significant number of growth factors identified at present, and most, if not all, have been shown to be important mediators of cell proliferation in various cancers in addition to being implicated in other disease conditions. Generally, growth factors are soluble serum proteins that recognize and bind to a group of growth factor receptors located on cell surfaces. Particular growth factors may be specific for a single receptor, or may bind to more than one closely related receptor with varying affinities. Similarly, some receptors bind to only a single growth factor ligand while others can bind to multiple related growth factors, again usually with differing affinities. Upon binding to its natural receptor, the cytoplasmic domain of the receptor is phosphorylated, and this initiates an intra-cellular signaling cascade that results in modulation of transcription of one or more genes and ultimately to progression through the cell cycle and cell proliferation.

Growth factors and their receptors are essential components of the normal processes of growth, development and repair, and their tissue distribution profiles and expression levels closely regulate cell growth. Numerous studies have shown that growth factors can stimulate proliferation of a variety of cell types both in vitro and in vivo (Cohen S., Carpenter G., PNAS USA 72, 1317, 1975, Witsch E et al: Physiology: 25(2):85-101, (2010)). Moreover, certain growth factors have been shown to stimulate proliferation in some cancer cell lines. For example epidermal growth factor (EGF) can stimulate some non-small cell lung carcinoma cells (Osborne C. K. et al. Can Res. 40, 2. 361 (1980)). Other growth factors such as vascular endothelial growth factor (VEGF), fibroblast growth factor (FGF), and platelet-derived growth factor (PDGF) are important in several oncology diseases, such as non-small cell lung cancer (NSCLC) (Ballas M S, Chachoua A., Onco Targets and Therapy: 4, 43-58 (2011)), prostate cancer, (Cox M E et al; Prostate 69 (1):33-40 (2009)), and breast cancer (Law J et al, Cancer Res; 68, 24: 10238-10346 (2008)).

Growth factor nucleic acid or peptide sequences anticipated to be used in some embodiments of the instant application include nucleic acid or peptide sequences of full length or portion thereof human or murine EGF, IGF-1, IGF-2, FGF1, FGF2, TGF-$\alpha$, TGF-$\beta$, VEGF-A, VEGF-B, VEGF-C, VEGF, D, PDGF, NGF, EGF, HGF, BMP's, KGF, MSF, PDL1, IL's 1-6, Neureguuins 1-4, and Neurotrophins. Similarly, it is anticipated that nucleic acid or peptide sequences of associated full length or portion thereof of growth factor receptors may be employed.

EGFR

The epidermal growth factor receptor (EGFR) is a member of the ErbB family of receptors, a subfamily of four closely related receptor tyrosine kinases: EGFR (ErbB-1), HER2/neu (ErbB-2), Her 3 (ErbB-3) and Her 4 (ErbB-4). EGFR is a transmembrane protein that is activated by binding of its specific ligands, including epidermal growth factor and transforming growth factor $\alpha$ (TGF$\alpha$).

EGFR dimerization stimulates its intrinsic intracellular protein-tyrosine kinase activity. As a result, autophosphorylation of several tyrosine (Y) residues in the C-terminal domain of EGFR occurs. These include Y992, Y1045, Y1068, Y1148 and Y1173. Autophosphorylation of EGFR elicits downstream activation and signaling of several other effector proteins, initiating several signal transduction cascades, e.g. the MAPK, Akt and JNK pathways, leading to DNA synthesis and cell proliferation. EGFR effectors modulate essential phenotypes such as cell migration, adhesion, and proliferation.

EGFR Effectors

A total of 219 reactions and 322 species were identified as downstream of EGFR signaling, i.e. EGFR effectors: Abi, abl-interactor; ADAM, a disintegrin and metalloproteinase; ADPR, ADP-ribose; Akt, v-akt murine thymoma viral oncogene homolog; AP-1, activator protein-1; Bad, BCL2-antagonist of cell death; cADPR, cyclic ADP-ribose; CAK, cyclin-dependent kinase-activating kinase; CaM, calmodulin; CaMK, calcium/calmodulin-dependent protein kinase; c-Cbl, Casitas B-lineage lymphoma proto-oncogene; CD, cluster of differentiation; Cdc, cell division cycle; Cdk, cyclin-dependent kinase; c-Fos, v-fos FBJ murine osteosarcoma viral oncogene; Chk, c-src tyrosine kinase (Csk) homologous kinase; c-Jun, v-jun sarcoma virus 17 oncogene homolog; c-Myc, v-myc myelocytomatosis viral oncogene homolog; CREB, cAMP response element-binding protein; c-Src, v-src sarcoma viral oncogene homolog; cyt., cytosol; DAG, diacylglycerol; EGF, epidermal growth factor; EGFR, epidermal growth factor receptor; Elk, Ets-like protein; end., endosome; EP, prostaglandin E receptor; Eps, EGF receptor pathway substrate; ER, endoplasmic reticulum; ErbB, erythroblastic leukemia viral (v-erb-b) oncogene homolog; ERK, extracellular signal-regulated kinase; Gab, GRB2-associated binding protein; GPCR, G protein-coupled receptor; Grb, growth factor receptor-bound protein; HB-EGF, heparin-binding EGF-like growth factor; IP3R, inositol 1,4,5-triphosphate receptor; IP3, inositol 1,4,5-triphosphate; JNK, c-Jun N-terminal kinase; KDI, kinase domain I; LARG, leukemia-associated rho guanine nucleotide exchange factor; LIMK, LIM (Lin-11 Isl-1 Mec-3) kinase; LPA, lysophosphatidic acid; LPA1/2, lysophosphatidic acid G protein-coupled receptor 1/2; lyso., lysosome; m., messenger; MAPK, mitogen-activated protein kinase; MEKK, MAPK/ERK kinase kinase; MKK, MAP kinase kinase; MKP, MAP kinase phosphatase; MLK, mixed lineage kinase; NAD, nicotinamide adenine dinucleotide; nuc., nucleus; PAK1, p21/Cdc42/Racl-activated kinase; PDK, 3-phosphoinositide-dependent protein kinase; PGE2, prostaglandin E2; Pi, phosphoric ion; PI3,4,5-P3, phosphatidylinositol-3,4,5-triphosphate; PI3,4-P2, phosphatidylinositol-3,4-bisphosphate; PI3K, phosphatidylinositol-3-kinase; PI4,5-P2, phosphatidylinositol-4,5-bisphosphate; PI4-P, phosphatidylinositol-4-phosphate; PI5K, phosphatidylinositol-5-kinase; PIP, phosphatidylinositol polyphosphate; PKB, protein kinase B; PKC, protein kinase C; pl.m., plasma membrane; PLC, phospholipase C; PLD, phospholipase D; PP, protein phosphatase; PTB, phosphotyrosine-binding domain; PTEN, phosphatase and tensin homolog; Pyk, pro-line-rich tyrosine kinase; RabSa, RAS-associated protein RABSa; Raf, v-raf-1 murine leukemia viral oncogene homolog; Ras, rat sarcoma viral oncogene homolog; RasGAP, Ras GTPase-activating protein; Rb, retinoblas-toma; RGS, regulator of G-protein signaling; Rin, Ras interaction; RN-tre, related to the N-terminus of tre; RSK, ribosomal protein S6 kinase; RYR, ryanodine receptor; S, serine; SIP, sphingosine-1-phosphate; S1P1/2/3, sphingo-lipid G protein-coupled receptor 1/2/3; SERCA, sarcoplas-mic/endoplasmic reticulum calcium ATPase; Shc, Src homology 2 domain containing transforming protein; SHP, Shp-2 tyrosine phosphatase; SOS, son of sevenless homolog; SPRY, Sprouty; STAT, signal transducer and acti-vator of transcription; T, threonine; TGFα, transforming growth factor alpha; Ubc, ubiquitin-conjugating enzyme; Y, tyrosine (Oda, K et al. *Molecular Systems Biology* 2005). Thus, it is anticipated that antibody and NTKI combination therapies targeting EGFR and its downstream effectors may serve as therapies to a wide range of diseases and disorders.

Ras Proteins

Ras proteins are proto-oncogenes that are frequently mutated in human cancers. They are encoded by 3 ubiqui-tously expressed genes: HRAS, KRAS, and NRAS. These proteins are GTPases that function as molecular switches in regulating pathways that are responsible for proliferation and cell survival. KRAS (Kirsten rat sarcoma viral oncogene homolog) mutations are present in more than 25% of all human tumors, and KRAS is one of the most frequently activated oncogenes. Studies during the last quarter century have characterized the Ras proteins as essential components of signaling networks controlling cellular proliferation, dif-ferentiation, or survival. The oncogenic mutations of the H-ras, N-ras, or K-ras genes frequently found in human tumors are known to throw off balance the normal outcome of those signaling pathways, thus leading to tumor devel-opment. Oncogenic mutations in a number of other upstream or downstream components of Ras signaling pathways (in-cluding membrane RTKs or cytosolic kinases) have been detected more recently in association with a variety of cancers. Interestingly, the oncogenic Ras mutations and the mutations in other components of Ras/MAPK signaling pathways appear to be mutually exclusive events in most tumors, indicating that deregulation of Ras-dependent sig-naling is the essential requirement for tumorigenesis. Finally, even without being a causative force, defective Ras signaling has been cited as a contributing factor to many other human illnesses, including diabetes and immunologi-cal and inflammatory disorders. KRAS G12S, KRAS G12C, KRAS G13D, KRAS G12D, and NRAS Q61K are exem-plary mutations, among others, known to cause uninhibited growth and cell division demonstrative of carcinomas.

PIK3CA

Phosphoinositide kinases (PIKs) are lipid kinases that phosphorylate the inositol ring of phosphoinositides, thus acting as signal transducers, and which are mutated in a variety of human cancers. Depending on the phosphory-lation site on the carbohydrate, PIKs are categorized into three families: phosphoinositide 3-kinases (PI3Ks), phos-phoinositide 4-kinases (PIP4Ks) and phosphoinositide 5-ki-nases (PIP5Ks). It is estimated that PIK3CA is somatically mutated in 32% of colorectal cancers, 40% of human breast cancers, 12% of ovarian cancers, and 36% of uterine endometrioid cancers. In the brain, PIK3CA mutations are found in 14% of anaplastic oligodendrogliomas, 5% of GBMs, 5% of medulloblastomas, and 3% of anaplastic astrocytomas. PIK3CA E545K is an exemplary mutation known to con-tribute to carcinoma growth.

BRAF

B-Raf proto-oncogene, serine/threonine kinase is involved in many cellular processes, including cell prolif-eration, differentiation, and transcriptional regulation. BRAF is estimated to be altered in 5% of all colon adeno-carcinoma, cutaneous melanoma, lung adenocarcinoma, melanoma, and thyroid gland papillary carcinoma. BRAF V600E and BRAF G596R, among others, are further exem-plary mutations known to drive carcinomas.

KRAS, NRAS, PIK3CA, and BRAF proteins downstream of EGFR are exemplary proteins wherein mutations provide resistance to TKIs targeting EGFR and NTKIs targeting EGFR effectors. It is contemplated that in some embodi-ments, mutations in other growth factor signaling pathways may play a similar compensatory role in providing resis-tance to NTKIs.

Synthetic Proteins/Molecules

The present disclosure provides a homogeneous synthetic protein/molecule for improving the presentation of the maxi-mum number of growth factor epitopes, tumor antigen epitopes, and/or receptor binding sites as elements of an immunogenic synthetic protein/molecule. In one illustrative embodiment, a synthetic protein/molecule expressing all or portions of an immunogenic carrier domain (e.g., cholera toxin B (CT-B)), and a synthetic epidermal growth factor (sEGF), and/or a receptor is described. In alternative illus-trative embodiments, the protein may express other immu-nogenic synthetic or recombinant proteins/molecules that are modeled based upon known immunogenic proteins. It is contemplated within the scope of the disclosure that such synthetic proteins/molecules may express polypeptides that are highly immunogenic to the human immune system. Preferably, the synthetic proteins/molecules confer addi-tional properties to the chimeric protein such as, for example, high expression yield and ease of manufacture, oral stability and the ability to cross from gut to blood stream, and/or previous safe use in humans.

In an illustrative embodiment, the synthetic proteins/molecules disclosed herein may include or express growth factor epitopes as multiple copies of a whole or part of a single growth factor, or copies of whole or part of more than one different growth factor. These growth factor epitopes may be naturally occurring or synthetic (e.g., artificial). For example, BVN22E (hereinafter IN01), an illustrative non-natural synthetic protein (NNSP) described herein, may have a molecular weight of about 120 kD. IN01 (SEQ ID NO: 2) consists of two repeated synthetic EGF (Targeted Signaling Pathway (SEQ ID NO: 7) domains, Glycine-Serine repeat linkers, and a CTB sequence (SEQ ID NO: 9). In illustrative embodiments, the growth factor epitopes described herein may correspond to one or more domains within the growth factor (e.g., EGF targeted signaling path-way (TSP) domains).

According to the disclosure, the expressed growth factor epitopes should be folded in a manner that allows their natural conformation to be substantially retained and pre-sented to components of the host immune system in such a way as to elicit a robust host immune response to the epitopes. Such epitope folding may be facilitated by suitable naturally occurring proteins that support the ability of a domain or domains within a synthetic proteins/molecules to properly fold and induce an immune response and may include, but are not limited to, cholera toxin B sub-unit, *E. coli* heat-labile LT and LT-II enterotoxin B subunits, vera-toxin, pertussis toxin, *C. jejuni* enterotoxin, Shiga toxin, listeria toxin, tetanus toxoid, diphtheria toxoid, N. menin-gitidisl outer membrane protein, bacteriophage coat protein, adenovirus and other viral coat proteins. As described herein, non-natural synthetic polypeptides (e.g., BVN22E, IN01) may be used that fulfill the requirements of conferring immunogenicity to the whole protein and allowing appro-priate folding and presentation of growth factors, receptors, tumor antigens or epitopes thereof to the host immune system.

According to the disclosure, the synthetic proteins/mol-ecules provided herein—whether growth factors or parts thereof, cellular receptors or parts thereof, or tumor antigens or parts thereof—are related to a broad range of cellular pathways involved in chronic disease, growth factor based or receptor based cancers, and/or solid tumors for use as tumor antigens within the said synthetic proteins. The pro-teins are in the form of a synthetic proteins/molecules and may be useful in treating chronic diseases, for example, breast, lung, bladder, ovarian, vulva, colonic, pulmonary, brain, colorectal, intestinal, head and neck, and esophagus cancers.

EGFR-EFFECTOR NTKI Compounds

As described herein, such EGFR-EFFECTOR NTKI compounds inhibit kinases downstream of EGFR, and are useful for the treatment of neoplasias, such as non-small cell lung carcinoma and colon adenocarcinoma, particularly in combination with an alkylating agent, such as cisplatin. Without wishing to be bound by theory, these combination therapies may be particularly effective against neoplastic cells because they reduce or eliminate the ability of the neoplastic cells to become resistant to the NTKIs.

In certain embodiments, a compound of the invention can prevent, inhibit, or disrupt, or reduce by at least 10%, 25%, 50%, 75%, or 100% the activity of an EGFR effector kinase.

In certain embodiments, a compound of the invention is a small molecule having a molecular weight less than about 1,300 daltons, less than 1000 daltons, less than 800 daltons, less than 600 daltons, less than 500 daltons, less than 400 daltons, or less than about 300 daltons. Examples of com-pounds of the invention include EGFR-EFFECTOR NTKI compounds of the disclosure may include, but are not limited to, Trametinib, Taselisib, Alpelisib, Copanlisib, Ide-alisib, Duvelisib, Buparlisib, Umbralisib, PX-866 Dac-tolisib, CUDC-907, Voxtalisib (SAR245409, XL765) ME-401, IPI-549, SF1126, INK1117 Pictilisib, XL147 (SAR245408), GSK1059615, ZSTK474, PWT33597, IC87114, TG100-115, CAL 263, RP6503, GNE-477 AEZS-136, Vemurafenib, Dabrafenib, GDC-0879, PLX-4720 Cobimetinib, Binimetinib, Selumetinib, PD-325901, PD035901, CI-1040, TAK-733, Perifosine, Palomid 529 are other exemplary non-tyrosine targeting kinase inhibitors (NTKIs) targeting EGFR pathway kinases.

Trametinib (MW 615.4 g/mol) is an orally bioavailable inhibitor of mitogen-activated protein kinase kinase (MEK MAPK/ERK kinase). Trametinib specifically binds to and inhibits MEK 1 and 2, resulting in an inhibition of growth factor-mediated cell signaling and cellular proliferation in various cancers. MEK 1 and 2, dual specificity threonine/tyrosine kinases often upregulated in various cancer cell types, play a key role in the activation of the RAS/RAF/MEK/ERK signaling pathway that regulates cell growth. Trametinib is indicated for the treatment of unresectable or metastatic melanoma with BRAF V600E or V600K muta-tions, as detected by an FDA-approved test. Trametinib is a pyridopyrimidine that in extant methods is used, in DMSO, to treat patients with unresectable or metastatic melanoma with BRAF V600E or V600K mutations, and who have not received prior BRAF inhibitor treatment. Trametinib is readily absorbed. When an oral administration of trametinib was given to patients with BRAF V600 mutation-positive melanoma, peak plasma concentration occurred 1.5 hours post-dose (Tmax). A single 2 mg oral dose has a bioavail-ability of 72%. When a dose of 2 mg/day is given, the peak plasma concentration (Cmax) is 22.2 ng/mL. Trametinib is metabolized predominantly via deacetylation alone or with mono-oxygenation or in combination with glucuronidation biotransformation pathways in vitro. Deacetylation is likely mediated by hydrolytic enzymes, such as carboxyl-esterases or amidases. The predominant circulating component in the plasma is the parent drug. Elimination half-life=3.9-4.8 days. IUPAC name N-[3-[3-cyclopropyl-5-(2-fluoro-4-io-doanilino)-6,8-dimethyl-2,4,7-trioxopyrido[4,3-d]pyrimi-din-1-yl]phenyl]acetamide.

Taselisib (MW 460.5 g/mol) is an orally bioavailable inhibitor of the class I phosphatidylinositol 3-kinase (PI3K) alpha isoform (PIK3CA). Taselisib selectively inhibits PIK3CA and its mutant forms in the PI3K/Akt/mTOR pathway, which may result in tumor cell apoptosis and growth inhibition in PIK3CA-expressing tumor cells. By specifically targeting class I PI3K alpha, this agent may be more efficacious and less toxic than pan PI3K inhibitors. Dysregulation of the PI3K/Akt/mTOR pathway is fre-quently found in solid tumors and causes increased tumor cell growth, survival, and resistance to both chemotherapy and radiotherapy. PIK3CA, which encodes the p110-alpha catalytic subunit of the class I PI3K, is mutated in a variety of cancer cell types and plays a key role in cancer cell growth and invasion. IUPAC name 2-methyl-2-[4-[2-(5-methyl-2-propan-2-yl-1,2,4-triazol-3-yl)-5,6-dihydroimi-dazo[1,2-d][1,4]benzoxazepin-9-yl]pyrazol-1-yl]propena-mide.

Alpelisib (MW 441.5 g/mol) is a phosphatidylinositol 3-kinase (PI3K) inhibitor with potent antitumor activity. It works by selectively inhibiting class I PI3K p110α, which is the catalytic subunit of PI3K, a lipid kinase that plays a role in various biological processes, including proliferation, sur-vival, differentiation, and metabolism. Alpelisib was designed to target this enzyme that appears to be mutated at a rate of nearly 30% in human cancers, leading to hyperac-tivation. Approved by the FDA in May 2019, Alpelisib is the first approved PI3K inhibitor indicated for the treatment of hormone receptor (HR)-positive, human epidermal growth factor receptor 2 (HER2)-negative, PIK3CA-mutated, advanced or metastatic breast cancer for postmenopausal women and male patients. In extant methods, to initiate Alpelisib therapy, the presence of a PIK3CA mutation in the tissue and/or liquid biopsy sample collection is required via FDA-approved diagnostic tests. Alpelisib is marketed under the trade name Piqray and is available as oral tablets. Patients taking Alpelisib experience a dose dependent ben-efit from treatment with a 51% advantage of a 200 mg daily dose over a 100 mg dose and a 22% advantage of 300 mg once daily over 150 mg twice daily. Patients requiring a lower dose may benefit from twice daily dosing. The mean half-life of Alpelisib is 8 to 9 hours. IUPAC name (2S)-1-N-[4-methyl-5-[2-(1,1,1-trifluoro-2-methylpropan-2-yl) pyridin-4-yl]-1,3-thiazol-2-yl]pyrrolidine-1,2-dicarboxam-ide.

Copanlisib (MW 480.5 g/mol) is a selective pan-Class I phosphoinositide 3-kinase (PI3K/Phosphatidylinositol-4,5-bisphosphate 3-kinase/phosphatidylinositide 3-kinase)

inhibitor that was first developed by Bayer Healthcare Pharmaceuticals, Inc. The drug targets the enzyme that plays a role in regulating cell growth and survival. Copanlisib was granted accelerated approval on Sep. 14, 2017 under the market name Aliqopa for the treatment of adult patients with relapsed follicular lymphoma and a treatment history of at least two prior systemic therapies. Follicular lymphoma is a slow-growing type of non-Hodgkin lymphoma that is caused by unregulated proliferation and growth of lympho-cytes. The active ingredient in Aliquopa intravenous therapy is Copanlisib dihydrochloride. Copanlisib has demonstrated potent anti-tumor and pro-apoptotic activity in various tumor cell lines and xenograft models. In clinical trials, 59% of patients receiving Copanlisib achieved complete or partial shrinkage of their tumors after a median of 12.2 months. Higher systemic levels of Copanlisib are associated with elevated plasma glucose levels. Following a steady state exposure at 0.8 mg/kg, the mean peak plasma concentration (Cmax) of copanlisib is 463 ng/mL with the range of 105 to 1670 ng/mL. The geometric mean terminal elimination half-life of Copanlisib is 39.1 hours (range: 14.6 to 82.4; SD: 15.0). The in vitro human plasma protein binding of Copan-lisib is 84.2%, with albumin being the main binding protein. IUPAC name 2-amino-N-[7-methoxy-8-(3-morpholin-4-yl-propoxy)-2,3-dihydro-1H-imidazo[1,2-c]quinazolin-5-ylidene]pyrimidine-5-carboxamide.

Encorafenib (MW 540 g/mol), also known as BRAFTOVI, is a kinase inhibitor. Encorafenib inhibits BRAF which plays a role in regulating the MAP kinase/ERK signaling pathway, impacting cell division, differentiation, and secretion. Mutations in this gene, most frequently the V600E mutation, are the most commonly identified cancer-causing mutations in melanoma, and have been isolated in various other cancers as well, including non-Hodgkin lym-phoma, colorectal cancer, thyroid carcinoma, non-small cell lung carcinoma, hairy cell leukemia and adenocarcinoma of the lung. On Jun. 27, 2018, the Food and Drug Administra-tion approved Encorafenib and Binimetinib (BRAFTOVI and MEKTOVI, Array BioPharma Inc.) in combination for patients with unresectable or metastatic melanoma with a BRAF V600E or V600K mutation, as detected by an FDA-approved test. After oral administration, the median Tmax of encorafenib is 2 hours. At least 86% of the dose is absorbed. The apparent clearance is 14 L/h (54%) at day 1, increasing to 32 L/h (59%) at steady-state. IUPAC name is methyl N-[(2S)-1-[[4-[3-[5-chloro-2-fluoro-3-(methanesulfona-mido)phenyl]-1-propan-2-ylpyrazol-4-yl]pyrimidin-2-yl] amino]propan-2-yl]carbamate.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as alumi-num and zinc; ammonia, and organic amines, such as unsubstituted or hydroxy substituted mono, di, or trialky-lamines; dicyclohexylamine; tributyl amine; pyridine; N methyl,N ethylamine; diethylamine; triethylamine; mono, bis, or tris (2 hydroxy lower alkyl amines), such as mono, bis, or tris (2 hydroxyethyl)-amine, 2 hydroxy tert butylam-ine, or tris (hydroxymethyl)methylamine, N, N, di lower alkyl N (hydroxy lower alkyl) amines, such as N,N dimethyl N (2 hydroxyethyl)-amine, or tri (2 hydroxyethyl)amine; N methyl D glucamine; and amino acids such as arginine, lysine, and the like. The term "pharmaceutically acceptable salt" also refers to a salt prepared from a compound dis-closed herein, e.g., NSC-30049, having a basic functional group, such as an amino functional group, and a pharma-ceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-tolu-enesulfonic acid.

Adjuvant

Certain illustrative embodiments as provided herein include composition and method of use of synthetic pro-teins/molecules according to the disclosure within vaccine compositions and immunological adjuvant compositions, including pharmaceutical compositions, that contain, in addition to synthetic proteins/molecules at least one adju-vant, which refers to a component of such compositions that has adjuvant activity. An adjuvant having such adjuvant activity includes a composition that, when administered to a subject such as a human (e.g., a human patient), a non-human primate, a mammal or another higher eukaryotic organism having a recognized immune system, is capable of altering (i.e., increasing or decreasing in a statistically significant manner, and in certain preferred embodiments, enhancing or increasing) the potency and/or longevity of an immune response. In certain illustrative embodiments dis-closed herein a desired antigen and or antigens contain within a protein carrier, and optionally one or more adju-vants, may so alter, e.g., elicit or enhance, an immune response that is directed against the desired antigen and or antigens which may be administered at the same time or may be separated in time and/or space (e.g., at a different anatomic site) in its administration, but certain illustrative embodiments are not intended to be so limited and thus also contemplate administration of synthetic proteins/molecules in a composition that does not include a specified antigen but which may also include but is not limited to one or more co-adjuvant, an imidazoquinline immune response modifier.

Pharmaceutical Compositions

In certain illustrative embodiments, the pharmaceutical composition is a vaccine composition that comprises both the synthetic proteins/molecules according to the disclosure and may further comprise one or more components, as provided herein, that are selected from TLR agonist, co-adjuvant (including, e.g., a cytokine, an imidazoquinoline immune response modifier and/or a dSLIM) and the like and/or a recombinant expression construct, in combination with a pharmaceutically acceptable carrier, excipient or diluent.

Illustrative carriers will be nontoxic to recipients at the dosages and concentrations employed. For vaccines com-prising synthetic proteins/molecules, about 0.01 µg/kg to about 100 mg/kg body weight will be administered, typi-cally by the intradermal, subcutaneous, intramuscular or intravenous route, or by other routes. In embodiments, vaccines comprising synthetic proteins/molecules may be administered from about 0.01-0.1 µg/kg to about 95 mg/kg body weight; or from about 0.1-1.0 µg/kg to about 90 mg/kg body weight; or from about 0.5-5.0 µg/kg to about 80 mg/kg body weight; or from about 1.0-10.0 µg/kg to about 60 mg/kg body weight; or from about 5.0-20.0 µg/kg to about 50 mg/kg body weight; or from about 20-50 µg/kg to about 25 mg/kg body weight; or from about 50-100 µg/kg to about 20 mg/kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 µg/kg body weight.

It will be evident to those skilled in the art that the number and frequency of administration will be dependent upon the response of the host. "Pharmaceutically acceptable carriers" for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic sonophoretic, passive transdermal, microneedle administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, a pharmaceutical or vaccine composition of the invention comprises a stable aqueous suspension of less than 0.2 um and further comprises at least one component selected from the group consisting of phospholipids, fatty acids, surfactants, detergents, saponins, fluorodated lipids, and the like.

It may also be desirable to include other components in a vaccine or pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Pharmaceutical compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product may be formulated as a lyophilizate using appropriate excipient solutions (e.g., sucrose) as diluents.

In an illustrative embodiment, the epitope or receptor supporting domain of the synthetic protein/molecule, whether derived from a natural or synthetic polypeptide sequence, should have the capacity to self-assemble into oligomeric multimers under appropriate chemical/environmental conditions, or to be reduced to monomers under alternative conditions. Ideally, multimerisation domains will assemble into stable multimers with a discreet number of sub-units, for example dimers, trimers, tetramers, pentamers, etc., such that a product of homogeneous size is generated. Examples of natural polypeptides include, but are not limited to, leucine zippers, lac repressor protein, streptavidin/avidin, cholera toxin B sub-unit, Pseudomonas trimerization domain, and viral capsid proteins.

In one illustrative embodiment the anti-EGF antibodies used in the pre-clinical studies are actively produced by immunizations with a rEGF-rP64k conjugate, CIMAvax- EGF vaccine as described in *Manufacturing Process Development for an Epidermal Growth Factor-Based Cancer Vaccine*, Rodriguez et al., (Supplement to Biopharm International October 2008, the contents of which are incorporated in their entirety by reference) formulated with Montanide adjuvant. It is contemplated within the scope of the disclosure that other vaccine formulations that produce an immune response to EGF or EGFR may be used. It is also within the Scope of the disclosure that vaccines producing an immune response to other growth factors or their receptors may also be used. In particular, immunogenic proteins as set forth in WO2013/076580 and WO2014/140894, the content of each incorporated in their entirety by reference, may be used to produce anti-EGF antibodies according to the disclosure.

Formulation of Therapeutic NTKI Compositions

The administration of a compound (e.g., a NKTI) in combination with a non-natural synthetic polypeptide (e.g., IN01) for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 μg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Although the instant disclosure suggests ranges of dosing, one skilled in the art would understand that any therapeutically effective dose as set forth in the product labeling is within the scope of this disclosure. Likewise, any dosing that is based upon the understanding and knowledge of a medical practitioner in the field of oncology is contemplated within the scope of the disclosure.

Selection of a Treatment Method

After a subject is diagnosed as having a neoplasia (e.g., NSLC or CRC) a method of treatment is selected. In colorectal cancer (CRC), for example, a number of standard treatment regimens are available. In general, CRCs are one of the most aggressive forms of cancer, and advanced CRCs are rarely susceptible to conventional treatment methods. For aggressive CRC, few therapeutic options are available, and such tumors often correlate with poor clinical outcomes, such as metastasis or death. A subject having aggressive CRC is identified as likely to benefit from treatment with a composition of the invention comprising a non-natural synthetic polypeptide (NNSP) of IN01 or antibody thereof, in combination with Trametinib, Taselisib, Alpelisib, Copanlisib, and/or Encorafenib. Thus, the invention provides methods for selecting a therapy for a subject, the method involving identifying a subject as having aggressive neoplasia, such as CRC, or aggressive forms of NSLC or glioblastoma, and administering to the subject a therapeutic combination of the invention.

Even when a subject with neoplasia (e.g., colon cancer, lung cancer, and brain cancer, such as glioblastoma) is identified as having a good clinical outcome, the subject is also likely to benefit from treatment with the methods of the invention (e.g., lower side effects). When methods of the invention indicate that a neoplasia is very aggressive, an aggressive method of treatment should be selected. Aggressive therapeutic regimens typically include one or more of the following therapies: radical mastectomy, radiation therapy, hormone therapy, and chemotherapy. Such methods may be used in combination with the therapeutic methods described herein, particularly for the treatment of pancreatic cancer, which is prone to relapse.

While the homogeneous synthetic proteins/molecules expressing or incorporating one or more tumor antigens, synthetic growth factors, and/or receptors have been described and illustrated in connection with certain embodiments, many variations and modifications will be evident to those skilled in the art and may be made without departing from the spirit and scope of the disclosure. The disclosure is thus not to be limited to the precise details of methodology or construction set forth above as such variations and modification are intended to be included within the scope of the disclosure.

It is contemplated that any order of administration of the non-natural synthetic polypeptide (NNSP) of IN01 or antibody thereof, relative to the NTKI Trametinib, Taselisib, Alpelisib, Copanlisib, and/or Encorafenib may be preferred in treating a patient. For example, it may be beneficial to administer the non-natural synthetic polypeptide of IN01 or antibody thereof prior to administering the NTKI, e.g. Trametinib, Taselisib, Alpelisib, Copanlisib, and/or Encorafenib. It may also be beneficial to administer the Trametinib, Taselisib, Alpelisib, Copanlisib, and/or Encorafenib prior to administering the non-natural synthetic polypeptide of IN01 or antibody thereof.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "isolated" or "partially purified" as used herein refers, in the case of a nucleic acid or polypeptide, to a nucleic acid or polypeptide separated from at least one other component nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more.

As used herein, the terms "proteins" and "polypeptides" are used interchangeably herein to designate a series of amino acid residues connected to the other by peptide bonds between the alpha-amino and carboxy groups of adjacent residues. The terms "protein", and "polypeptide", which are used interchangeably herein, refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein the term, "Antibody" includes any immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab').sub.2, and Fv fragments), single chain Fv (scFv) mutants, multi-specific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as cytotoxics, toxins, radioisotopes, etc. Antibodies can be administered by actively producing them in vivo or passive administering monoclonal antibodies.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called a, 6, £, y, and 11, and respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population comprise essentially identical amino acid sequence except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

A "pharmaceutical excipient" shall mean those commonly utilized within the pharmaceutical art and in particular those found "Handbook of excipients", (Raymond C. Rowe, Paul J. Sheskey, Paul J. Weller-4th Edition, 2003), the contents of which are incorporated in their entirety.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, *Chem Intl. Ed. Engl.,* 33: 183-186 (1994)); dynemicin, including dynemicin A; an espmeramicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HC1 liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, drom ostanol one propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifo sfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromefthylomithine (DMF0); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

"Patient response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of cell proliferation, invasion or metastasis, which may, but does not have to, result in the regression or ablation of a disease lesion; (7) relief, to some extent, of one or more symptoms associated with the disorder; (8) increase in the length of disease-free presentation following treatment; and/or (9) decreased mortality at a given point of time following treatment.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

The efficacy of a given treatment for cancer can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein. An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc. In addition, efficacy of an agent can be measured by a decrease in circulating MIC peptides or fragments thereof in a subject being treated with an agent comprising an antibody or antigen-binding portion thereof as described herein or a nucleic acid encoding an antibody or antigen-binding portion thereof as described herein.

Kits or Pharmaceutical Systems

The present compositions may be assembled into kits or pharmaceutical systems for use in ameliorating a neoplasia (e.g., CRC or NSLC). Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using the agents of the invention. Kits of the invention include at least one or more alkylating agents (e.g., cisplatin, and at least one or more agents that bind to an EGFR effector kinase, e.g. Trametinib, in combination with an IN01 non-natural synthetic polypeptide and/or an anti-IN01 antibody, thereby reducing the activity of both EGFR and MEK proteins. If desired, the kit also includes an agent that binds to ribonucleotide reductase (RR) and reduces nucleotide synthesis (e.g., gemcitabine). The kit may include instructions for administering the alkylating agent in combination with one or more agents that bind to an EGFR effector kinase, e.g. Trametinib, in combination with an IN01 non-natural synthetic polypeptide (NNSP) and/or an anti-IN01 antibody, reducing the activity of both EGFR and MEK proteins, thereby increasing the efficacy of the alkylating agent relative to the efficacy of the alkylating agent administered alone. Methods for measuring the efficacy of alkylating agents are known in the art and are described herein (e.g., measuring the IC50).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The present disclosure is further illustrated by the following examples, which should not be construed as limiting. The contents of all references, GenBank Accession and Gene numbers, and published patents and patent applications cited throughout the application are hereby incorporated by reference. Those skilled in the art will recognize that the disclosure may be practiced with variations on the disclosed structures, materials, compositions and methods, and such variations are regarded as within the scope of the disclosure.

Figures 1, 2:
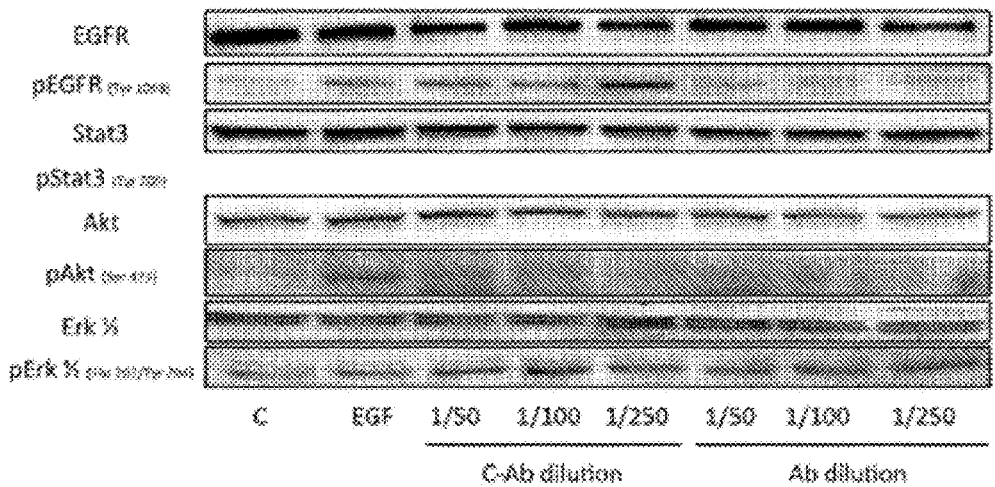
FIG. 1 shows the cell line name and origin of several KRAS mutation carrying cell lines. DLD1 and LS174T cell lines also carry PIK3CA mutations.
FIG. 2 shows the effect on pEGFR, pStat3, pAkt, and pErk ½ signaling, assessed by western blot, of 2 hour incubation with different concentrations of the anti-IN01 therapeutic antibody, "Ab," or a control antibody, "C-Ab," in DLD1 cells.
Figure 3:
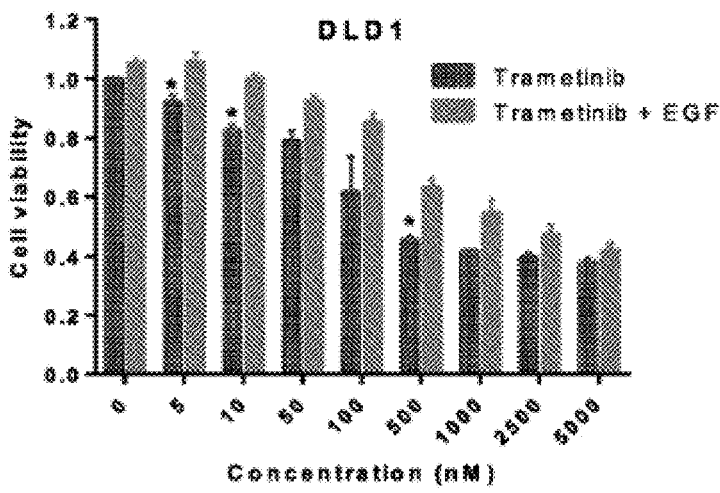
FIG. 3 shows the effect of 3 day incubation of different concentrations of Trametinib on DLD1 cell viability, with and without EGF.
Figure 4:
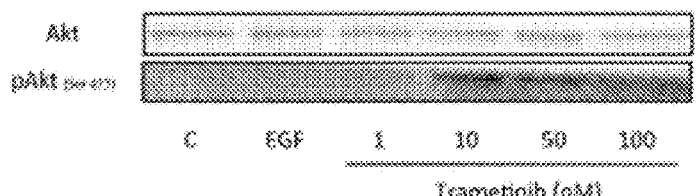
FIG. 4 shows the effect on pEGFR, pStat3, pAkt, and pErk ½ signaling, assessed by western blot, of 2 hour incubation with EGF or different concentrations of Trametinib in DLD1 cells.
Figure 4:
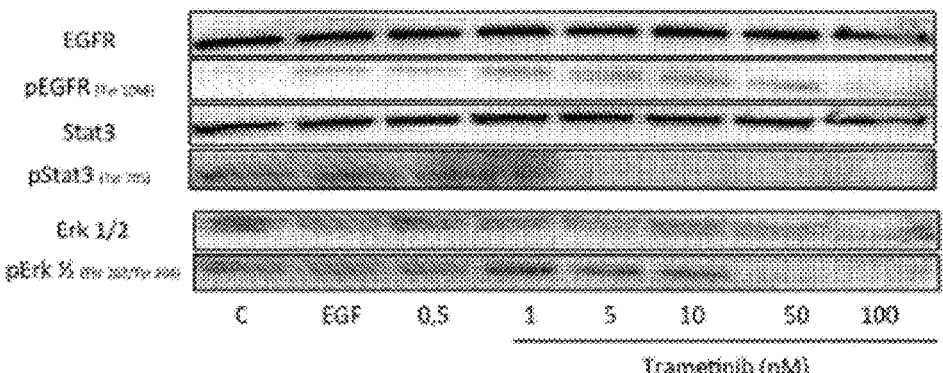
Figure 5A:
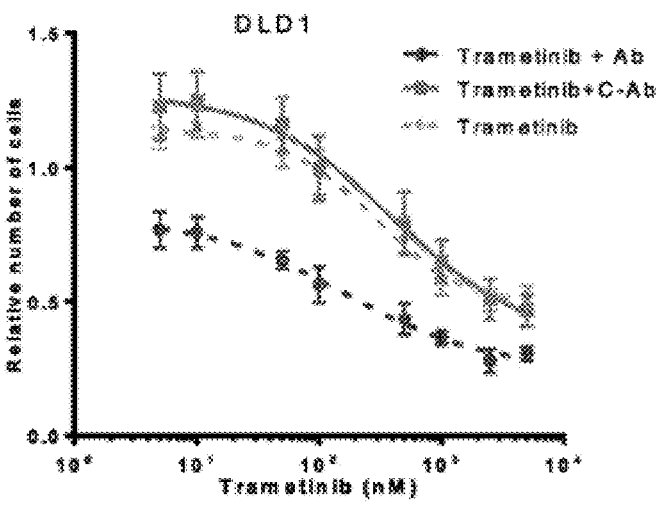
FIGS. 5A-5B show the effect of anti-IN01 in combination with Trametinib on DLD1 cell viability.
Figure 5B:
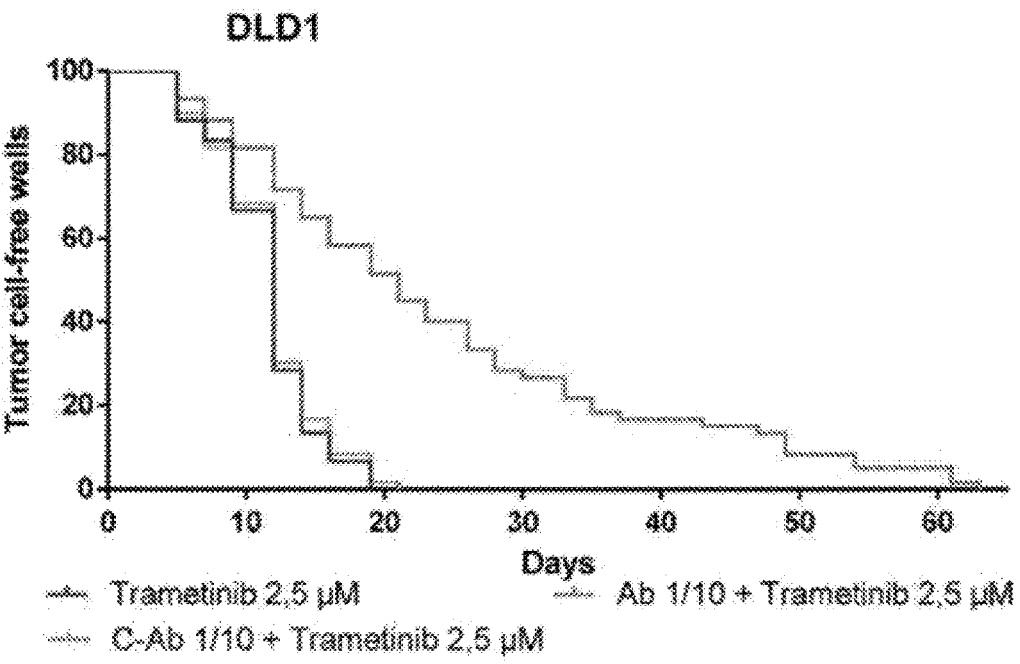

Example 1: DLD1 (G13D KRAS) and LS174T (G13D KRAS) KRAS Mutant Cell Lines Response to Anti-IN01 Antibody NTKI Combination Therapies The anti-IN01 (BVN22E) antibody was developed from SEQ ID NO: 2, which consists of two repeated synthetic EGF Targeted Signaling Pathway (SEQ ID NO: 7) domains, Glycine-Serine repeat linkers, and a CTB sequence (SEQ ID NO: 25). The anti-IN01 antibody was developed to be used in combination with non-tyrosine targeting kinase inhibitors targeting EGFR downstream effectors in order to inhibit cancer cell growth. In this example, KRAS mutation carrying cell lines DLD1, which carries a G13D mutation in KRAS and an E545K mutation in PIK3CA, and LS174T which carries a G12D mutation in KRAS and a mutation in PIK3CA were used (FIGS. 1 and 43).

Figure 6:
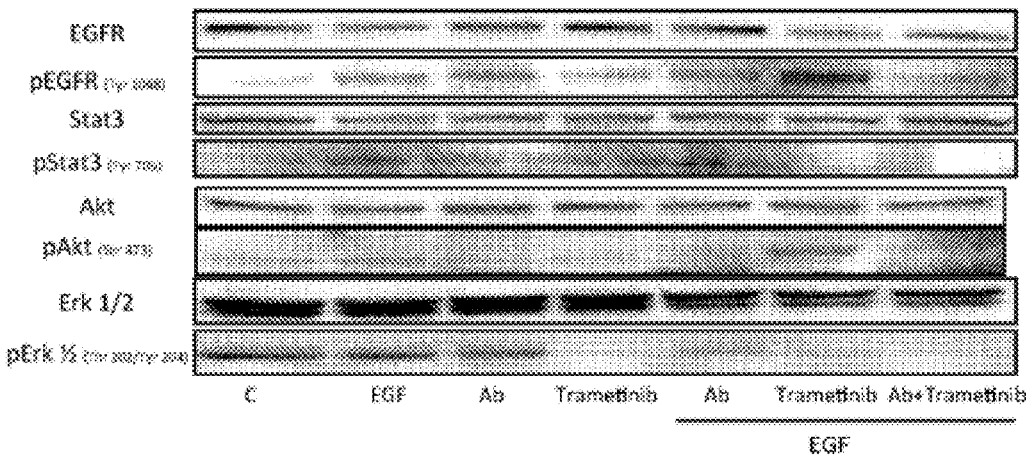
FIG. 6 shows the effect on pEGFR, pStat3, pAkt, and pErk ½ signaling, assessed by western blot, of 2 hour incubation with EGF, 10 nM Trametinib, and the anti-IN01 antibody, referred to as "Ab," or a control antibody, referred to as "C," alone or in combination, in DLD1 cells.
Figure 7:
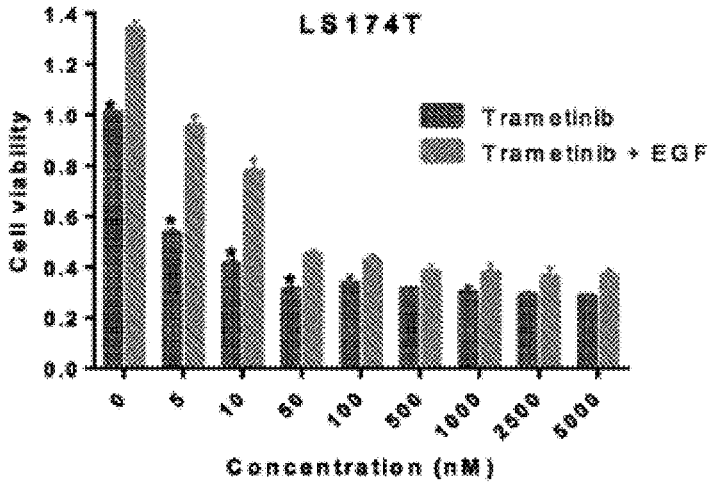
FIG. 7 shows the effect of 3 day incubation of different concentrations of Trametinib on LS174T cell viability, with and without EGF.
Figure 8:
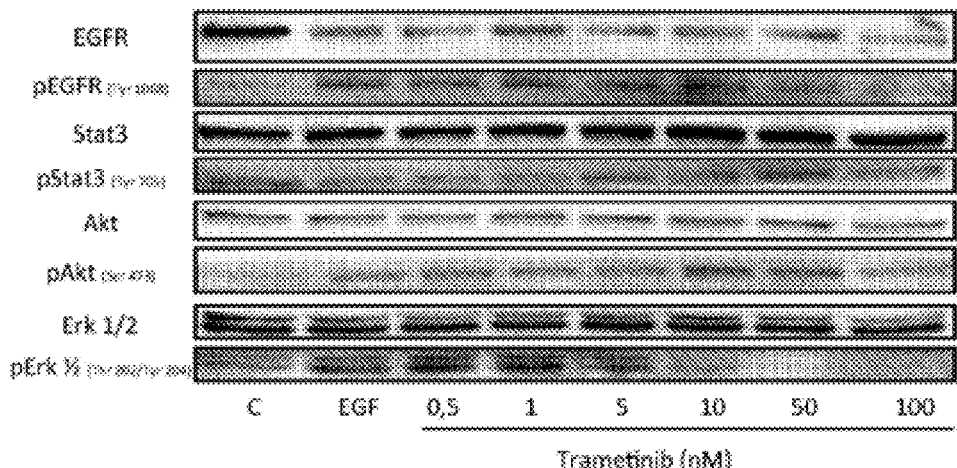
FIG. 8 shows the effect on pEGFR, pStat3, pAkt, and pErk ½ signaling, assessed by western blot, of a 2 hour incubation with EGF or different concentrations of Trametinib in LS174T cells.
Figure 9:
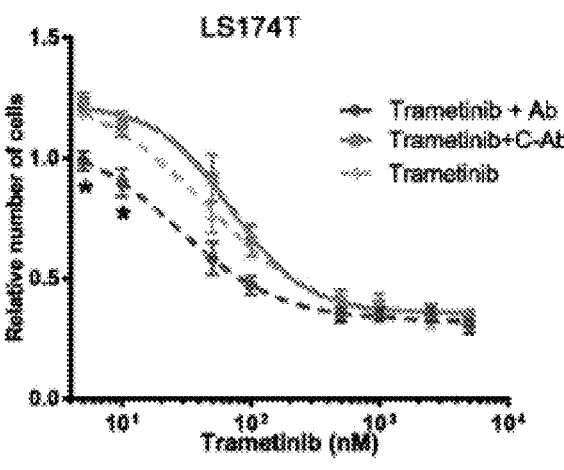
FIG. 9 shows the effect of a 3 day incubation with the anti-IN01 therapeutic antibody, or a control antibody, C-Ab, used in combination with different concentrations of Trametinib on LS174T cell viability.
Figure 29:
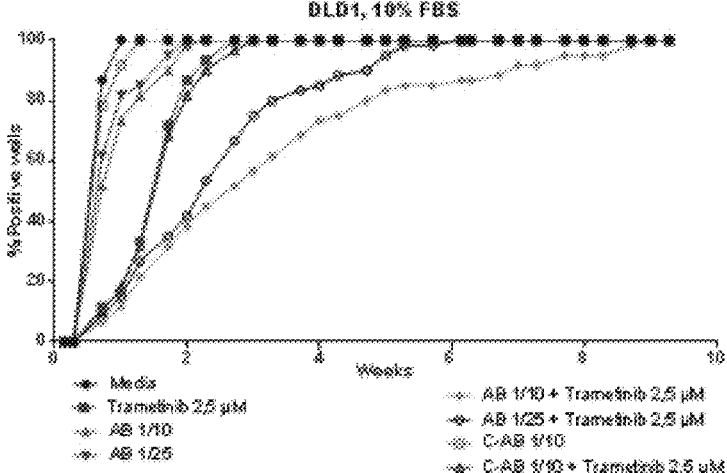
FIG. 29 shows the emergence of resistance over time of DLD1 cells in response to treatment with the anti-IN01 antibody and a control antibody, in combination with 2.5 mM Trametinib.
Figures 44, 45:
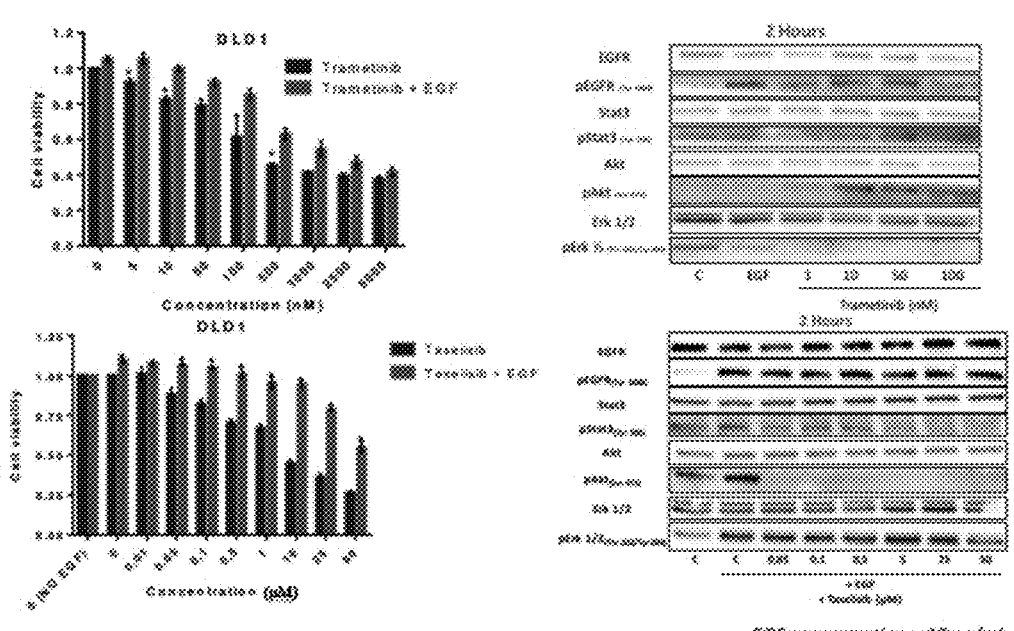
FIG. 44 shows exemplary kinase inhibitors used in the instant application.
FIG. 45 shows the effects of Trametinib and Taselisib with and without EGF in DLD1 cells. Top, left, shows the effect of 3 day incubation of different concentrations of Trametinib on DLD1 cell viability, with and without EGF. Top, right, shows the effect on pEGFR, pStat3, pAkt, and pErk½ signaling, assessed by western blot, of a 2 hour incubation with EGF and different concentrations of Trametinib in DLD1 cells. Bottom, left, shows the effects of a 3 day incubation of different concentrations of Taselisib on DLD1 cell viability, with and without EGF. Bottom, right, shows the effect on pEGFR, pStat3, pAkt, and pErk½ signaling, assessed by western blot, of a 2 hour incubation with EGF and different concentrations of Taselisib in DLD1 cells.
Figure 46:
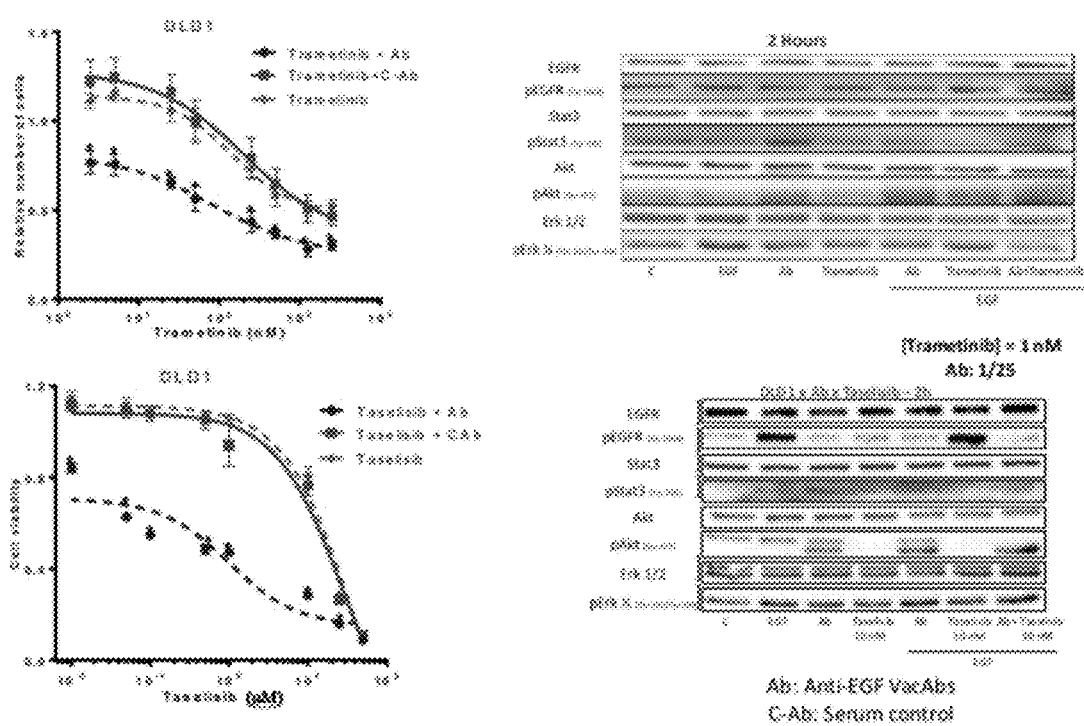
FIG. 46 shows effects of antibody and kinase inhibitor combination therapy in DLD1 cells. Top, left, shows the effects of a 3 day incubation with the anti-IN01 therapeutic antibody, or a control antibody, C-Ab, used in combination with different concentrations of Trametinib on DLD1 cell viability. Top, right, shows the effects on pEGFR, pStat3, pAkt, and pErk½ signaling, assessed by western blot, of a 2 hour incubation with EGF, the anti-IN01 antibody, referred to as "Ab," and Trametinib, alone or in combination, in DLD1 cells. Bottom, left, shows the effects of 3 day incubation of different concentrations of Trametinib in combination with the anti-IN01 therapeutic antibody, "Ab," or a control antibody, "C-Ab," used in combination with Taselisib. Bottom, right, shows the effects on pEGFR, pStat3, pAkt, and pErk½ signaling, assessed by western blot, of a 2 hour incubation with EGF, the anti-IN01 antibody, referred to as "Ab," and Taselisib, alone or in combination, in DLD1 cells.
Figure 47:
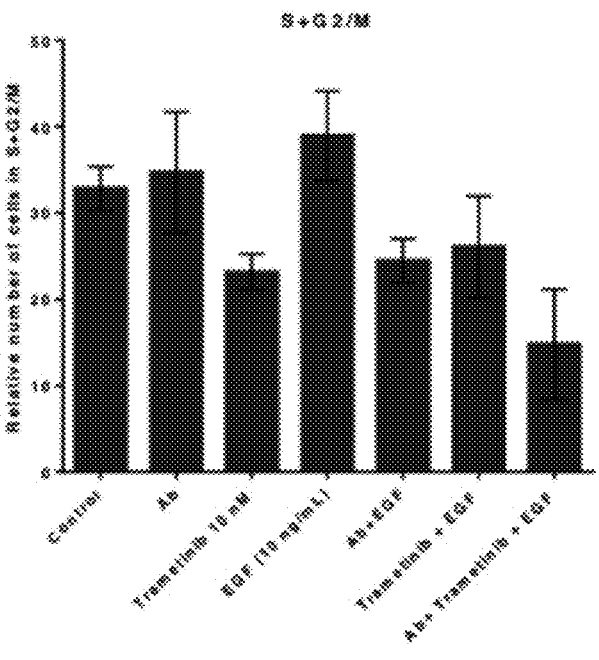
FIG. 47 shows the effects of 10 nM Tramentinib, EGF, and the anti-IN01 antibody, in combination and alone, on the S and G2/M phases of the cell cycle in DLD1 cells.
Figure 48:
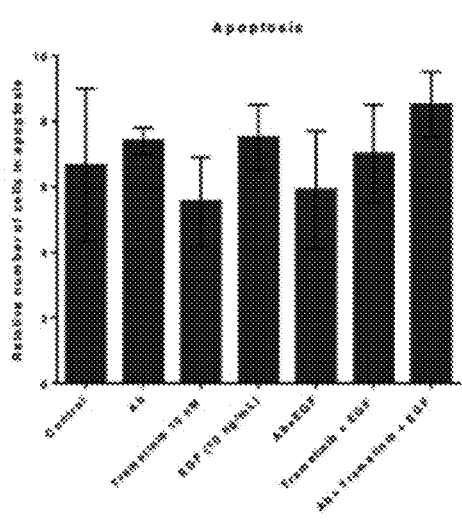
FIG. 48 shows the effects of 10 nM Tramentinib, EGF, and the anti-IN01 antibody, in combination and alone, on apoptosis in DLD1 cells.
Figure 49:
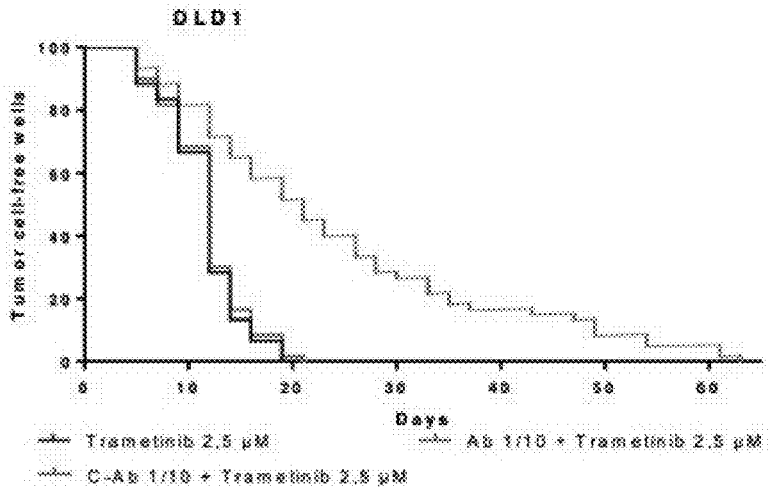
FIG. 49 shows the emergence of resistance over time to Trametinib, with Trametinib alone or in combination with the anti-IN01 antibody, referred to as "Ab," or a control antibody, referred to as "C," in DLD1 cells.
Figure 50:
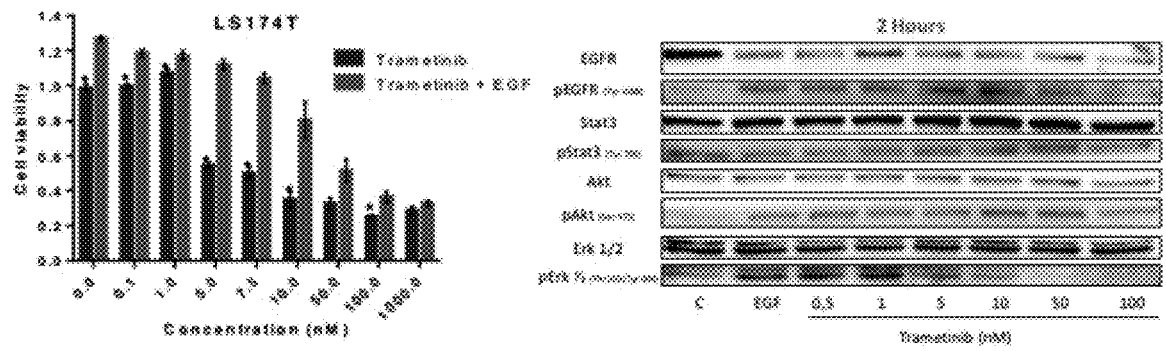
FIG. 50 shows the effects of Trametinib with and without EGF in LS174T cells. Left, shows the effect of 3 day incubation with different concentrations of Trametinib on LS174T cell viability, with and without EGF. Right, shows the effect on pEGFR, pStat3, pAkt, and pErk½ of 2 hour incubation of EGF and different concentrations of Trametinib in LS174T cells.
Figure 51:
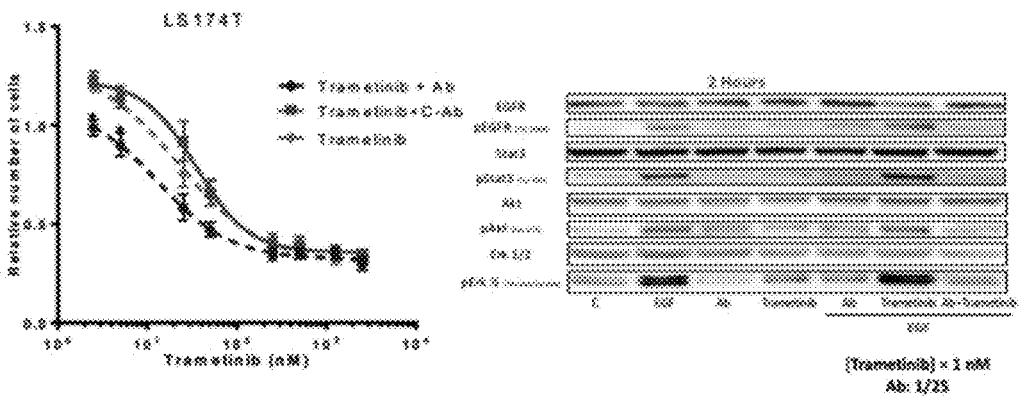
FIG. 51 shows the effects of Trametinib in combination with the anti-IN01 antibody in LS174T cells. Left, shows the effects of 3 day incubation with different concentrations of Trametinib, alone and in combination with the anti-IN01 antibody, referred to as "Ab," or a control antibody, referred to as "C," on LS174T cell viability. Right, shows the effects on pEGFR, pStat3, pAkt, and pErk ½ signaling, assessed by western blot, of a 2 hour incubation with EGF, 1 nM Trametinib, and/or the anti-IN01 antibody, referred to as "Ab," or a control antibody, referred to as "C," in LS174T cells. The anti-IN01 Ab was diluted 1:25 for these experiments.
Figure 52:
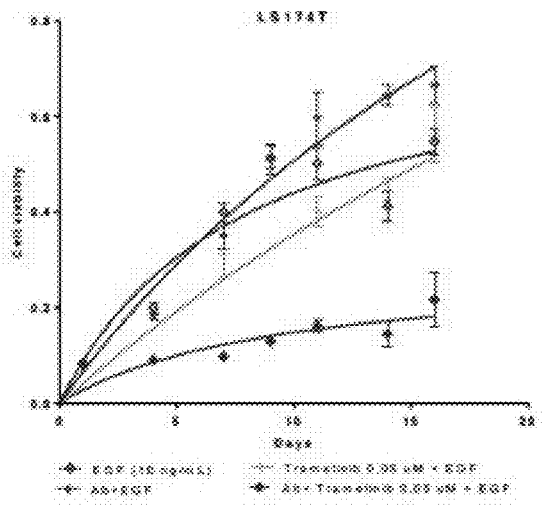
FIG. 52 shows the longer term effects on LS174T cell viability of the anti-IN01 therapeutic antibody, or a control antibody, C-Ab, used in combination with 0.05 mM Trametinib.

FIGS. 2-6 show the effects of the anti-IN01 antibody in combination with Trametinib in DLD1 cells. Phosphorylation of EGFR is strongly inhibited by the anti-IN01 antibody. The combination of anti-IN01 antibody with Trametinib enhances the effect of Trametinib alone, in that there is significant effect on pEGFR and pERK1/2 activation (FIG. 6). The combined therapy also has a pronounced effect on pSTAT3 and pAKT (FIG. 6). FIGS. 29 and 49 show that over time resistance to Trametinib develops, but is lessened by the anti-IN01 antibody. FIG. 45 shows that DLD1 cells demonstrate similar cell signaling responses to Taselisib and Trametinib. FIG. 46 shows that the anti-IN01 antibody greatly decreases cell viability of DLD1 cells in combination with either Trametinib or Taselisib.

Figure 30:
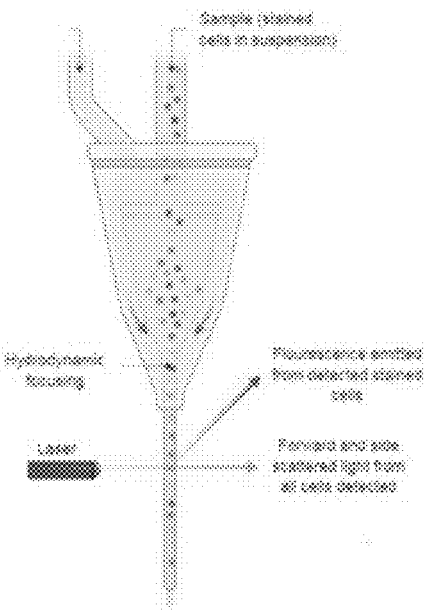
FIG. 30 shows a diagram of cell cycle and apoptosis determination via flow cytometry, wherein the sample cells are stained in suspension, and the stained cells are detected via fluorescence excitation.

FIGS. 33, 34, 47, and 48 show that the number of DLD1 cells in S and G2/M phases was lower with anti-IN01 and Trametinib combination therapy, and the number of DLD1 cells in apoptosis was higher, as assessed by flow cytometry (FIG. 30).

Figure 10:
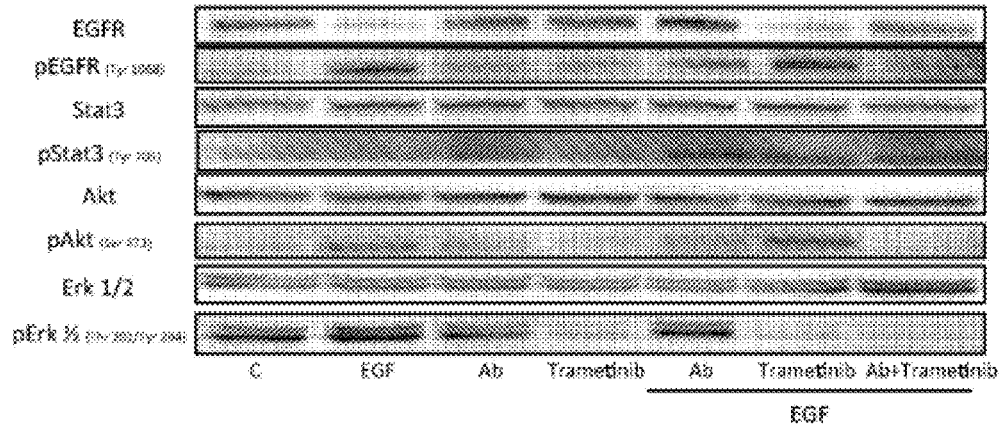
FIG. 10 shows the effect on pEGFR, pStat3, pAkt, and pErk ½ signaling, assessed by western blot, of a 2 hour incubation with EGF, 5 nM Trametinib, and/or the anti-IN01 antibody, referred to as "Ab," or a control antibody, referred to as "C," in LS174T cells. The anti-IN01 Ab was diluted 1:10 for these experiments.
Figure 11:
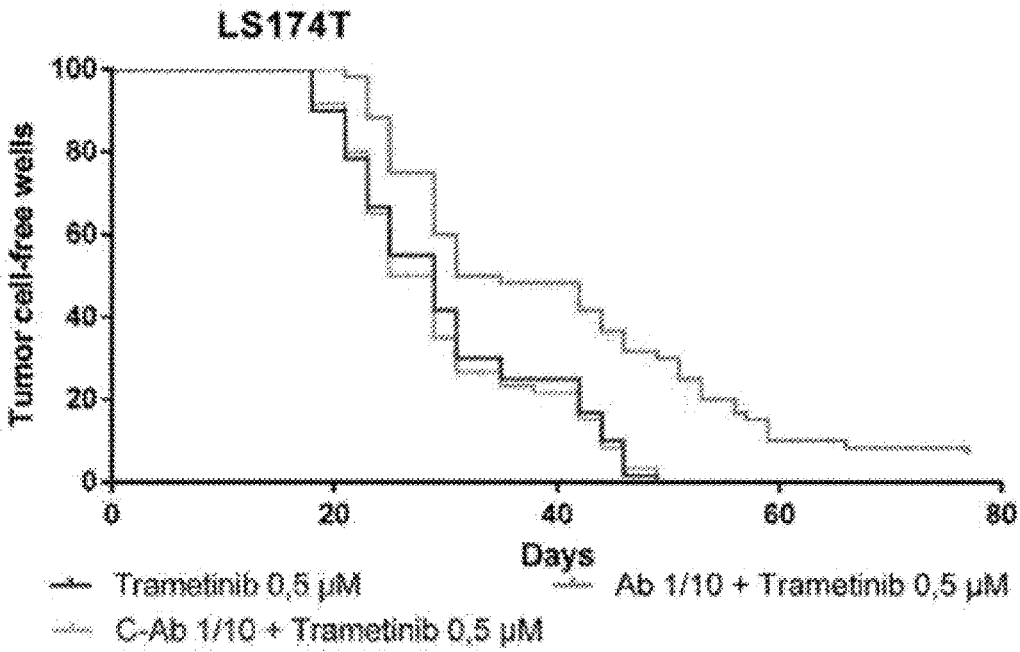
FIG. 11 shows the development of resistance to Trametinib by LS174T cell with the anti-IN01 therapeutic antibody, or a control antibody, C-Ab, used in combination with 0.5 μM Trametinib.
Figure 12:
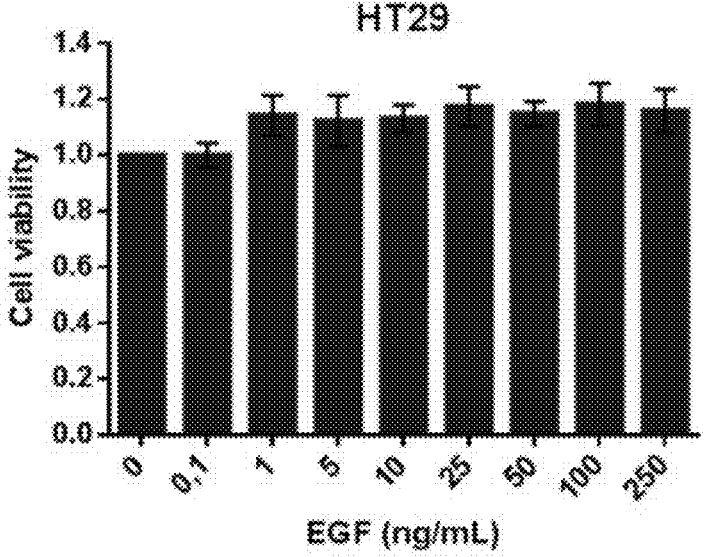
FIG. 12 shows the increase in cell growth of HT29, carrying a BRAF V66E mutation, in the presence of EGF.
Figure 13A:
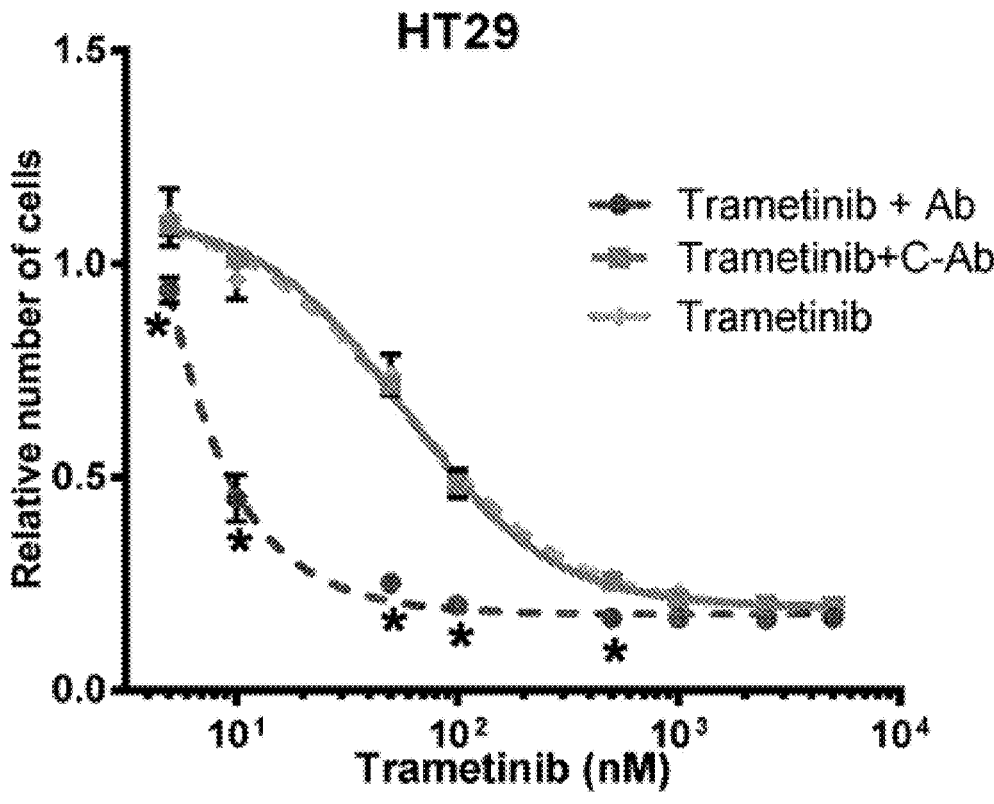
FIGS. 13A-C show the effect of the anti-IN01 Ab in combination with Trametinib on HT29 cell signaling and long term viability.
Figure 13B:
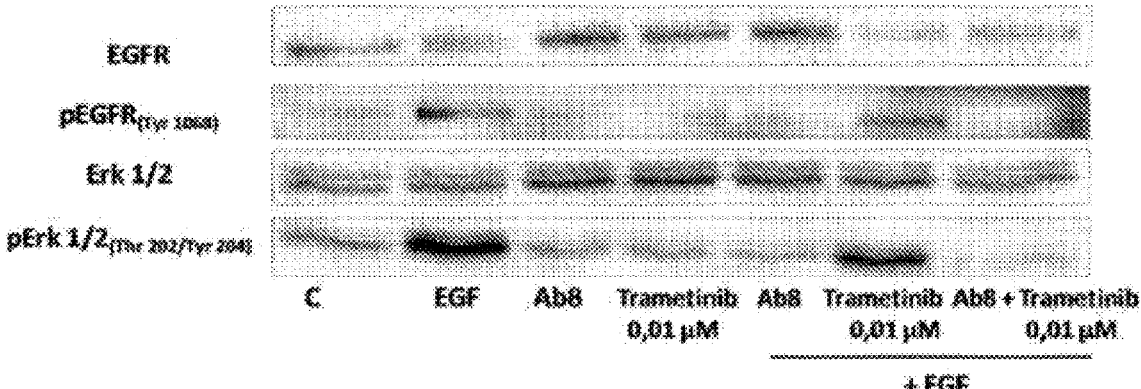
Figure 13C:
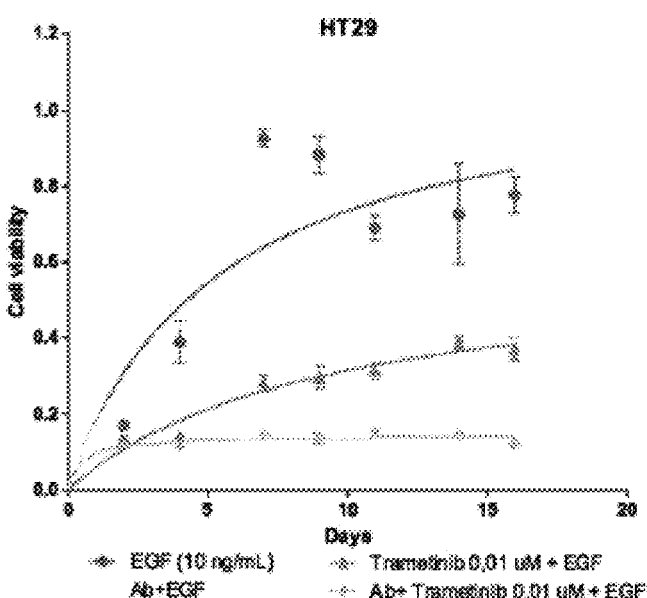
Figure 53:
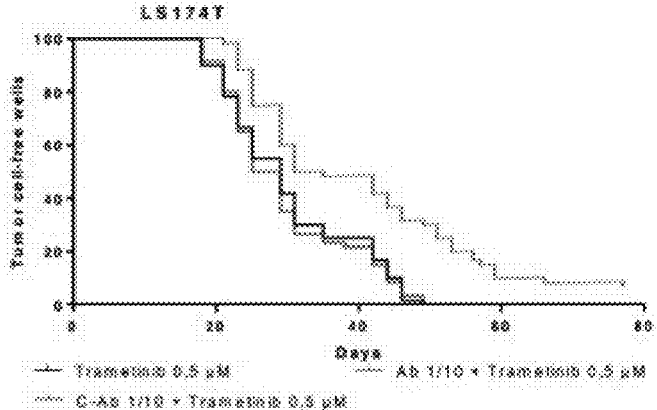
FIG. 53 shows the emergence of resistance over time to Trametinib in LS174T cells. 0.5 mM Trametinib was administered alone or in combination with the anti-IN01 antibody, "Ab" or control antibody, "C-Ab."
Figure 54:
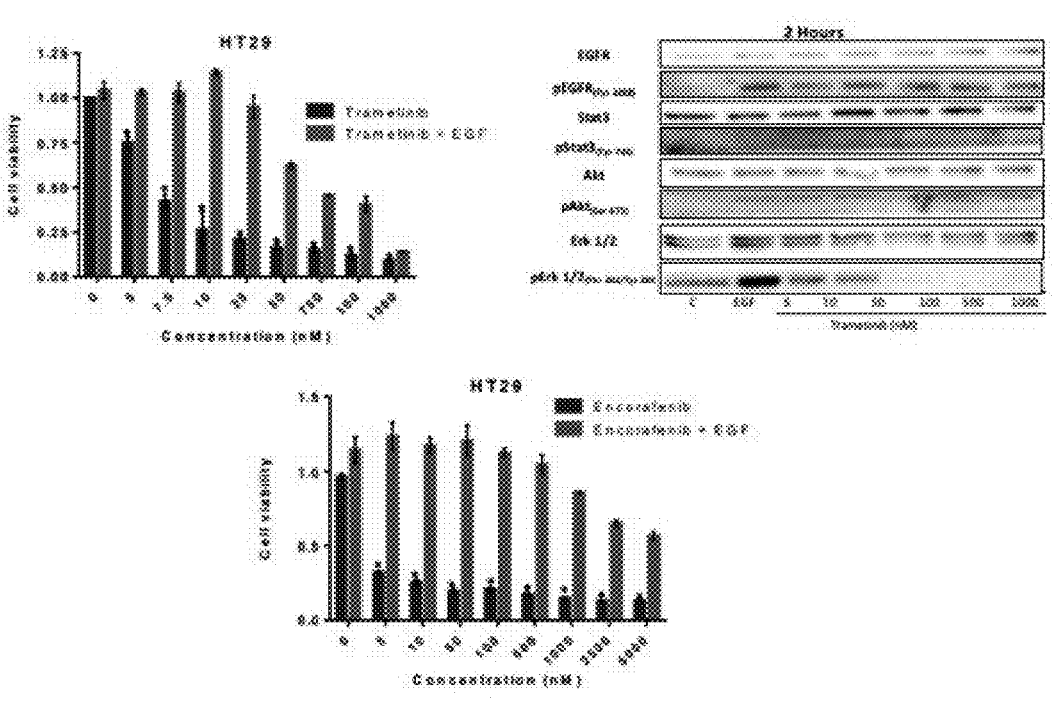
FIG. 54 shows the effects of kinase inhibitors with and without EGF in HT29 cells. Top, left, shows the effects of a 3 day incubation with different concentrations of Trametinib, with and without EGF, on HT29 cell viability. Top, right, shows the effects on pEGFR, pStat3, pAkt, and pErk ½ signaling, assessed by western blot, of a 2 hour incubation with EGF or different concentrations of Trametinib.
Figure 55:
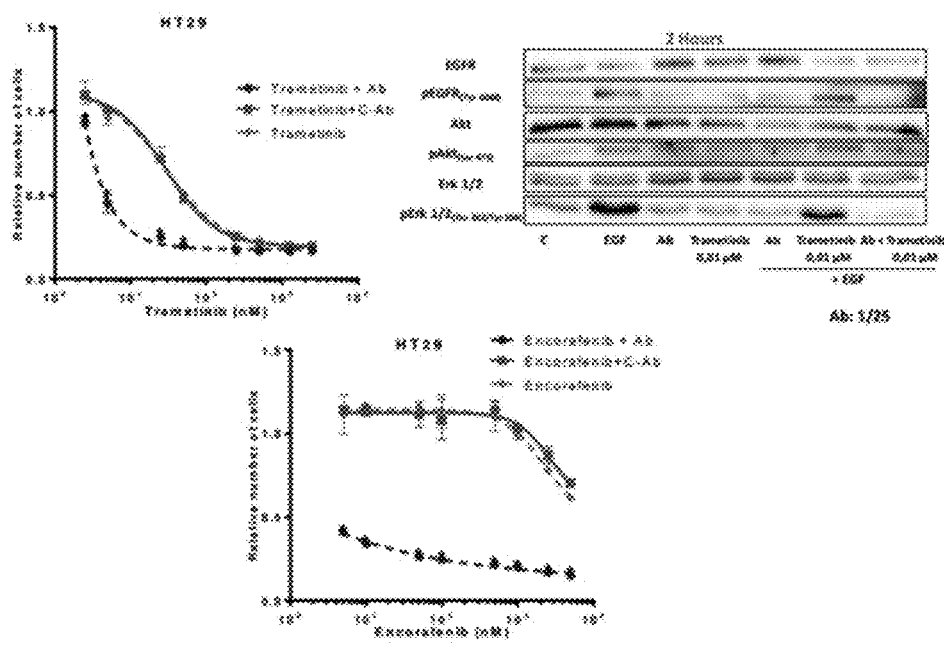
FIG. 55 shows the effects of antibody and kinase inhibitor combination therapy in HT29 cells, in the presence of EGF. Top, left shows the effect of a 3 day incubation with different concentrations of Trametinib, either alone or in combination with the anti-IN01 antibody "Ab," or the control antibody "C-Ab," on HT29 cell viability. Top, right shows the effects of on pEGFR, pAkt, and pErk ½ signaling, assessed by western blot, of a 2 hour incubation with EGF, the anti-IN01 antibody, "Ab," or Trametinib, alone or in combination.
Figure 56:
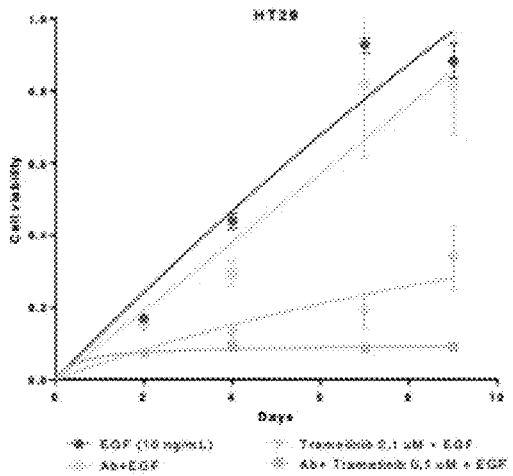
FIG. 56 shows the effects of long term incubation of Encorafenib, EGF, and the anti-IN01 antibody "Ab," either alone or in combination on HT29 cell viability.
Figure 57:
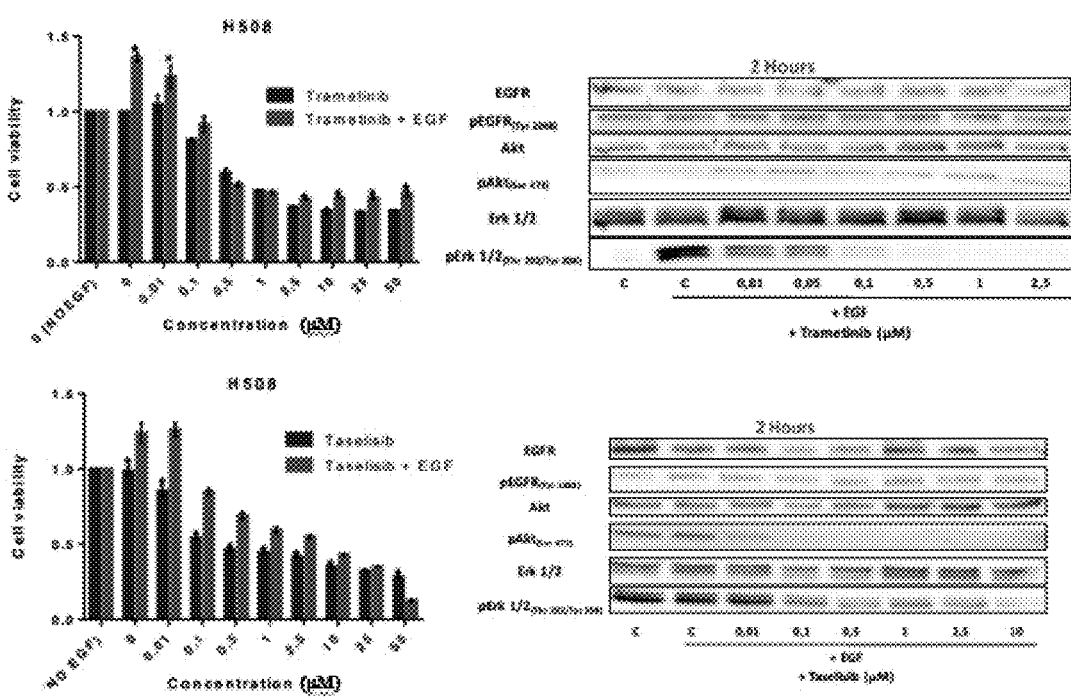
FIG. 57 shows the effects of Trametinib and Taselisib with and without EGF in H508 cells. Top right, shows the effects of a 3 day incubation of different concentrations of Trametinib, with and without EGF on H508 cell viability. Top, left, shows the effects on pEGFR, pAkt, and pErk ½ signaling, assessed by western blot, of a 2 hour incubation with EGF and different concentrations of Trametinib. Bottom, left, shows the effects of a 3 day incubation with Taselisib, in the presence and absence of EGF, on H508 cell viability. Bottom, right, shows the effects on pEGFR, pAkt, and pErk ½ signaling, assessed by western blot, of a 2 hour incubation with EGF and different concentrations of Taselisib.
Figure 58:
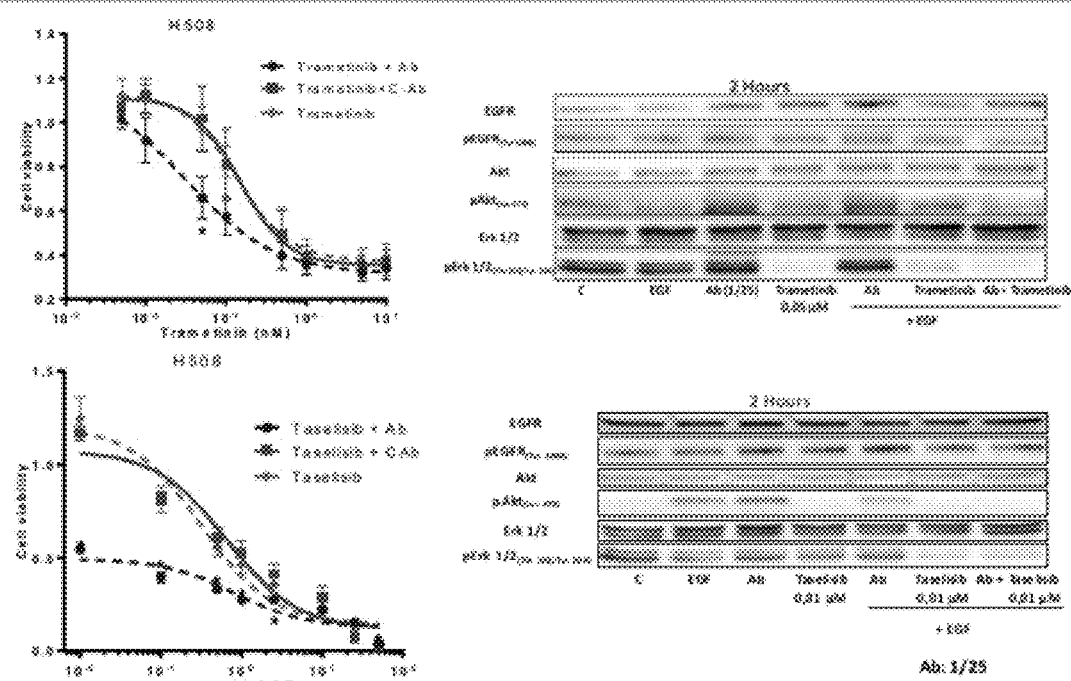
FIG. 58 shows the shows the effects of antibody and kinase inhibitor combination therapy in H508 cells, in the presence of EGF. Top, right, shows the effects of a 3 day incubation with different concentrations of Trametinib, either alone or in combination with the anti-IN01 antibody "Ab," or the control antibody "C-Ab," on H508 cell viability. Top, right, shows the effects of on pEGFR, pAkt, and pErk ½ signaling, assessed by western blot, of a 2 hour incubation with EGF, the anti-IN01 antibody, "Ab," and Trametinib, either alone or in combination. Bottom, right, shows the effects of a 3 day incubation with different concentrations of Taselisib, either alone or in combination with the anti-IN01 antibody "Ab," or the control antibody "C-Ab," on H508 cell viability. Bottom, right, shows the effects of on pEGFR, pAkt, and pErk ½ signaling, assessed by western blot, of a 2 hour incubation with EGF, the anti-IN01 antibody, "Ab," and Taselisib, either alone or in combination.
Figure 59:
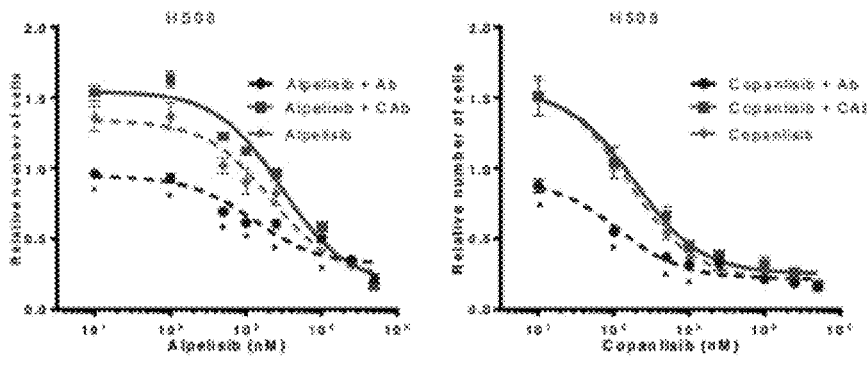
FIG. 59 shows the effects of antibody and Alpelisib and Copanlisib kinase inhibitors combination therapy in H508 cells, in the presence of EGF. Left, shows the effects of a 3 day incubation with different concentrations of Alpelisib, either alone or in combination with the anti-IN01 antibody "Ab," or the control antibody "C-Ab," on H508 cell viability. Right, shows the effects of a 3 day incubation with different concentrations of Copanlisib, either alone or in combination with the anti-IN01 antibody "Ab," or the control antibody "C-Ab," on H508 cell viability.
Figure 60:
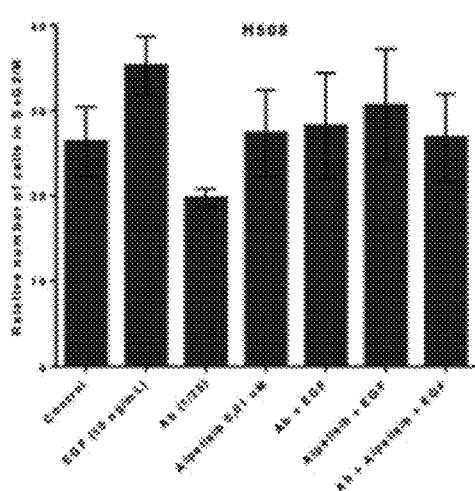
FIG. 60 shows the relative number of H508 cells in S and G2/M phases of the cell cycle in response to the anti-IN01 antibody, referred to as "Ab," EGF, and kinase inhibitors, in combination and alone. Left, shows the relative number of H508 cells in S and G2/M phases of the cell cycle in response to the anti-IN01 antibody, referred to as "Ab," EGF, and Alpelisisb, in combination and alone. Right, shows the relative number of H508 cells in S and G2/M phases of the cell cycle in response to the anti-IN01 antibody, referred to as "Ab," EGF, and Copanlisib, in combination and alone.
Figure 60:
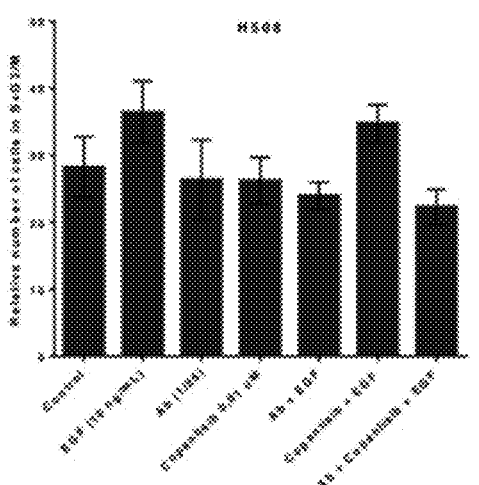
Figure 61:
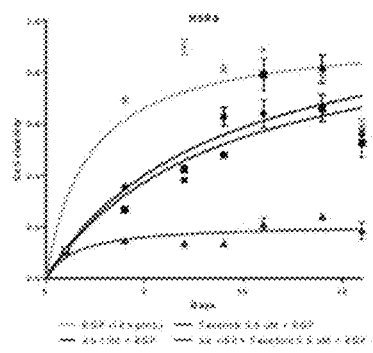
FIG. 61 shows the longer term effects of kinase inhibitors and EGF, alone, and in combination with the anti-IN01 antibody, "Ab" on H508 cell viability. Left, shows the effects of 0.5 mM Taselisib and EGF, alone and in combination with the anti-IN01 antibody, "Ab" on H508 cell viability. Right, shows the effects of 0.1 mM Copanlisib and EGF, alone and in combination with the anti-IN01 antibody, "Ab" on H508 cell viability.
Figure 61:
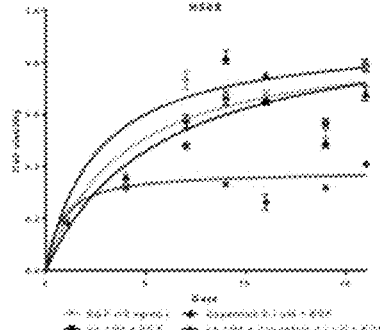

FIGS. 7-11 show the effects of the anti-IN01 antibody in combination with Trametinib I n LS174T cells. Compared to the effects on cell viability in DLD1 cells, the combinatorial therapy is less pronounced in the LS174T cells. However, the activation of pAkt, pEGFR, and pErk½ are almost completely inhibited in LS174T cells (FIG. 10). Notably, as shown in FIG. 53, Trametinib resistance is significantly delayed when the anti-IN01 antibody is co-administered in LS174T cell lines.

Notably, the anti-IN01 antibody consistently reverses the stimulatory effect of EGF on these KRAS mutant cell lines. As shown EGF stimulates KRAS cell line growth, while the anti-IN01 antibody, in combination with Trametinib or Taselisib, inhibits EGF induced cell growth and delays resistance to the non-tyrosine targeting kinase inhibitors.

Example 2: A549 (G12S KRAS) and HCC15 (Q61K NRAS) Ras Mutant Cell Lines Response to Anti-IN01 Antibody NTKI Combination Therapies The anti-IN01 (BVN22E) antibody was developed from SEQ ID NO: 2, which consists of two repeated synthetic EGF Targeted Signaling Pathway (SEQ ID NO: 7) domains, Glycine-Serine repeat linkers, and a CTB sequence (SEQ ID NO: 25). The anti-IN01 antibody was developed to be used in combination with non-tyrosine targeting kinase inhibitors targeting EGFR downstream effectors in order to inhibit cancer cell growth. In this example, the A549 cell line, which carries a KRAS G12S mutation, and the HCC15 cell line, which carries a Q61K mutation in NRAS were used.

Figure 31:
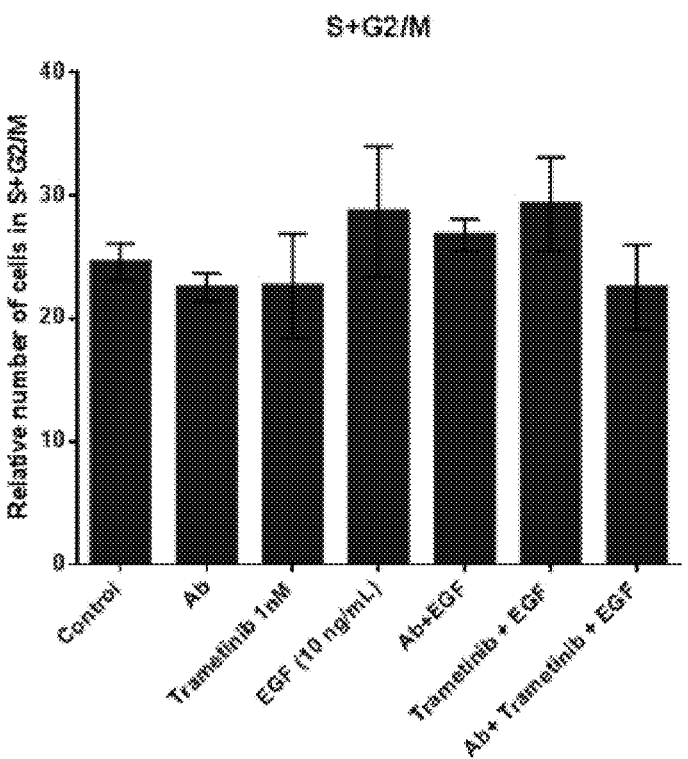
FIG. 31 shows the relative number of A549 cells in S and G2/M phases of the cell cycle in response to the anti-IN01 antibody, referred to as "Ab," EGF, and 1 nM Trametinib, in combination and alone.
Figure 32:
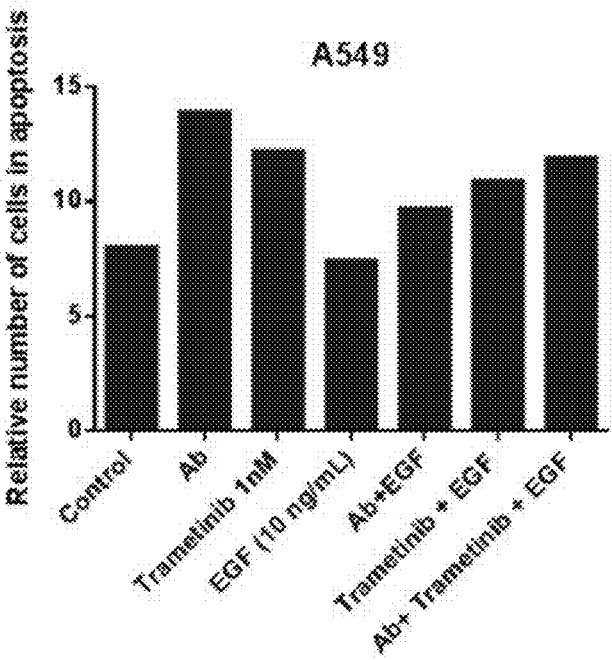
FIG. 32 shows the relative number of A549 cells in apoptosis in response to the anti-IN01 antibody, referred to as "Ab," EGF, and 1 nM Trametinib, in combination and alone.
Figure 33:
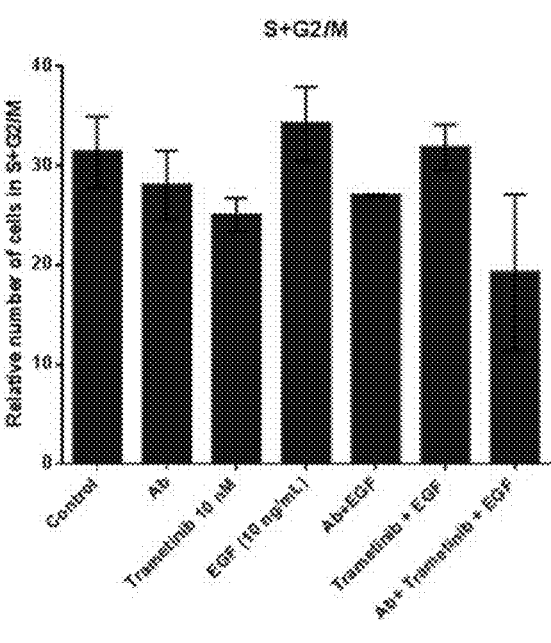
FIG. 33 shows the relative number of DLD1 cells in S and G2/M phases of the cell cycle in response to the anti-IN01 antibody, referred to as "Ab," EGF, and 10 nM Trametinib, in combination and alone.
Figure 34:
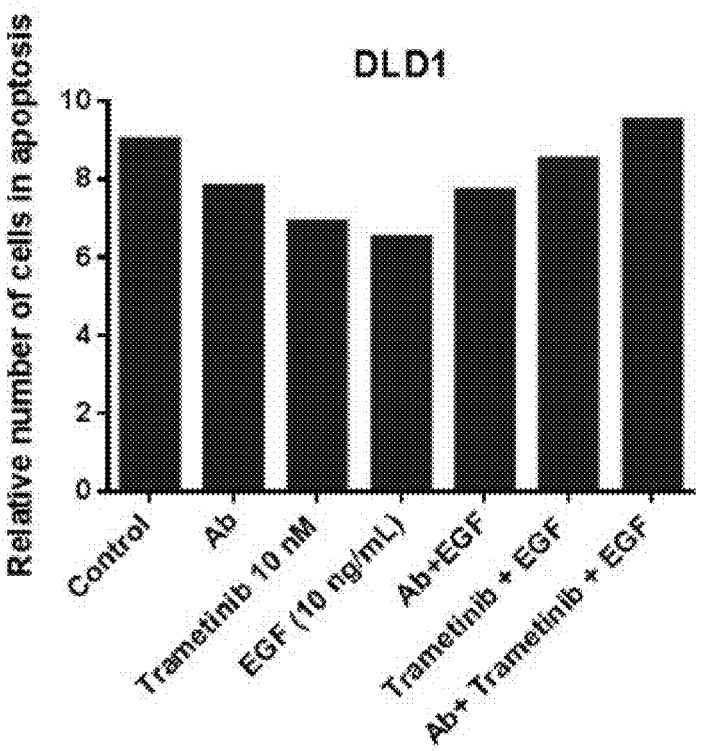
FIG. 34 shows the relative number of DLD1 cells in apoptosis in response to the anti-IN01 antibody, referred to as "Ab," EGF, and 10 nM Trametinib, in combination and alone.

FIGS. 31 and 32 show that the number of A549 cells in S and G2/M phases was lower with anti-IN01 and Trametinib combination therapy, and the number of A549 cells in apoptosis was higher, as assessed by flow cytometry. FIGS. 66, 68, 72, and 73 show the effects of Trametinib alone, and in combination with anti-IN01 antibodies in HCC15 cells, wherein anti-IN01 antibodies enhance the effect of Trametinib in lowering cell viability.

Figures 62, 63:
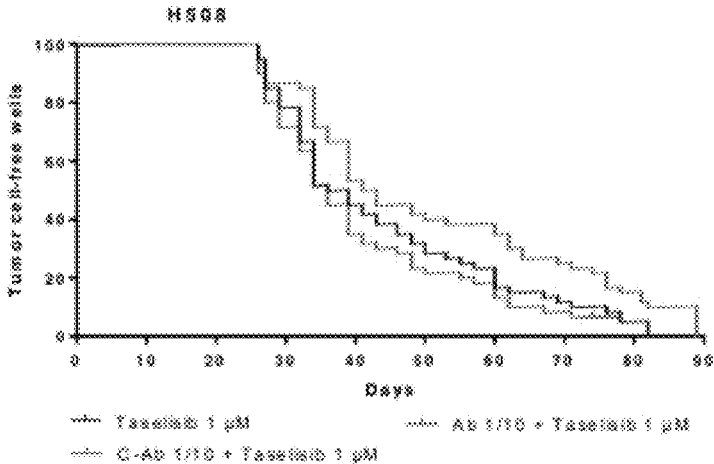
FIG. 62 shows the emergence of resistance to Taselisib in H508 cells. Taselisib was administered alone or in combination with either the anti-IN01 antibody "Ab," or the control antibody "C-Ab" and H508 cell growth was monitored over time.
FIG. 63 shows exemplary cell lines, relevant alterations, and kinase inhibitors used in the instant application.
Figure 64:
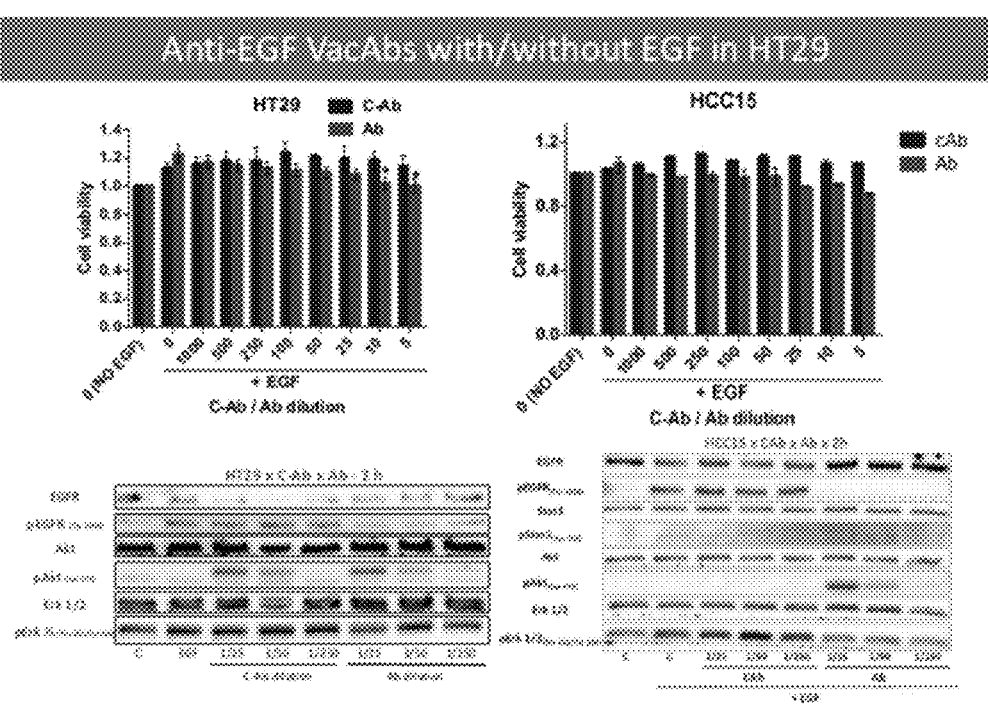
FIG. 64 shows the effects of the anti-IN01 antibody without and EGF on HT29 and HCC15 cells. Top, left, shows the effects of 3 day incubation with different dilutions of the anti-IN01 antibody, "Ab," and the control antibody, "C-Ab," on HT29 cell viability in the presence of EGF. Top, right, shows the effects of 3 day incubation with different dilutions of the anti-IN01 antibody, "Ab," and the control antibody, "C-Ab," on HCC15 cell viability in the presence of EGF. Bottom, left, shows the effects on pEGFR, pAkt, and pErk ½ signaling, assessed by western blot, of a 2 hour incubation with EGF, different concentrations of the anti-IN01 antibody, "Ab," or a control antibody, "C-Ab," in HT29 cells. Bottom, right, shows the effects of pEGFR, pStat3, pAkt, and pErk ½ signaling, assessed by western blot, of a 2 hour incubation with EGF, different concentrations of the anti-IN01 antibody, "Ab," or a control antibody, "C-Ab" in HCC15 cells.
Figure 65:
FIG. 65 shows the effects of Trametinib and Encorafenib with and without EGF in HT29 cells. Top, left, shows the effects of 3 day incubation with different concentrations of Trametinib, with and without EGF, on HT29 cell viability. Top, right, shows the effects of 2 hour incubation of EGF and different concentrations of Tramentinib on pEGFR, pStat3, pAkt, and pErk ½ signaling, assessed by western blot in HT29 cells. Bottom, left, shows the effects of different concentrations of Encorafenib, in the presence and absence of EGF on HT29 cell viability. Bottom, right, shows the effects of 2 hour incubation of EGF and different concentrations of Encorafenib on pEGFR, pAkt, and pErk ½ signaling, assessed by western blot in HT29 cells
Figure 65:
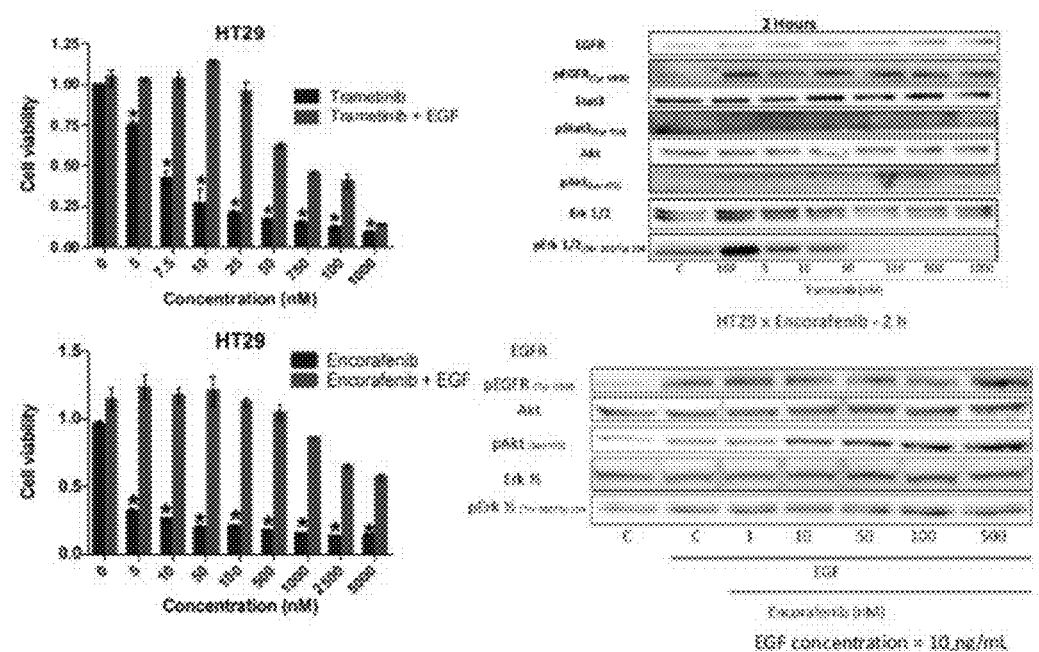
Figure 66:
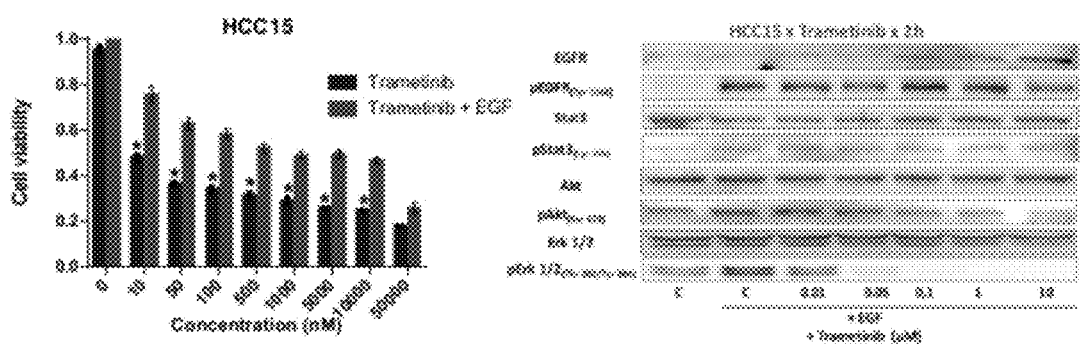
FIG. 66 shows the effects of Trametinib with and without EGF in HCC15 cells. Left, shows the effects of 3 day incubation with different concentrations of Trametinib, in the presence and absence of EGF, on HCC15 cell viability. Right, shows the effects on pEGFR, pStat3, pAkt, and pErk½ signaling of 2 hour incubation with EGF and different concentrations of Trametinib.
Figure 67:
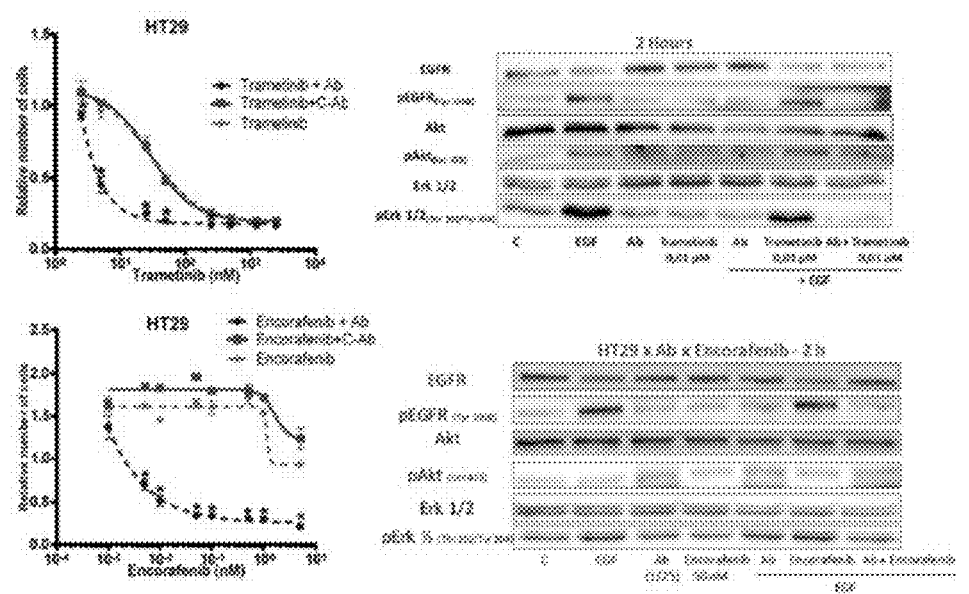
FIG. 67 shows the effects of kinase inhibitors in combination with the anti-IN01 antibody on HT29 cells, in the presence of EGF. Top, left, shows the effects of a 3 day incubation with different concentrations of Trametinib, alone or in combination with the anti-IN01 antibody, "Ab," or a control antibody, "C-Ab," on HT29 cell viability. Top, right, shows the effects on pEGFR, pAkt, and pErk½ signaling of 2 hour incubation with EGF, the anti-IN01 antibody, "Ab, and Trametinib, alone or in combination in HT29 cells. Bottom, left, shows the effects of 3 day incubation with different concentrations of Encorafenib, alone or in combination with the anti-IN01 antibody, "Ab," or a control antibody, "C-Ab" in HT29 cells. Bottom, right, shows the effects on pEGFR, pAkt, and pErk½ signaling of 2 hour incubation with EGF, the anti-IN01 antibody, "Ab," and Encorafenib, alone or in combination in HT29 cells.
Figure 68:
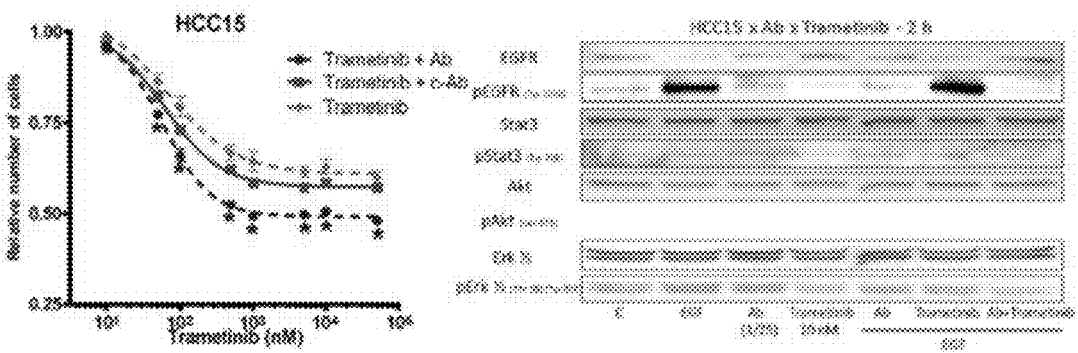
FIG. 68 shows the effects of Trametinib in combination with the anti-IN01 antibody on HCC15 cells, in the presence of EGF. Left, shows the effects of a 3 day incubation with different concentrations of Trametinib, alone or in combination with the anti-IN01 antibody, "Ab," or a control antibody, "C-Ab," on HCC15 cell viability. Right, shows the effects on pEGFR, pStat3, pAkt, and pErk½ signaling of 2 hour incubation with EGF, the anti-IN01 antibody, "Ab, and Trametinib, alone or in combination in HCC15 cells.
Figure 69:
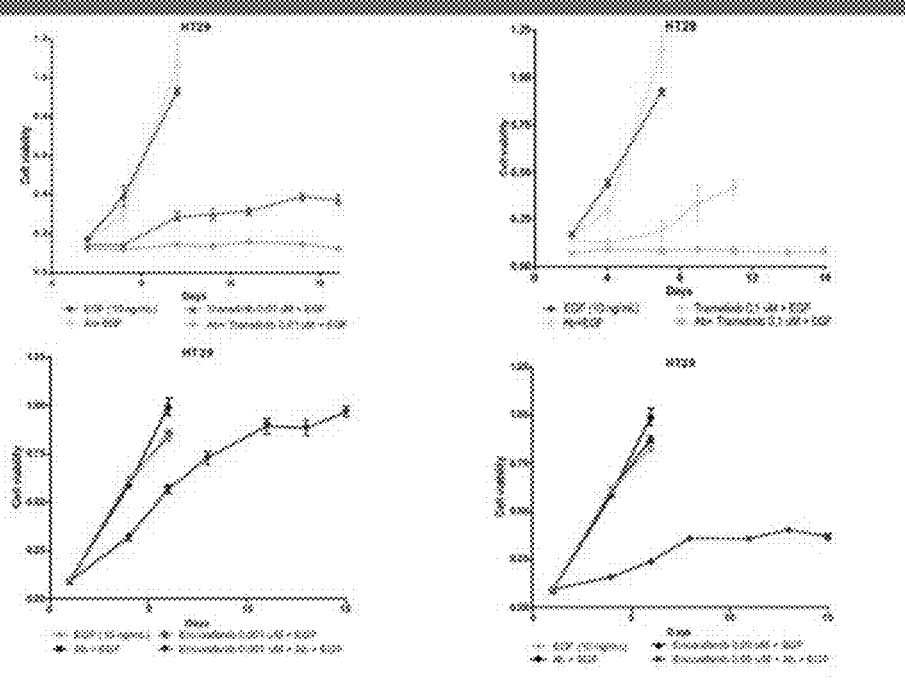
FIG. 69 shows the long term effects of kinase inhibitors and the anti-IN01 antibody in the presence of 10 ng/mL EGF on HT29 cell viability. Top, left, shows the long term effects of EGF, the anti-IN01 antibody, "Ab," alone or in combination with 0.01 mM Trametinib, on HT29 cell viability.

Example 3: HT29 (V600E BRAF) and H508 (G596R BRAF and E545K PIK3CA) Mutant Cell Lines Response to Anti-IN01 Antibody NTKI Combination Therapies The anti-IN01 (BVN22E) antibody was developed from SEQ ID NO: 2, which consists of two repeated synthetic EGF Targeted Signaling Pathway (SEQ ID NO: 7) domains, Glycine-Serine repeat linkers, and a CTB sequence (SEQ ID NO: 25). The anti-IN01 antibody was developed to be used in combination with non-tyrosine targeting kinase inhibitors targeting EGFR downstream effectors in order to inhibit cancer cell growth. In this example, HT29 and H508 cells which carry BRAF and PIK3CA mutations were used (FIGS. 43, 63, and 74).

Figure 14:
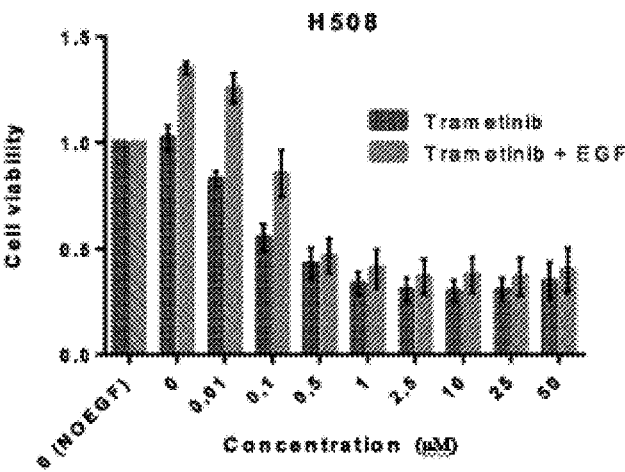
FIG. 14 shows the effect of a 3 day incubation of different concentrations of Trametinib on H508 cell viability, with and without EGF.
Figure 15:
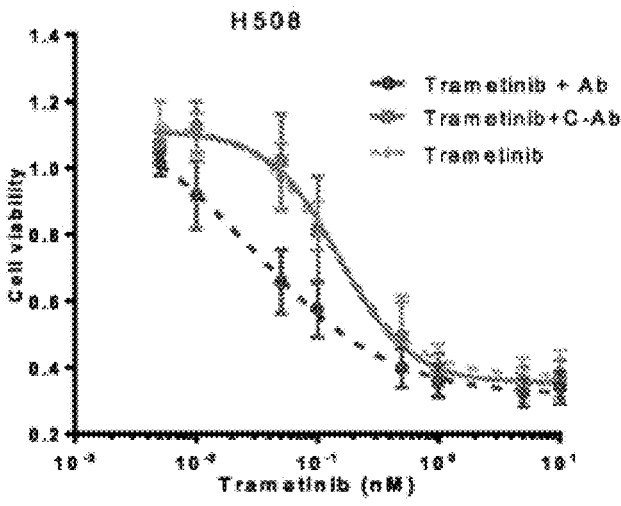
FIG. 15 shows the effect of a 3 day incubation with the anti-IN01 therapeutic antibody, "Ab," or a control antibody, "C-Ab," used in combination with different concentrations of Trametinib on H508 cell viability.
Figure 16:
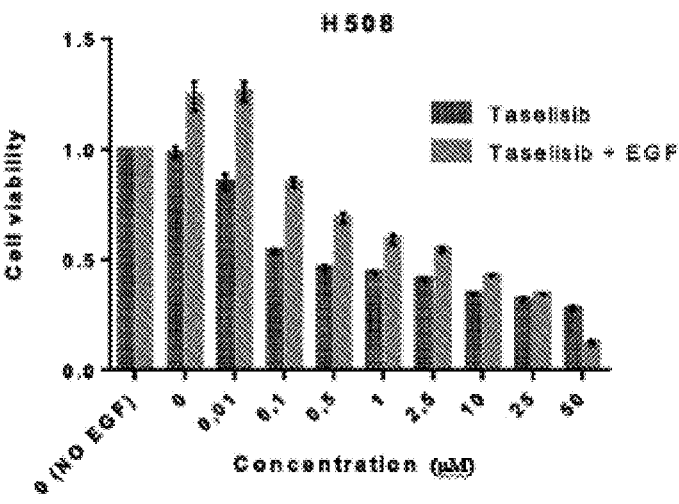
FIG. 16 shows the effect of a 3 day incubation of different concentrations of Taselisib on H508 cell viability, with and without EGF.
Figure 17:
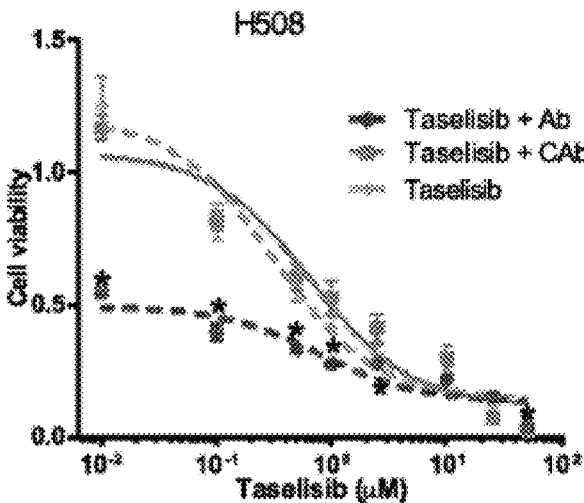
FIG. 17 shows the effect of a 3 day incubation with the anti-IN01 therapeutic antibody, "Ab," or a control antibody, "C-Ab," in combination with different concentrations of Taselisib on H508 cell viability.
Figure 18:
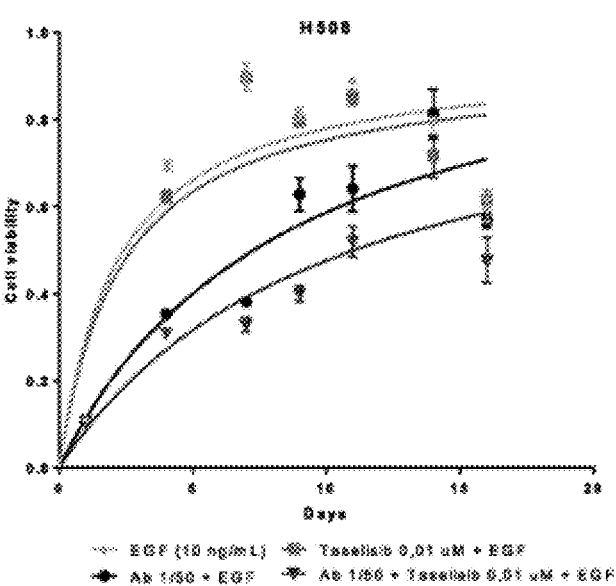
FIG. 18 shows the longer term effects on H508 cell viability of the anti-IN01 therapeutic antibody, at a 1/50 dilution, in combination with EGF and 0.1 mM Taselisib.
Figure 19:
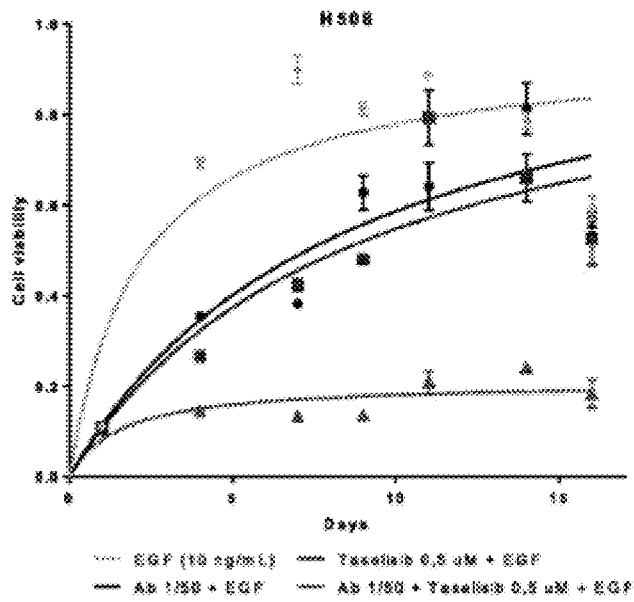
FIG. 19 shows the longer term effects on H508 cell viability of the anti-IN01 therapeutic antibody, at a 1/50 dilution, in combination with EGF and 0.5 mM Taselisib.

FIGS. 12, 13, and 54-56 show the decreased cell viability of HT29 cells with Trametinib of Encorafenib when used in combination with the anti-IN01 antibody. FIGS. 14-22, 57-62, 72, 73, and 75-77 show the decreased cell viability of H508 and HT29 cells with Trametinib, Taselisib, Alpelisib, and Copanlisib with the anti-IN01 antibody. FIGS. 18 and 19 notably demonstrate that effective inhibition of cell viability by Taselsib in combination with the anti-IN01 antibody was achieved at concentrations below that of current patient therapies. FIG. 14 also shows that the anti-IN01 antibody in combination with Trametinib strongly enhanced the inhibition of pEGFR and pErk½ activation over Trametinib alone in HT29 cells.

Figure 20:
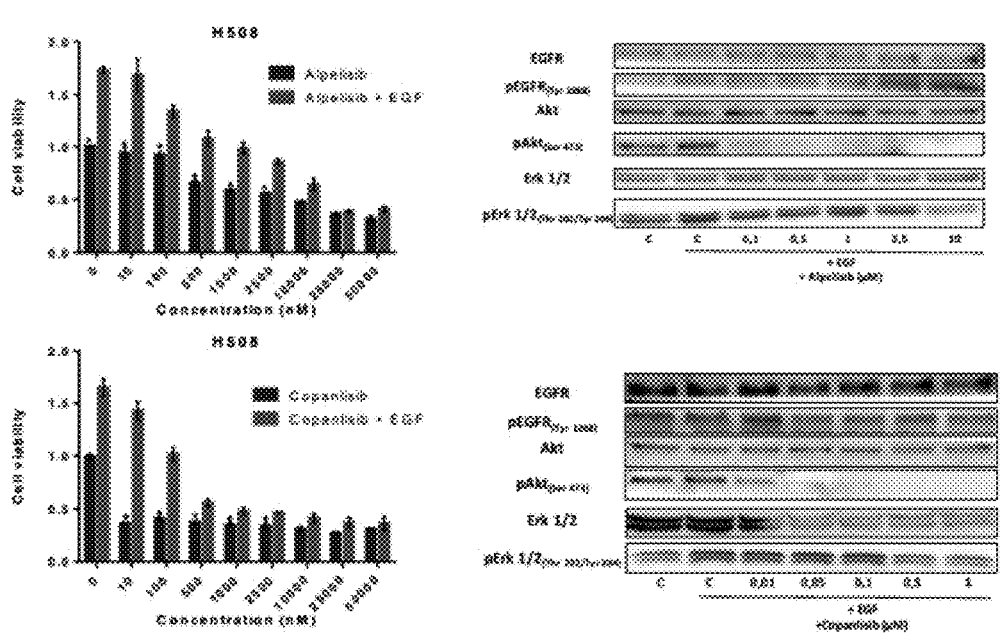
FIG. 20 shows the effects of Alpelisib and Copanlisib with and without EGF in H508 cells. Top, left, shows the effect of 3 day incubation of different concentrations of Alpelisib on H508 cell viability with and without EGF. Top, right, shows the effect on pEGFR, pAkt, and pErk ½ signaling, assessed by western blot, of a 2 hour incubation with EGF and different concentrations of Alpelisib. Bottom, left, shows the effect of 3 day incubation with different concentrations of Copanlisib on H508 cell viability, with and without EGF. Bottom, right, shows the effect on pEGFR, pAkt, and pErk ½ signaling, assessed by western blot, of a 2 hour incubation with EGF and different concentrations of Copanlisib.
Figure 21:
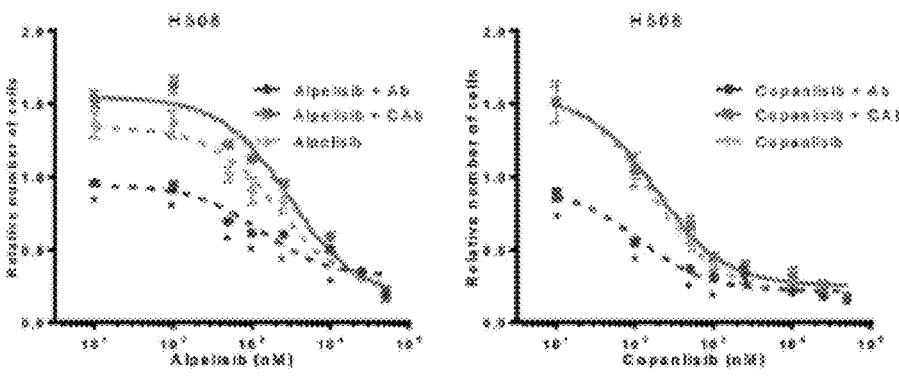
FIG. 21 shows the effects of Alpelisib and Copanlisib, in combination with the anti-IN01 antibody, on H508 cell viability, in the presence of EGF.
Figure 22:
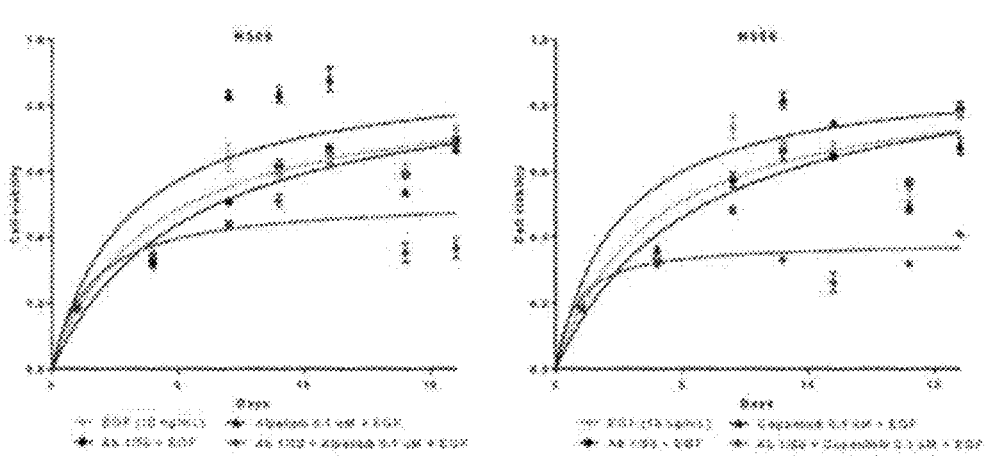
FIG. 22 shows the longer term effects on H508 cell viability of the anti-IN01 therapeutic antibody in combination with EGF and Alpelisib (left) and Copanlisib (right).
Figure 23:
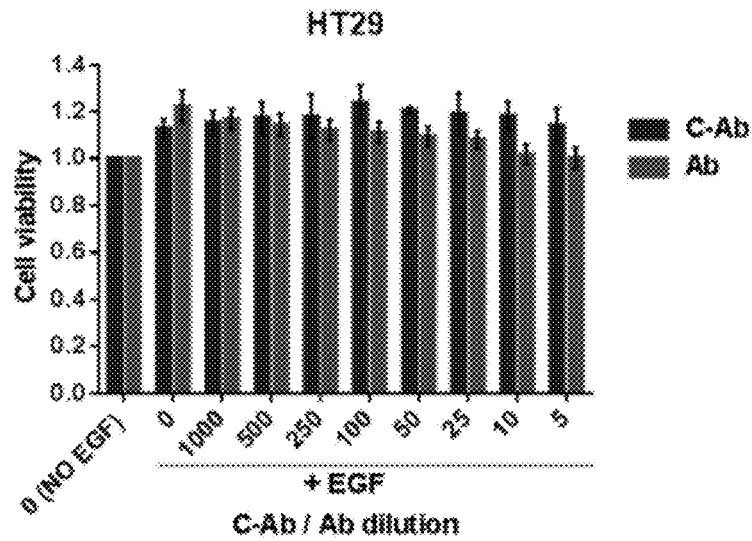
FIG. 23 shows the effects of the anti-IN01 therapeutic antibody, "Ab," or the control antibody, "C-Ab," in combination with EGF, on HT29 cell viability.
Figure 24:
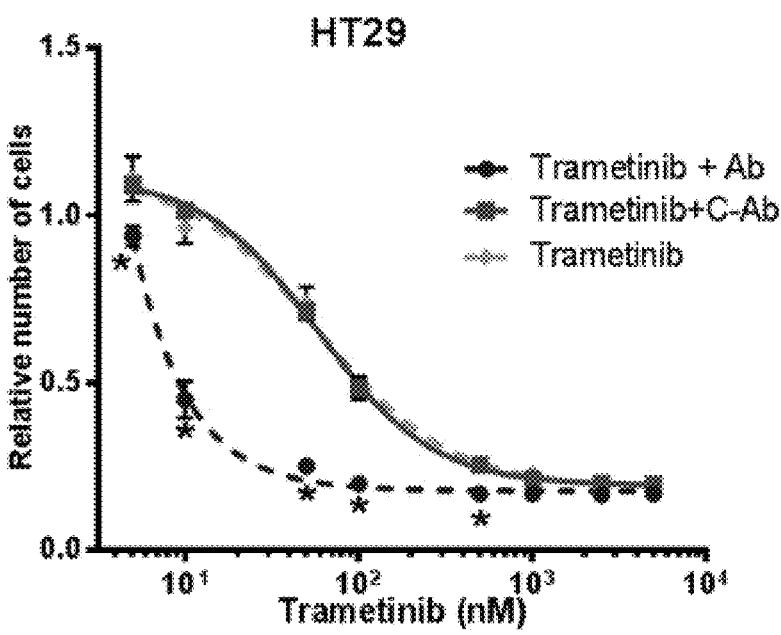
FIG. 24 shows the effects of a 3 day incubation with the anti-IN01 therapeutic antibody, or a control antibody, C-Ab, used in combination with different concentrations of Trametinib on HT29 cell viability.
Figure 25:
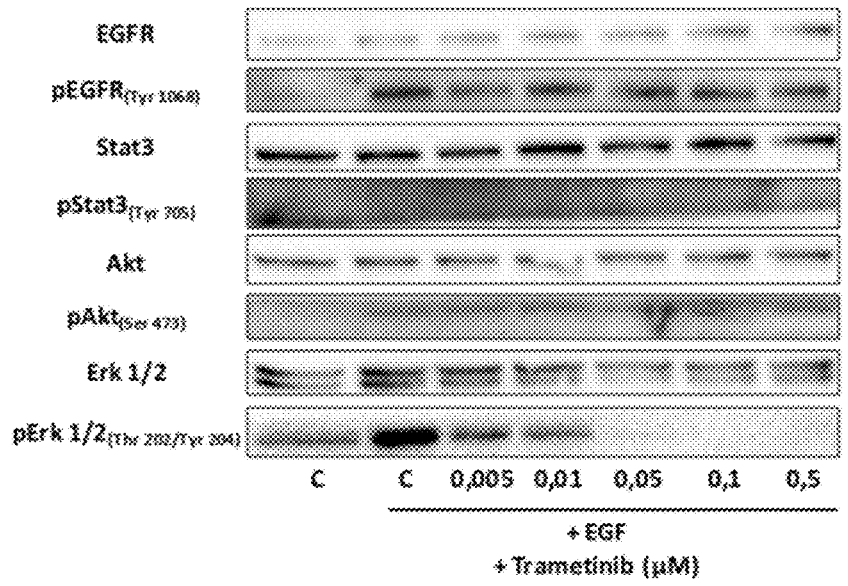
FIG. 25 shows the effects on pEGFR, pStat3, pAkt, and pErk½ signaling, assessed by western blot, of a 2 hour incubation with EGF and different concentrations of Trametinib in HT29 cells.
Figure 26:
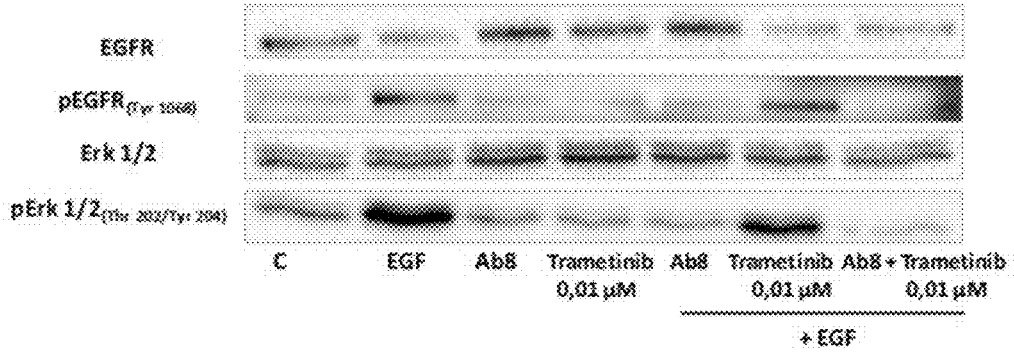
FIG. 26 shows the effects on pEGFR and pErk½ signaling of a 2 hour incubation with EGF, 0.01 mM Trametinib, and the anti-IN01 antibody, referred to as "Ab8", alone or in combination, in HT29 cells.

FIG. 20 shows that Alpelisib and Copanlisib, which are PIK3CA inhibitors, inhibit pAkt, but do not affect pEGFR or pErk½ signaling. However, FIG. 21 shows that these inhibitors exhibit effects on cell viability in combination with the anti-IN01 antibody similar to that of Taselisib. Similarly, the anti-IN01 antibody had a greater effect on H508 cell viability than Alpelisib or Copanlisib alone at low concentrations (FIG. 22). These results indicate that Taselisib provides more targeted and likely more effective tumor growth inhibition.

Taselisib targets PIK3CA, Encorafenib targets BRAF, while Trametinib is a MEK inhibitor. The similar effects of PIK3CA, BRAF, and KRAS inhibitors in achieving decreased cell proliferation and EGFR effector signaling, particularly in combination with the anti-IN01 antibody, indicate that targeting multiple pathways downstream of EGFR demonstrates more therapeutic options and greater efficacy in treating cancer.

Example 4: PC9/PC9GR4 (Exon 19 Deletion in EGFR) Mutant Cell Lines Response to Anti-IN01 Antibody TKI Combination Therapies The anti-IN01 (BVN22E) antibody was developed from SEQ ID NO: 2, which consists of two repeated synthetic EGF Targeted Signaling Pathway (SEQ ID NO: 7) domains, Glycine-Serine repeat linkers, and a CTB sequence (SEQ ID NO: 25). The anti-IN01 antibody was developed to be used in combination with tyrosine targeting kinase inhibitors targeting EGFR in order to inhibit cancer cell growth. In this example, PC9/PC9GR cells were used.

Figure 27:
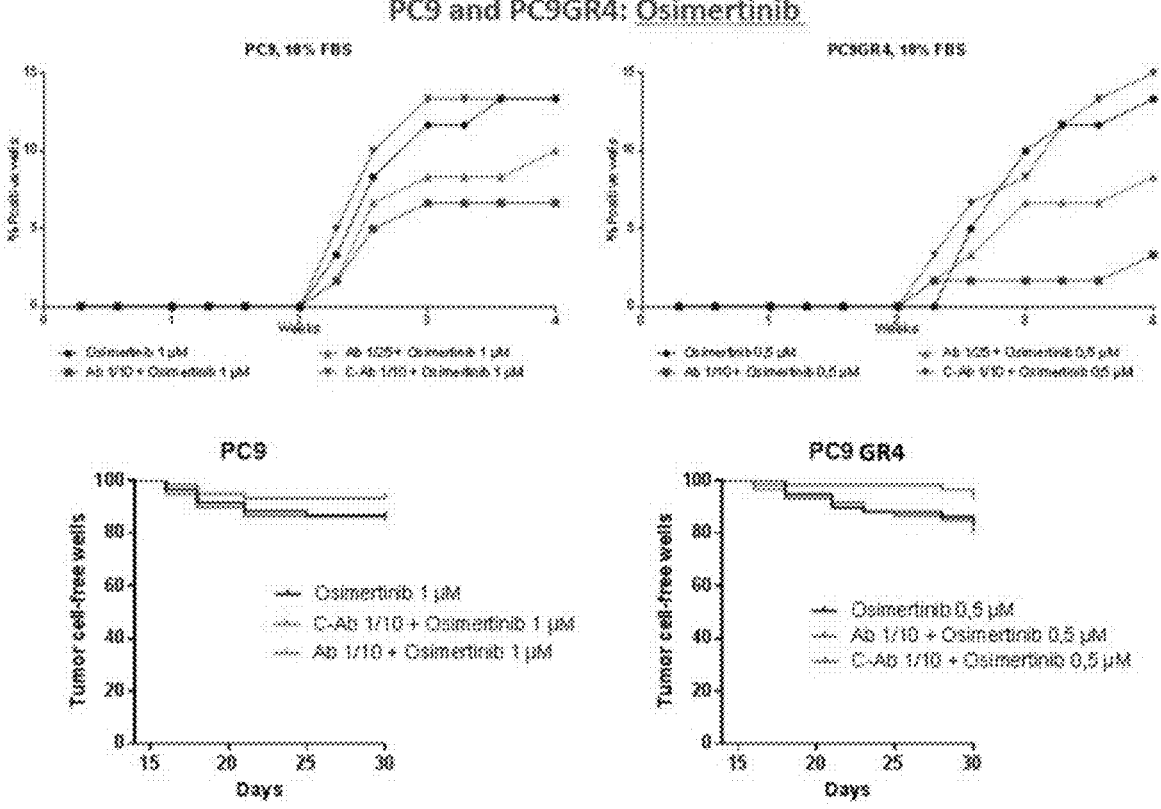
FIG. 27 shows the emergence of resistance over time in PC9 and PC9GR4 cells to kinase inhibitors. Top, left, shows the effects of the anti-IN01 antibody, referred to as "Ab," and the control antibody, referred to as "C-Ab," in combination with Osimertinib on PC9 cell viability. Top, right, shows the effects of the anti-IN01 antibody, referred to as "Ab," and the control antibody, referred to as "C-Ab," in combination with Osimertinib on PC9GR4 cell viability. Bottom, left, shows the effects of the anti-IN01 antibody, referred to as "Ab," and the control antibody, referred to as "C-Ab," in combination with Osimertinib on PC9 cell viability. Bottom, right, shows the effects of the anti-IN01 antibody, referred to as "Ab," and the control antibody, referred to as "C-Ab," in combination with Osimertinib on PC9GR4 cell viability, the effects of the anti-IN01 antibody, referred to as "Ab," and the control antibody, referred to as "C-Ab,"
Figure 28:
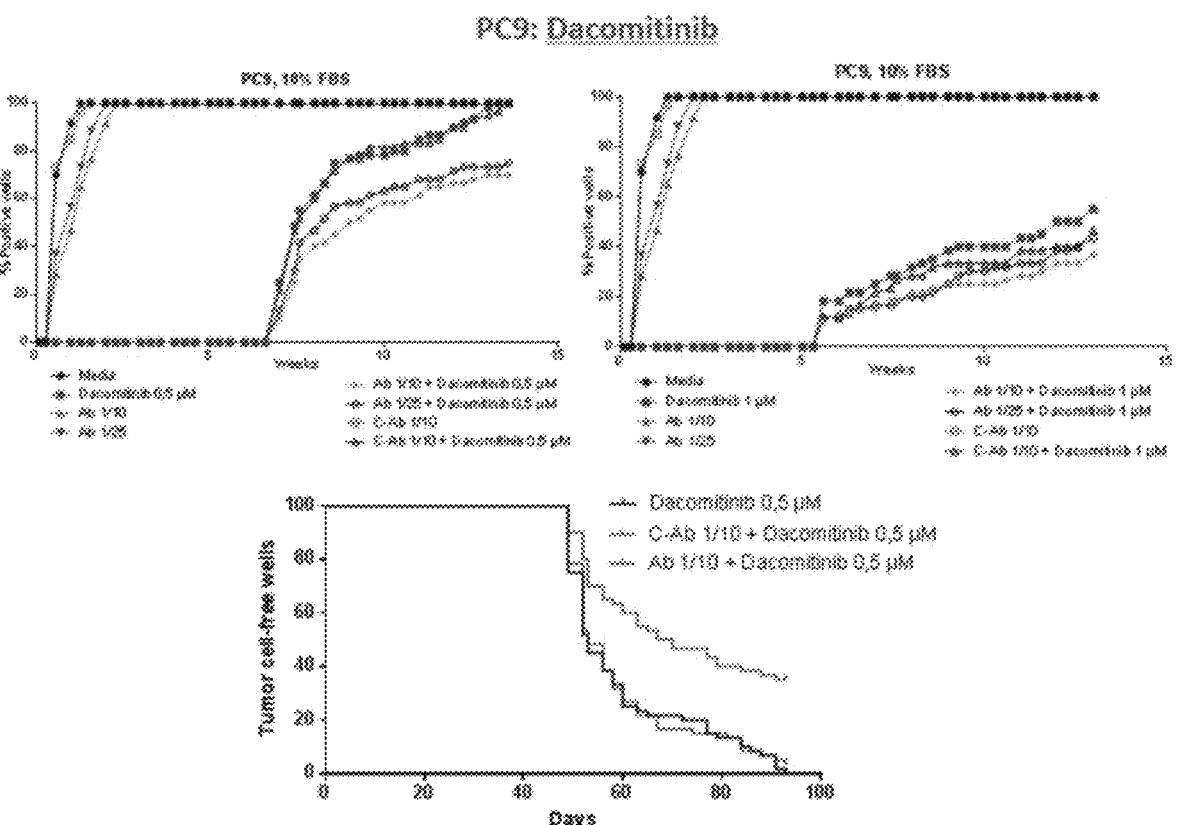
FIG. 28 shows the emergence of resistance over time of PC9 cells to kinase inhibitors. Top, left, shows the effects on PC9 cell viability of 10% FBS, the anti-IN01 antibody, referred to as "Ab," and the control antibody, referred to as "C-Ab," in combination with 0.5 mM Dacomitinib. Top, right, shows the effects on PC9 cell viability of 10% FBS, the anti-IN01 antibody, referred to as "Ab," and the control antibody, referred to as "C-Ab," in combination with 1.0 mM Dacomitinib.

FIGS. 27 and 28 show that emergence of resistance to Osimertinib and Dacomitnib was lowered when the anti-IN01 antibody was co-administered to the cells.

Example 5: H228 and H3122 EML4-ALK Translocation Mutant Cell Lines Response to Anti-IN01 Antibody TKI Combination Therapies The anti-IN01 (BVN22E) antibody was developed from SEQ ID NO: 2, which consists of two repeated synthetic EGF Targeted Signaling Pathway (SEQ ID NO: 7) domains, Glycine-Serine repeat linkers, and a CTB sequence (SEQ ID NO: 25). The anti-IN01 antibody was developed to be used in combination with tyrosine targeting kinase inhibitor Brigatinib targeting EGFR in order to inhibit cancer cell growth. In this example, the H228 and H3122 cells were used.

Figure 35:
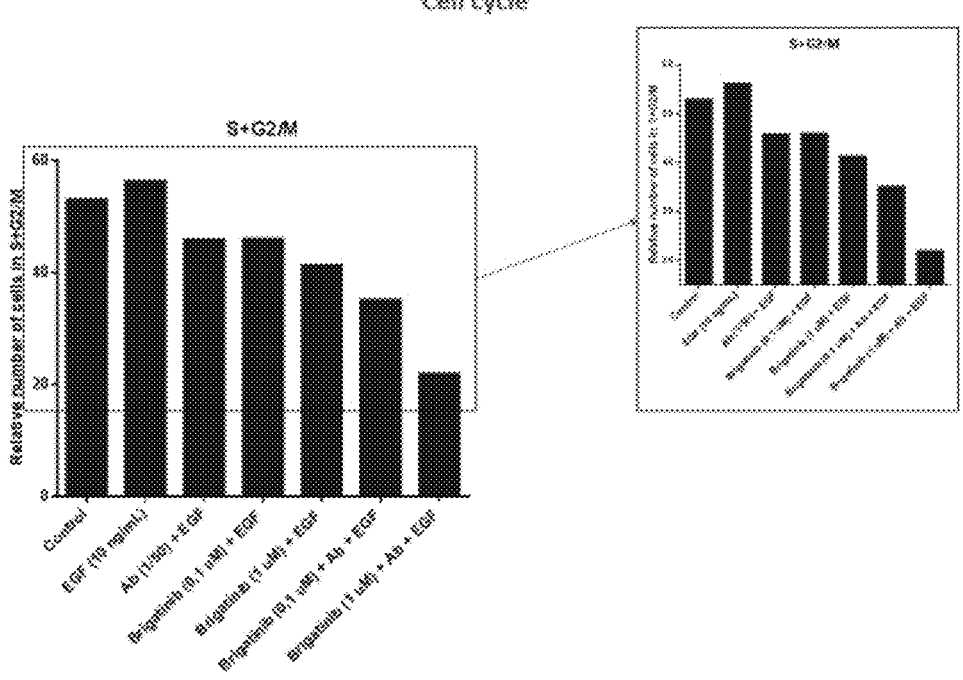
FIG. 35 shows the relative number of H2228 cells, an ALK translocated cell line, in S and G2/M phases of the cell cycle in response to the anti-IN01 antibody, referred to as "Ab," EGF, and 1 mM Brigatinib, in combination and alone.
Figure 36:
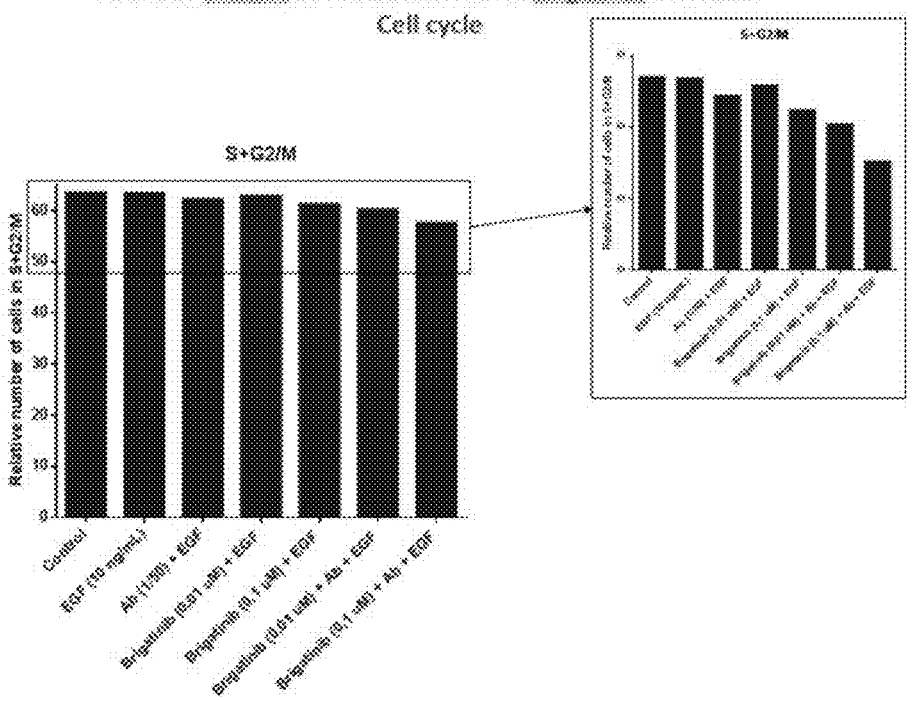
FIG. 36 shows the relative number of H3122 cells, an ALK translocated cell line, in S and G2/M phases of the cell cycle in response to the anti-IN01 antibody, referred to as "Ab," EGF, and 1 mM Brigatinib, in combination and alone.
Figures 37, 38:
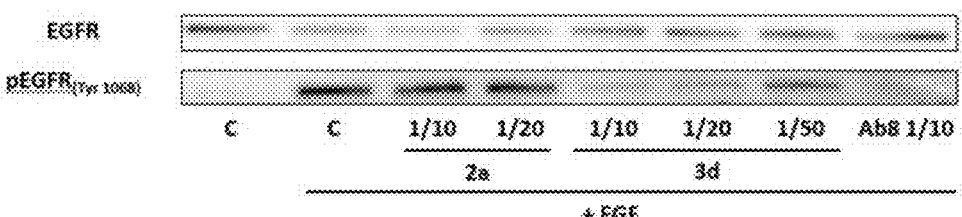
FIG. 37 summarizes the main alterations of the H2228, A549, and SW900 model cell lines.
FIG. 38 shows the pEGFR signaling response in SW900 cell lines to patient-derived anti-EGF antibody titers, and to the anti-IN01 antibody, referred to as "Ab8," in the presence of EGF.
Figure 39:
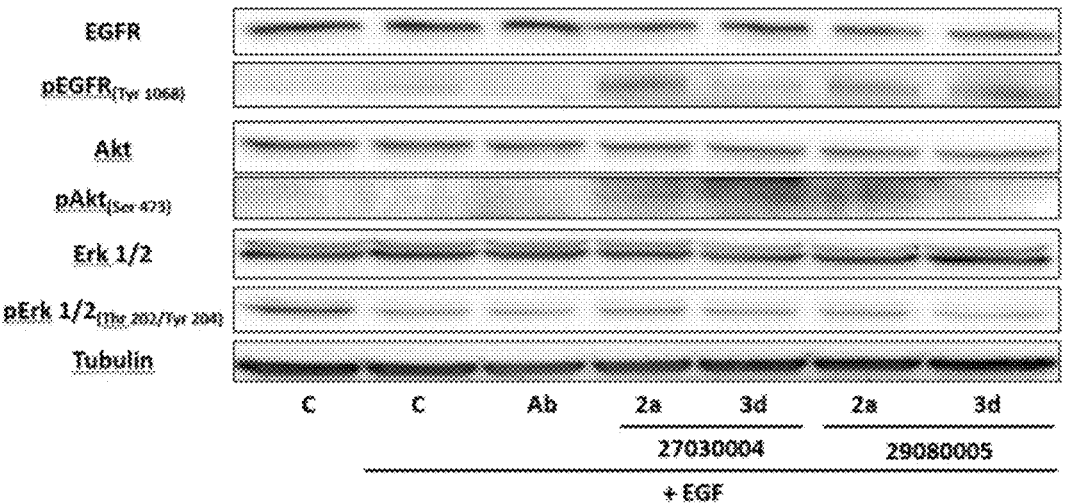
FIG. 39 shows the pEGFR, pAkt, and pErk½ signaling response in SW900 cell lines to two different patient-derived anti-EGF antibody titers, and to the anti-IN01 antibody, referred to as "Ab," in the presence of EGF.
Figure 40:
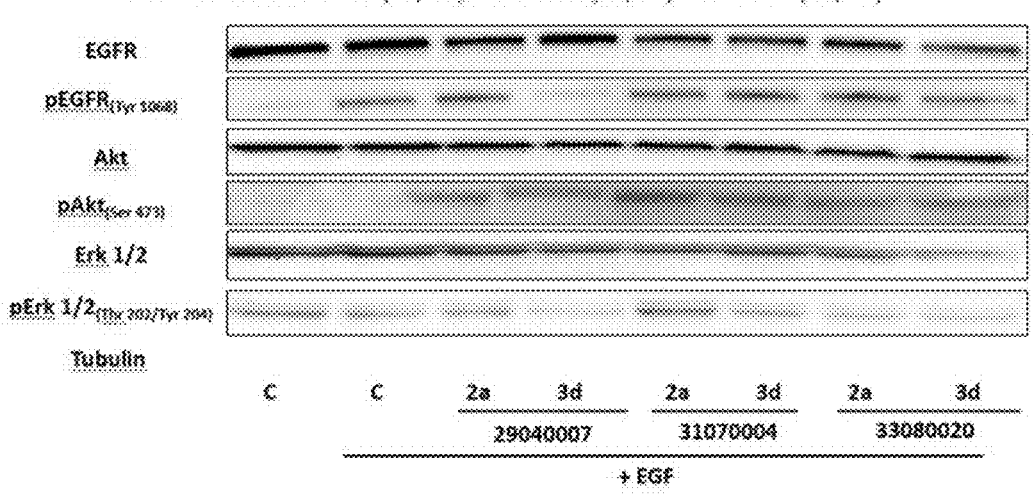
FIG. 40 shows the pEGFR, pAkt, and pErk½ signaling response in SW900 cell lines to three different patient-derived anti-EGF antibody titers, and to the anti-IN01 antibody in the presence of EGF.
Figure 41:
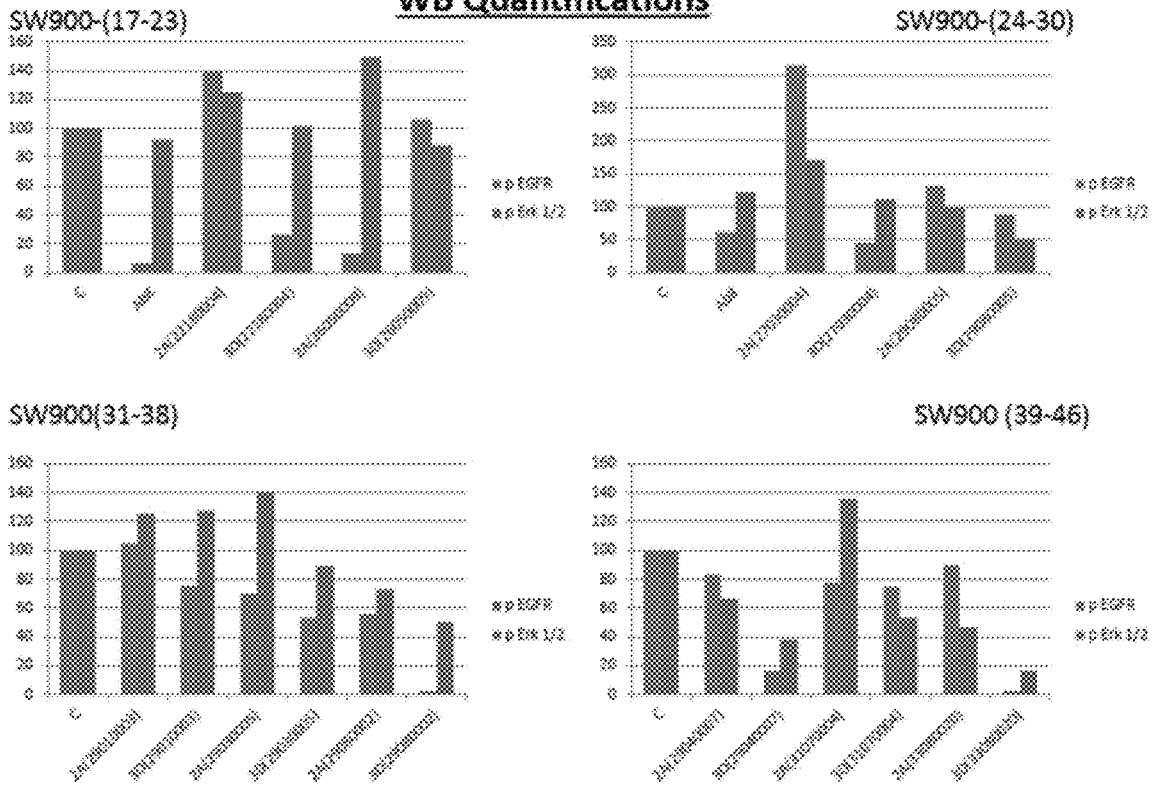
FIG. 41 shows the western blot quantifications of the pEGFR and pErk½ signaling response in SW900 cells to patient-derived anti-EGF antibody titers, and to the anti-IN01 antibody, referred to as "Ab8."

FIGS. 35 and 36 show the decrease in G2/M phase H2228 and H3122 cells, respectively, in response to Brigatinib in combination with the anti-IN01 antibody, as assessed by flow cytometry.

FIG. 42 shows the signaling response to patient titers of anti-IN01 antibody in H228 cells.

Example 6: LC-2/ad (RET Translocation) Mutant Cell Line Response to Anti-IN01 Antibody/TKI Combination Therapies The RET proto-oncogene gain of function is associated the development of various types of human cancer, including medullary thyroid carcinoma, multiple endocrine neoplasias type 2A and 2B, pheochromocytoma and parathyroid hyperplasia. RET is phosphorylated downstream of EGFR with EGF induction. Although EGF stimulates RET cell line growth, the anti-IN01 antibody significantly enhanced BLU667 inhibition of this effect in LC-2/ad (RET translocated) cells (FIGS. 78-81).

Example 7: SW900 wt KRAS/wt ALK Cell Line Response to Anti-INN Antibody Patient Titers FIGS. 38-41 show the signaling response of SW900 cells to different patient titers of the anti-IN01 antibody, demonstrating that active immunization using the anti-IN01 peptide (SEQ ID NO: 2) has significant effects on EGFR and downstream signaling, known to lead to decreased cell division and viability.

Example 8: Anti-Epidermal Growth Factor Vaccine Antibodies Increase the Antitumor Activity of Kinase Inhibitors (TKIs) in Non-Small Cell Lung Cancer Cell Lines Advanced NSCLC patients harboring MET amplification and MET exon 14 deletion (METΔex14) derived benefit from treatment with MET tyrosine kinase inhibitors (TKIs). In patients with alterations in RAS family genes, no targeted therapy was yet approved and trials of MEK inhibitors, such as Trametinib, in NSCLC failed to show clinical benefit. Herein, antibodies generated by vaccination (anti-EGF antibodies) potentiated the effects of EGFR TKIs in epidermal growth factor receptor mutant (EGFR-mut), ALK and RET translocated cells growing in vitro and prevent the emergence of resistance to EGFR TKIs. The goal was to determine the effects of anti-EGF VacAbs, MET TKIs, MEK inhibitors and combinations in cell lines harboring MET and NRAS alterations.

Anti-EGF VacAbs were generated in rabbits, purified and titrated. Cell lines were treated with anti-EGF VacAbs alone and in combination with MET and MEK inhibitors in MET amplified, METΔex14 and NRAS mutant NSCLC cell lines (EBC-1, Hs746T andHCC15). Cell viability and long-term growth curves were determined by MTT, changes of total and phosphorylated proteins by Western blot, cell cycle and apoptotic effects by flow cytometry and emergence of resistance by direct microscopic examination in low density cultures.

Anti-EGF antibodies suppressed EGF and TGFα-induced cell proliferation and inhibited EGFR phosphorylation and downstream ERK signaling in all cell lines tested. In combination, the anti-EGF antibodies significantly enhanced the antitumor activity of Capmatinib and Tepotinib in EBC and Hs746T and Trametinib in HCC15 cells. In these cell lines, western blotting demonstrated that the combination of anti-EGF antibodies with the inhibitors tested effectively suppressed EGFR downstream pathways. Cell cycle experiments were performed to further investigate these effects. The addition of EGF significantly increased the number of cells in S+G2/M, as expected, while anti-EGF antibodies and the inhibitors reversed this stimulation.

Example 9: Anti-IN01 Antibody in Combination with TKI Inhibitors Tepotinib and Capmatinib in MET Amplified and METex14 Cell Lines The anti-IN01 (BVN22E) antibody was developed from SEQ ID NO: 2, which consists of two repeated synthetic EGF Targeted Signaling Pathway (SEQ ID NO: 7) domains, Glycine-Serine repeat linkers, and a CTB sequence (SEQ ID NO: 25). In this example, EBC1 and Hs746T cell lines, which carry MET amplifications and MET exon 14 deletions were used (FIG. 82).

EBC1 and Hs746T short term cell viability was tested in the presence of (FIGS. 83-88) EGF, the anti-IN01 antibody, "Ab," and different concentrations of Capmatinib and Tepotinib. The effects of different concentations of Tepotinib on pMET, pEGFR, pAkt, and pErk½ activation in EBC1 cells and Tepotinib on pMET signaling in EBC1 cells were also observed (FIGS. 85 and 87).

The long-term effects on EBC1 cell viability of incubation with 0.75 nM and 0.25 nM Tepotinib, EGF, and the anti-IN01 antibody were also observed in EBC1 cells.

The long-term effects on EBC1 cell viability of incubation with 2.0 nM and 0.5 nM Tepotinib, EGF, and the anti-IN01 antibody were observed in Hs746T cells.

In summary, the anti-IN01 antibody which inhibits activation of the epidermal growth factor receptor (EGFR) was shown to significantly enhance the effects of NTKIs targeting EGFR effector proteins, including but not limited to Trametinib, Taselisib, Alpelisib, Copanlisib, and Erlotinib by reducing cell signaling downstream of EGFR that regulates tumor cell growth and viability, and notably, delaying the onset of resistance to the NTKI compared to the NTKI alone. Patient therapies derived from the IN01 non-natural synthetic polypeptide (NNSP), and/or antibody thereof, in combination with NTKIs, thus have the potential to diminish or eradicate previously untreatable cancers. It is further contemplated that antibodies to other growth factors and their receptors, used in combination with non-tyrosine targeting kinase inhibitors, would similarly enhance the effect of the NTKI and delay the onset of resistance.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

EQUIVALENTS

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

We claim:

1. A method of treating non-small cell lung carcinoma (NSCLC) or colorectal cancer (CRC) in a subject, comprising the steps of:

administering to the subject a non-tyrosine targeting kinase inhibitor (NTKI) that inhibits one or more kinases involved in intracellular signaling initiated by epidermal growth factor (EGF), and a non-natural synthetic polypeptide (NNSP), wherein the NNSP comprises a polypeptide comprising an amino acid sequence at least 95% identical to SEQ ID NO: 7 or SEQ ID NO: 8, an immunogenic polypeptide comprising a cholera toxin B (CT-B) protein, or a fragment thereof, and a linker, wherein the NNSP is separated from the immunogenic polypeptide by the linker optionally wherein the NNSP is from a cell that expresses SEQ ID NO: 7 or SEQ ID NO: wherein administration of the NNSP induces an immune response against EGF and reduces EGF-mediated receptor signaling, thereby delaying acquisition of resistance to the NTKI in the subject.

2. The method of claim 1, wherein the NNSP comprises SEQ ID NO: 2 or SEQ ID NO: 6, or wherein the NNSP is produced by a cell expressing SEQ ID NO: 2 or SEQ ID NO: 6.

3. The method of claim 1, wherein the NTKI is Trametinib, Taselisib, Alpelisib, Copanlisib, Idealisib, Duvelisib, Buparlisib, Umbralisib, PX-866, Dactolisib, CUDC-907, Voxtalisib (SAR245409, XL765) ME-401, IPI-549, SF1126, INK1117 Pictilisib, XL147 (SAR245408), GSK1059615, ZSTK474, PWT33597, IC87114, TG100-115, CAL 263, RP6503, GNE-477 AEZS-136, Encorafenib, Vemurafenib, Dabrafenib, GDC-0879, PLX-4720, Cobimetinib, Binimetinib, Selumetinib, PD-325901, PD035901, CI-1040, TAK-733, Perifosine, Palomid 529 or pharmaceutically acceptable salts thereof.

4. The method of claim 1, wherein the linker is selected from the group consisting of SSG, GSSG (SEQ ID NO: 9), SSGGG (SEQ ID NO: 10), SGG, GGSGG (SEQ ID NO: 11), GGGGS (SEQ ID NO: 12), SSGGGSGG (SEQ ID NO: 13), SSGGGGSGGG (SEQ ID NO: 14), TSGGGSG (SEQ ID NO: 15), TSGGGGSGG (SEQ ID NO: 16), SSGGSGGGSG (SEQ ID NO: 17), SSGGGSGGGSSG (SEQ ID NO: 18), GGSGGTSGGGGSG (SEQ ID NO: 19), SGGTSGGGGSGG (SEQ ID NO: 20), GGSGGTSGGGGSGG (SEQ ID NO: 21), SSGGGGSGGGSSG (SEQ ID NO: 22), SSGGGSGGSSGGG (SEQ ID NO: 23), and SSGGGGSGGGSSGGG (SEQ ID NO: 24), optionally wherein the linker is GSSG (SEQ ID NO: 9).

5. The method of claim 1, wherein the antibody is administered at about 0.01-0.1 µg/kg to about 95 mg/kg body weight; or from about 0.1-1.0 µg/kg to about 90 mg/kg body weight; or from about 0.5-5.0 µg/kg to about 80 mg/kg body weight; or from about 1.0-10.0 µg/kg to about 60 mg/kg body weight; or from about 5.0-20.0 µg/kg to about 50 mg/kg body weight; or from about 20-50 µg/kg to about 25 mg/kg body weight; or from about 50-100 µg/kg to about 20 mg/kg body weight, In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 µg/kg body weight.

* * * * *